US006635806B1

(12) United States Patent
Kriz et al.

(10) Patent No.: US 6,635,806 B1
(45) Date of Patent: Oct. 21, 2003

(54) METHODS AND COMPOSITIONS FOR EXPRESSION OF TRANSGENES IN PLANTS

(75) Inventors: Alan L. Kriz, Gales Ferry, CT (US); Michael H. Luethy, Old Mystic, CT (US); Dale A. Voyles, Griswold, CT (US)

(73) Assignee: DeKalb Genetics Corporation, DeKalb, IL (US)

( * ) Notice: Subject to any disclaimer, the term of this patent is extended or adjusted under 35 U.S.C. 154(b) by 0 days.

(21) Appl. No.: 09/078,972

(22) Filed: May 14, 1998

(51) Int. Cl.$^7$ .......................... A01H 5/00; C12N 15/82; C12N 15/29

(52) U.S. Cl. ...................... 800/287; 531/24.1; 800/298; 800/300; 800/301; 800/302; 800/303; 800/312; 800/314; 800/317.2; 800/317.3; 800/317.4; 800/320; 800/320.1; 800/320.2; 800/320.3

(58) Field of Search .............................. 435/320.1, 419, 435/468; 536/24.1; 800/278, 298, 300, 301, 302, 303, 312, 314, 317.2, 317.3, 317.4, 320, 320.1, 320.2, 320.3, 287

(56) References Cited

FOREIGN PATENT DOCUMENTS

| WO | WO 95/06128 | 3/1995 |
|---|---|---|
| WO | WO 97/46690 | 12/1997 |

OTHER PUBLICATIONS

Donald et al, "Mutation of either G box of I box sequences profoundly affects expression from the Arabidopsis rbcS–1A promoter", 1990, The EMBO Journal, vol. 9, No. 6, pp. 1717–1726.*
Kim et al, "a 20 nucleotide upstream element is essential for the noapline synthase (nos) promoter activity", 1994, Plant Molecular Biology, vol. 24, 105–117.*
Chen et al, "Minimal regions in the Arabidopsis Pistillata promoter responsive to the apetala3/pistillata feedback control do not contain a CArG box", 2000, Sex Plant Reprod. vol. 13, 85–94.*
Leite et al., "Nucleotide sequence of a cDNA Clone Encoding γ–coixin from *Coix lacryma–jobi* seeds," *Plant Physiol.* 97:1604–1605, 1991.
Leite et al., "Phylogenetic relationship of zeins and coixins as determined by immunological cross–reactivity and Southern Blot analysis," *Plant Mol. Biol.* 14:743–751, 1990.
Neto et al., "The involvement of opaque 2 on β–prolamin gene regulation in maize and Coix suggests a more general role for this transcriptional activator," *Plant Mol. Biol.* 27:1015–1029, 1995.
Yunes et al., "The transcriptional activator Opaque2 recognized two different target sequences in the 22–kD–like α–prolamin genes," *The Plant Cell* 6:237–249, Feb. 1994.

Vettore et al., "The molecular and functional characterization of an Opaque2 homologue gene from Coix and a new classification of plant bZIP proteins," *Plant Molecular Biology* 36(2):249–263, 1998.
Vettore et al., "The molecular and functional characterization of an Opaque2 homologue gene from Coix and a new classification of plant bZIP proteins," *Plant Mol. Biol.* 36:249–263, 1998.
Ottoboni et al., Sequence analysis of 22kDa–like α–coixin genes and their comparison with homologous zein and kafirin genes reveals highly conserved protein structure and regulatory elements, *Plant Molecular Biology*, 21:765–778, 1993.
Ottoboni et al., Sequence analysis of 22kDa–like α–coixin genes and their comparison with homologous zein and kafirin genes reveals highly conserved protein structure and regulatory elements, EMBL GenBank Database Accession No. X63113 from the World Wide Web at site: http://www.ncbi.nlm.nih.gov.
Belanger and Kriz, "Molecular basis for allelic polymorphism of the maize globulin–1 gene," *Genet.*, 129:863–872, 1991.
de Freitas et al., "Structural characterization and promoter activity analysis of the gamma–kafirin gene from sorghum," *Molecular and General Genetics*, 245(2):177–186, 1994.
Dehio and Schell, "Identification of plant genetic loci involved in a posttranscriptional mechanism for meiotically reversible transgene silencing," *Proc. Natl. Acad. Sci. USA*, 91:5538–5542, 1994.
Ingelbrecht et al., "Post–transcriptional silencing of reporter transgenes in tobacco correlates with DNA methylation," *Proc. Natl. Acad. Sci. USA*, 91:10502–10506, 1994.
Jorgensen, "Altered gene expression in plants due to trans interactions between homologous genes," *Trends Biotechnol.*, 8:340–44, 1990.
Jorgensen, "Cosuppression, flower color patterns, and metastable gene expression states," *Science*, 268:686–691, 1995.
Kriz et al., "Structural and transcriptional analysis of DNA sequences flanking genes that encode 19 kilodalton zeins," *Mol. Gen. Genet.*, 207(1):90–98, 1987.
Langridge and Feix, "A zein gene of maize is transcribed from two widely separated promoter regions," *Cell*, 34:1015–1022, 1983.

(List continued on next page.)

Primary Examiner—David T. Fox
Assistant Examiner—Cynthia Collins
(74) Attorney, Agent, or Firm—Fulbright & Jaworski L.L.P.

(57) ABSTRACT

Methods and compositions for the expression of transgenes in monocot plants including maize are disclosed. In the invention, gene silencing is avoided by use of monocot-homologous sequences from plants of the genus Coix for transformation. Included in these transgene sequences are Coix promoters, enhancers, coding sequences and terminators. Suitable alternatives to maize-derived transgenes are desirable for expression in maize in that homology-based gene silencing can limit or effectively eliminate transgene expression.

15 Claims, 7 Drawing Sheets

OTHER PUBLICATIONS

Lindbo et al., "Induction of a highly specific antiviral state in transgenic plants: implications for gene regulation and virus resistance," *Plant Cell,* 5:1749–1759, 1993.

Matzke and Matzke, "How and why do plants inactivate homologous (trans)genes?," *Plant Physiol.,* 107:679–685, 1995.

Matzke et al., "A variety of epistatic interactions can occur between partially homologous transgene loci brought together by sexual crossing," *Mol. Gen. Genet.,* 236:379–86, 1993.

Matzke et al., "Homology–dependent gene silencing in transgenic plants: epistatic silencing loci contain multiple copies of methylated transgenes," *Mol. Gen. Genet.,* 244:219–229, 1994.

Meyer, "Understanding and controlling transgene expression," *Trends Biotechnol.,* 13:332–337, 1995.

Mueller et al., "Homology–dependent resistance transgenic virus resistance in plants related to homology–dependent gene silencing," *Plant J.,* 7:1001–1013, 1995.

Napoli et al., "Introduction of a chimeric chalcone synthase gene into petunia results in reversible co–suppression of homologous genes in trans," *Plant Cell,* 2:279–289, 1990.

Neuhuber et al., "Susceptibility of transgene loci to homology–dependent gene silencing," *Mol. Gen. Genet.,* 244:230–241, 1994.

Ottoboni et al., "Sequence analysis of 22 KDA–like aplpha coixin genes reveals highly conserved protein structure and regulatory elements," *Plant Molecular Biology,* 21(5):765–778, 1993.

Park et al., "Gene silencing mediated by promoter homology occurs at the level of transcription and results in meiotically heritable alterations in methylation and gene activity," *Plant,* 9:183–194, 1996.

Reina et al., "Sequence analysis of a genomic clone encoding a Zc2 protein from Zea mays W64 A," *Nucl. Acids Res.,* 18(21):6426, 1990.

Siebert et al., "An improved PCR method of walking in uncloned genomic DNA," *Nucl. Acids Res.,* 23:1087–1088, 1995.

Van Blokland et al., "Transgene–mediated suppression of chalcone synthase expression in *Petunia hybrida* results from an increase in RNA turnover," *Plant J.,* 6:861–877, 1994.

Van der Krol et al., "Flavonoid genes in petunia: addition of a limiting number of copies may lead to a suppression of gene expression," *Plant Cell,* 2:291–99, 1990.

Vaucheret, "Identification of a general silencer for 19S and 35S promoters in a transgenic tobacco plant: 90bp of homology in the promoter sequence are sufficient for trans–inactivation," *C.R. Acad. Sci. III,* 316:1471–83, 1993.

Wandelt and Feix, "Sequence of a 21 kd zein gene from maize containing an in–frame stop condon," *Nucl. Acids Res.,* 17(6):2354, 1989.

* cited by examiner

```
gamma zein     ------------------------------------------------
gamma coixin   ------------------------------------------------
gamma kafirin  GATTTGGGTTAAGAACAGTAGTCGGACATTCCACGCTTTGTTAAGTTCTT     50 gamma zein     ----------------------ATATATATATACATATATATATA          23
gamma coixin   -------------------------------------------G           1
gamma kafirin  TTTTTACATAACAAGAATAGAATCACGCTCTGTAGGCTCGT-CAGAC-CG     98 gamma zein     TATATATATATAAACCGTAGCAATGCACGGGCATATAACTAGTGC-AACT    72
gamma coixin   GACCGGT-TACAGCACACCACTGTGGGTGGTCTCA-AGGCAGTACCAAAC    49
gamma kafirin  TACCTTT-CTAAGGAAGTCGCTTTGGGTAGT-TCA---GTTG-GCGAGA-   141 gamma zein     TAATACATGTGTGTATTAAGATGAATAAGAGGGT-ATCCA-AATAAAAAA   120
gamma coixin   TATAGCATCCATATAGCAGCAGAATCACCTGTCTTGTCTACAAGACAGAA    99
gamma kafirin  -AAAGCCTTCCTTACCTTTGCAGGTCCATCGGGC-CGACTAC------AA   182 gamma zein     CTTGTTTGCTTACGTCTGGATCAAATTGGGTTGGAAACGATTAAATCTCT   170
gamma coixin   CCAAT--GCAT-CAACT---TCAA--GGGAGTACCAGCGTCTTCTTGACT   141
gamma kafirin  CCCGT--GGCT-CAA----TC----------CC-G-G--TTCTTG-CG    208 gamma zein     TCCTAGTCAAAATTGAATAGAAGGAGATTTAATCTCTTCCCAATCCCCTTC   220
gamma coixin   GTCT-TTCAGAATTGTG-GCATTCTTGTTGGAAGCATAGCAGTGTAGGTT   189
gamma kafirin  GTCT-CTT-----TGGCA-ACATTCTTGTTGGAAG-ATTACCA--GAAGGTTT  248 gamma zein     GATCATCCAGGTGCAACCGT-ATAAGT-CCTAAAGTGGTGAGGAACACGA   268
gamma coixin   GCTCATTCACGGATAATCTTCGACAC----GTAAAGTGATGAGGAATACGG   235
gamma kafirin  GCTC---CACGGGTAATCTTGACACGTATGTAAAGTGATGAGGAACATTG   295 gamma zein     AACAACCATGCATTGGCATGTAAAGCTCCAAGAATTTGTTGTATCC-T-T   316
gamma coixin   AACGAC----CATTGGCATGTAGAGCTGTATGAATTGGTGTTATCCATAC   281
gamma kafirin  AACGAA----CATTGGCATGTA-AGCTCTAT-AATTGGTGTTATCCAT--   337 gamma zein     AACAAC-TGACAGAACATCAACCAAAATTGCACGTCAAGGGTATTGGGTA   365
gamma coixin   AACAAC-TGGCAGAACATCA--CAAAATTGCACGTCAATGG-ATTGGGTC   327
gamma kafirin  AACAACGTGGCAGAACATCA--G-AAATTGCACGTCAAGGG-ATTGGGTC   383 gamma zein     AGAAACAATCAAACAAATCCTCTCTGTGTGCAAAGAAAC-ACGGTGAGTC   414
gamma coixin   AGAAACAAATCGTCTCCTTGTAGCT-TGTACAATGAAGTGATGGTGAGTC   376
gamma kafirin  AGAAACAAATCGTCTCC-----G---TGTACAACGAAG---TGGTGAGTC   422 gamma zein     ATG-CCGAGATCATACTCATCTGATATACATGCT-TACAGCTCACAAG--   460
gamma coixin   ATGAGTCACACTGATCCGATCTGATATATATGCCAAATAGCTCACACGAC   426
gamma kafirin  ATGAGCCA---TG--TTGATCTGATATATA---C--ATAGCACACACGAC   462
```

FIG. 8-1

```
gamma zein     -ACATTACAAACAAC-TCATA-T-TGCATTACAAAGATCGTTTCA----T     502
gamma coixin   AACATTACAAACAACCCCATACTATACATCACAAAGTTTGTTTCA----T     472
gamma kafirin  A---TCACAAACAA-GTCATAC--TACATTACAGAGTTAGTTTCACCTTT    506 gamma zein     --G-AAAAATAAAATAGGCC---GGACAGGACAAAAATC----CTTGAC    541
gamma coixin   --GAAAAAACAAATAAGTATGCAGGAGGGGACAATAATCCTTGCTTGAC    519
gamma kafirin  CAAGTAAAAACAAAGTAGGCCGGA-GAGAGGACAATAATC----CTTGAC   551 gamma zein     GAGTAAAGTAAATTTACAA---CAAAAAAAGCCATATGT------CAA    582
gamma coixin   GCGTAAAGTGAATTTACAAAGCCATATATCAACCTATATCTAATTAATAA  569
gamma kafirin  GTTGTAAAGTGAATTTACAAAGCCATATATCAATTTATATCTAATT-----  596 gamma zein     GCTAAATCTA-ATTCGTTTTACGTAGATCAACA----ACCTGTAGAAGG   626
gamma coixin   GTTCGTTATATATACGCACGATGATCATCAACAACCGTACCTGTGAAAGG  619
gamma kafirin  ---CGTT---T-CATGTA---GAT-ATCAACA----ACCTGTAAAAGG   629 gamma zein     CAACAAAACTGAGCCACGCAGAAGTACAGAATGATTCCAGATGA------   670
gamma coixin   CAACAAAA-TGAGCCACGCAAAAATTGCAGAATGAATCCATATGATGACGA 668
gamma kafirin  CAACAAAT-TGAGCCACGCAAAATTACA-AGTGAGTCCA-A--AT----A  670 gamma zein     ----AQCATCGACGTGCTACGTAAA-GAGAGTGACGAGTCATATACATTT  715
gamma coixin   ACGTACACTCGGCTTGCTACAT-AAAGTGAATGATGAGTCATAAATATTT  717
gamma kafirin  A---ACCCTC-AGATGCTACATAAAAGTGAATGATGAGTCATGTATATCT  716 gamma zein     GGCAAGAAACCATGAA-GCTGCCTACAGCCGTC-TCGGTGGCATAGGAAC  763
gamma coixin   GGCAAGAAACCGTGAAAGCTAC--ACAGCCGTCGTCAGTAGCACAGGAAC  765
gamma kafirin  GGCAAGAAACTGTAGAAGCTAC--A-----GTCATCGGTAGCAAAGAAAC  759 gamma zein     ACAAGAAATTGTGTTAATTAATCAAAGCTATAAATAACCCTCGGATGCCT  813
gamma coixin   ACAAGAAACTGTGC----TAATCGAAGCTATAAATAACCCTAGTATGCCT  811
gamma kafirin  ACAAGAAAATGTGC----TAATAAAAGCTATAAATAACCCTCGTTACGCCT 805 gamma zein     GTGGACTTCTCCATCACCACCACTGG--GTC-TTCAGACCATTAGCTT--  858
gamma coixin   ATGCACTTCTCCATCACCACTACCCAT-ATC-TTCAGTCTATTTACCT-T  858
gamma kafirin  ATGCACATCTCCATCACCACCACTGGTCTTTCATTCAGCCTATTAACTTAT 855 gamma zein     ---TATCTACTCCAGAGCGCAGAAGAACCCGATCGACACCATG         898
gamma coixin   CTCTATCTACTCCAGAGAGCACAGAA----GATCGACACCATG         897
gamma kafirin  ATCTATCTACTCCAGAGCAGACAAGA----ACTCGACACCATG         894
```

FIG. 8-2

SEQUENCE LISTING

```
<160> NUMBER OF SEQ ID NOS:  28

<210> SEQ ID NO 1
<211> LENGTH: 22
<212> TYPE: DNA
<213> ORGANISM: Artificial Sequence
<220> FEATURE:
<223> OTHER INFORMATION: Description of Artificial Sequence:  Synthetic
      Primer

<400> SEQUENCE: 1
ctggaactgg aacgggcttg ga                                                  22

<210> SEQ ID NO 2
<211> LENGTH: 28
<212> TYPE: DNA
<213> ORGANISM: Artificial Sequence
<220> FEATURE:
<223> OTHER INFORMATION: Description of Artificial Sequence:  Synthetic
      Primer

<400> SEQUENCE: 2
gcgagggcaa cgagcagcac cttcatgg                                            28

<210> SEQ ID NO 3
<211> LENGTH: 22
<212> TYPE: DNA
<213> ORGANISM: Artificial Sequence
<220> FEATURE:
<223> OTHER INFORMATION: Description of Artificial Sequence:  Synthetic
```

Primer

<400> SEQUENCE: 3
gtaatacgac tcactatagg gc                                              22

<210> SEQ ID NO 4
<211> LENGTH: 19
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 4
actatagggc acgcgtggt                                                  19

<210> SEQ ID NO 5
<211> LENGTH: 31
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 5
ggctcgaggg accggttaca gcacaccact g                                    31

<210> SEQ ID NO 6
<211> LENGTH: 29
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 6
ggtctagagg tgtcgatctt ctgtgctct                                       29

<210> SEQ ID NO 7
<211> LENGTH: 29
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 7
ggccatgggg tgtcgatctt ctgtgctct                                       29

<210> SEQ ID NO 8
<211> LENGTH: 894
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 8
ggaccggtta cagcacacca ctgtgggtgg tctcaaggca gtaccaaact atagcatcca     60
tatagcagca gaatcacctg tcttgtctac aagacagaac caatgcatca acttcaaggg   120
agtaccagcg tcttcttgac tgtctttcag aattgtggca ttcttgttgg aagcatagca   180
gtgtaggttg ctcattcacg gataatctcg acacgtaaag tgatgaggaa tacgaacga    240 ccattggcat gtagagctgt atgaattggt gttatccata caacaactcg cagaacatca   300

```
caaaattgca cgtcaatgga ttgggtcaga aacaaatcgt ctccttgtag cttgtacaat      360
gaagtgatgg tgagtcatga gtcacactga tccgatctga tatatatgcc aaatagctca      420
cacgacaaca ttacaaacaa ccccatacta tacatcacaa agtttgtttc atgaaaaaac      480
aaataagtat gcaggagggg acaataatcc ttgcttgacg cgtaaagtga atttacaaag      540
ccatatatca acctatatct aattaataag ttcgttatat atacgcacga tgatcatcaa      600
caaccgtacc tgtgaaaggc aacaaaatga gccacgcaaa aatgcagaat gaatccatat      660
gatgacgaac gtacactcgg cttgctacat aaagtgaatg atgagtcata aatatttggc      720
aagaaaccgt gaaagctaca cagccgtcgt cagtagcaca ggaacacaag aaactgtgct      780
aatcgaagct ataaataacc ctagtatgcc tatgcacttc tccatcacca ctacccatat      840
cttcagtcta tttaccttct ctatctactc cagagagcac agaagatcga cacc            894
```

```
<210> SEQ ID NO 9
<211> LENGTH: 23
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 9
ctcagcccca gcagccacat cca                                              23

<210> SEQ ID NO 10
<211> LENGTH: 22
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 10
gtgcggcagc caatgacaag tc                                               22

<210> SEQ ID NO 11
<211> LENGTH: 412
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 11
actgaagaaa ctatatccta ctgtaataat aatgatgtaa tatagccgct ggcgagctaa      60
gctagtttag tcatttagcg cggcgatggg taataaaagt gtcatccatc accatgggtg     120
acaatatatg cgaacaaatg acctgaagat gaacaattga aatgaaaagg aaaatatatt     180
acaattcaac gagatatcct ctcgatcgta tcacgtgtcc acaggggtgg atccatgccc     240
cgggctgccc gggctgcagc ccggggcgta gaccaaaaat cccttttagcg attcttttttt     300 tcagttcaat tttgccaata aaactacat ttagccctac ctgatgcggt ctaaaatttt      360
tttacactag tttagcccct cctgtaatgt gtttctagat caggcaatgt at             412

<210> SEQ ID NO 12
<211> LENGTH: 31
<212> TYPE: DNA
<213> ORGANISM: Artificial Sequence
<220> FEATURE:
<223> OTHER INFORMATION: Description of Artificial Sequence: Synthetic
      Primer
```

```
<400> SEQUENCE: 12
ggctcgaggg accggttaca gcacaccact g                              31

<210> SEQ ID NO 13
<211> LENGTH: 21
<212> TYPE: DNA
<213> ORGANISM: Artificial Sequence
<220> FEATURE:
<223> OTHER INFORMATION: Description of Artificial Sequence:  Synthetic
      Primer

<400> SEQUENCE: 13
tcagtactgg gcaccgccgg c                                         21

<210> SEQ ID NO 14
<211> LENGTH: 21
<212> TYPE: DNA
<213> ORGANISM: Artificial Sequence
<220> FEATURE:
<223> OTHER INFORMATION: Description of Artificial Sequence:  Synthetic
      Primer

<400> SEQUENCE: 14
aaggtgctgc tcgttgccct c                                         21

<210> SEQ ID NO 15
<211> LENGTH: 29
<212> TYPE: DNA
<213> ORGANISM: Artificial Sequence
<220> FEATURE:
<223> OTHER INFORMATION: Description of Artificial Sequence:  Synthetic
      Primer

<400> SEQUENCE: 15
gggagctctc agtactgggc accgccggc                                 29

<210> SEQ ID NO 16
<211> LENGTH: 603
<212> TYPE: DNA
<213> ORGANISM: Artificial Sequence
<220> FEATURE:
<223> OTHER INFORMATION: Description of Artificial Sequence:  Synthetic
      Primer

<400> SEQUENCE: 16
atgaaggtgc tgctcgttgc cctcgctctc ctggctctca ctgcgagcgc cacctccacg    60
caaataggcg gcacgtgcgg ctgccaacca ccgcatctgc caccgccgcc ggttcatctg   120
ccgcctccgg ttcacctgcc cccgccggtt catctgccgc cgccacaatg ccactaccct   180
actcaaccgc cccggcctca gccccagcag ccacatccat gcccatacca accgcagcat   240
ccaagcccgt tccagttcca gcagccggga acctgcgttg gccaaggcac ccagatcctg   300
ggccagtgca ttgagttcct gaggcatcag tgcagcccgg cggcgacgcc ctactgctcg   360
ccacaatgcc aggcgttgcg gcagcagtgt tgccaccagc tcaggcaggt ggagccgctg   420
caccggcaac aggcgatctt cggcgtggtc ctgcagtcca tccagcagca gccgataggc   480
cagccgctcg cggcgctgat ggcggcgcaa atagcgcagc aactgacgga gatgtgcggt   540
gtgcggcagc caatgacaag tccctgccct tgcagcgctg ctgccggcgg tgcccagtac   600
tga                                                                603

<210> SEQ ID NO 17
```

```
<211> LENGTH: 377
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 17
agaagaagca cgtacgcggg cggaacgcgt gtcctgcctg gataccgcgc gcgagatgac      60
gtgcggcggc ggcgcgcgac taccgccggc gcggcatggc cctactacgg cggctgctgc     120
tgctgctacg tacgctgccg taaagtctcg gtcgccgtgc tagctctagc tagtcgttat     180
gtgtgttgtg ctttgtatgt gcgcgtgtct tgttgggaca tgcagtgtag tgctgctgta     240
tgcgtgtgtc ctttcttgat cggagtcgga gtggctgatg cacagcatgc tggatgtcaa     300
gtttatgatg aggaataaaa tgcaatgttc agggcgagat actacggttt tccttgacta     360
ccatgggatt tgtagaa                                                    377

<210> SEQ ID NO 18
<211> LENGTH: 222
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 18
gcactcggct tgctacataa agtgaatgat gagtcataaa tatttggcaa gaaaccgtga      60
aagctacaca gccgtcgtca gtagcacagg aacacaagaa actgtgctaa tcgaagctat     120
aaataaccct agtatgccta tgcacttctc catcaccact acccatatct tcagtctatt     180
taccttctct atctactcca gagagcacag aagatcgaca cc                        222

<210> SEQ ID NO 19
<211> LENGTH: 412
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 19
gtaagtatgc aggagggggac aataatcctt gcttgacgcg taaagtgaat ttacaaagcc    60
atatatcaac ctatatctaa ttaataagtt cgttatatat acgcacgatg atcatcaaca    120
accgtacctg tgaaaggcaa caaaatgagc cacgcaaaaa tgcagaatga atccatatga    180
tgacgaacgt acactcggct tgctacataa agtgaatgat gagtcataaa tatttggcaa    240
gaaaccgtga aagctacaca gccgtcgtca gtagcacagg aacacaagaa actgtgctaa    300
tcgaagctat aaataaccct agtatgccta tgcacttctc catcaccact acccatatct    360
tcagtctatt taccttctct atctactcca gagagcacag aagatcgaca cc            412

<210> SEQ ID NO 20
<211> LENGTH: 25
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 20
catcgagaca agcacggtca acttc                                           25
```

<210> SEQ ID NO 21
<211> LENGTH: 28
<212> TYPE: DNA
<213> ORGANISM: Artificial Sequence
<220> FEATURE:
<223> OTHER INFORMATION: Description of Artificial Sequence: Synthetic Primer

<400> SEQUENCE: 21
aagtccctgg aggcacaggg cttcaaga                                28

<210> SEQ ID NO 22
<211> LENGTH: 2647
<212> TYPE: DNA
<213> ORGANISM: Artificial Sequence
<220> FEATURE:
<223> OTHER INFORMATION: Description of Artificial Sequence: Synthetic Primer

<400> SEQUENCE: 22

```
tatgaattat tatgtattta ttaattttca gtcgatttaa aaaataaaag aaaagtaaat      60
tggagatttt acattgggaa cctagaaaat tttttatttt ttttctctct tccatcgtaa     120
cgattctggg ctgattgggc ctacagagag gagagcgaaa gcgaagtaat atgagatttt     180
acattaggaa ccctagaata ttttttattt tgttttttccc cttctagaaa agttggatgg    240
aggaggccat cggtaaaccg aacacggaca agatcagggg caaagaaaaa tatttggcaa     300
actaaaattt tggctctttta tagataggta tagatttggg ttaagaacag tagtcggaca    360
ttccacgctt tgttaagttc ttttttttaca taacaagaat agaatcacgc tctgtaggct    420
cgtcagaccg taccttttcta aggaagtcgc tttgggtagt tcagttggcg agaaaagcct    480
tcctaccttt gcaggtccat cgggccgact acaacccgtg gctcaatccc ggttcttgcg     540
gtgtcttggc aacattcttg ttggaagata ccagaaggtt gctccacggg taatcttgac    600
acgtatgtaa agtgatgagg aacattgaac gaacattggc atgtaagctc tataattggt     660
gttatccata acaacgtcgc agaacatcac aaattgcacg tcaagggatt gggtcagaaa     720
caaatcgtct ccgtgtacaa cgaagtggtg agtcatgagc catgttgatc tgatatatac     780
atagcacaca cgacatcaca aacaagtcat actacattac agagttagtt tcacctttca     840
agtaaaaaca aagtaggccg gagagaggac aataatcctt gacgtgtaaa gtgaatttac     900
aaagccatat atcaatttat atctaattcg tttcatgtag atatcaacaa cctgtaaaag    960
gcaacaaatt gagccacgca aaattacaag tgagtccaaa taaaccctca catgctacat    1020
aaaagtgaat gatgagtcat gtatatctgg caagaaactg tagaagctac agtcatcggt   1080
agcaaagaaa cacaagaaaa tgtgctaata aaagctataa ataaccctcg tacgcctatg   1140
cacatctcca tcaccaccac tggtcttcat tcagcctatt aacttatatc tatctactcc   1200
agagcagaca agaactcgac accatgaagg tgttgctcgt tgccctcgct ctcctggctc   1260
tcgcgagcgc cgcctccacg cttacaaccg gcggctgcgg ctgccagaca cctcatctac   1320
caccaccgcc ggttcatctg ccgccgccgg tgcatctgcc accgccggtg cacctgccgc   1380
cgccggttca cgtgccaccg ccgccaccac aatgccaccc acaccctact ctaccgcccc   1440
acccacatcc atgcgctaca tacccaccgc atccaagccc gtgccaccca gggcatcccg   1500
gatcctgcgg tgttggcggc ggccccgtca ccccgccgat cctgggccag tgcatcgagt   1560
tcctgaggca tcagtgcagc ccggcggcga cgccctactg ctcgccacag tgccaggcgt   1620
```

-continued

| | |
|---|---|
| tgcggcagca gtgctgtcag cagctcaggc aggtggagcc gctgcaccgg taccaggcga | 1680 |
| tcttcggcgt ggtcctgcag tccatccagc agcagcagcc gcaaggccag tcgtcaccgc | 1740 |
| tcccggcgct gatggcggcg caaatagcac agcaactgac ggcgatgtgc ggtctaggag | 1800 |
| tggggcagcc aagtccctgc gcttcttgca gcccttttgc cggtggtgtc cactattaaa | 1860 |
| gaaactatct atactgtaat aatgttgtat agccgccgga tagctagcta gttagtcatt | 1920 |
| cagcggcgat gggtaataat aaagtgtcat ccatccatca ccatgggtgg caacgtgagc | 1980 |
| aatgacctga ttgaacaaat tgaaatgaaa agaagaaata tgttatatgt caacgagatt | 2040 |
| tcctcataat gccactgaca acgtgtgtcc aagaaatgta tcagtgatac gtatattcac | 2100 |
| aatttttta tgacttatac tcacaatttg tttttttact acttatactc gaacaatttg | 2160 |
| ttgtgggtac cataacaatt tcgatcgaat atatatcaga aagttgacga agtaagctc | 2220 |
| actcaaaaag ttaaatgggc tgcggaagct gcgtcaggcc caagttttgg ctattctatc | 2280 |
| cggtatccac gattttgatg gctgagggac atatgttcgg cttaagctgc agctttgtag | 2340 |
| ttagttttgt ttttgattat atttaatact ctatgcatgt gcaccaagat ttttctggtg | 2400 |
| aattaaacaa ggcctaataa cgtgagtagc gtatctaact gtgacctata aagtagagca | 2460 |
| ccttttaga gtaggggctc ctttttttag aactctattt attgcaccca acttcaataa | 2520 |
| gggtctttc atccaaaatt aagagtcctt acattacatc taatcgtcta ttcattgtct | 2580 |
| atatttaat ataaatctta ctgtatatct tgtagcacac tagtatgcct caaagccgac | 2640 |
| aataaat | 2647 |

<210> SEQ ID NO 23
<211> LENGTH: 3704
<212> TYPE: DNA
<213> ORGANISM: Artificial Sequence
<220> FEATURE:
<223> OTHER INFORMATION: Description of Artificial Sequence: Synthetic Primer

<400> SEQUENCE: 23

| | |
|---|---|
| gtggcgcctg taccgcgtgt ggggacgatg agcgctccct gaacgctgtc ttgggagagc | 60 |
| tgcaagatga gacactccat cccgcgcagc ctgtcgtggc gtcctcctgg atggacacct | 120 |
| gcatcgctgt cgccctccac caactcacct gaacgaagaa tagaataaaa aatggaggga | 180 |
| gctgaggggg cagtggttgc gctgtaggga ggagagagac cgcgtcatta taagactatc | 240 |
| tgcaaccgtt acctctaaat ttttccctct atatcatttt ttccccatat tttccccct | 300 |
| attttttcat ctcccgcaac ggtttctcct aaatactccc cctatatctc actaccacta | 360 |
| taaaatatta ttttttatac caactatcaa ttttttatct actaacaatt actcgtggac | 420 |
| ccacagcaca gtgttaggga gatgaacagt gacacgctat atctgggggg agagagaaag | 480 |
| aggcgcgcgt agggggcgcg cggtaggggc actgctgcgg ctgtagagta cccctacac | 540 |
| gccggcatgc aagggaaggg ggcaatgttg cgcatagcct aaagagcgga tgaagcggct | 600 |
| tgcaatttgc acgctggatt cataaatagt gcatattact aaaaaagggg tggggacgta | 660 |
| ggtatagaga gtctattaga gttgatctaa gacccggttt atttcagatt ataatctgtc | 720 |
| cggattatat aatccagcgc aaataataca gtaggtaaac aaacaactag attatggggtt | 780 |
| cagattatat aatctaaacc ccagattatg ataatctcat aatctcctca agagtagctt | 840 |
| attggagatt attttggcaa aagacccact acccatggtt atgtaaatag aaattataat | 900 |
| atatatcatc tttttttctca ccttaaataa acaaataagg gtattgttgt ctttatgaat | 960 |

```
aatctacatt tgtataatct aaactaccaa acaactacat ctagattata atctggatta    1020
tataatttaa attataatct agattatata atttataagc tgaaacaacc cggccctaaa    1080
gcactatcgt atcacctatc tgatagtcac gggtttcgaa cgtccacttg cgtcgcacgg    1140
aattgcatgt ttcttgttgg aagcatattc acgcaatctc cacacataaa ggtttatgta    1200
taaacttaca tttagctcag tttaattaca gtcttatttg gatgcatatg tatggttctc    1260
aatccatata agttagagta aaaataagt ttaaatttta tcttaattca ctccaacata     1320
tacggattga gtacaatact catgtgcatc caaacaaact acttatattg aggtgaattt    1380
ggatagaaat taaactaact tacacactaa gccaatcttt actatattaa agcaccagtt    1440
tcaacgatcg tcccgcgtca atattattaa aaaactccta catttcttta taatcaaccc    1500
gcactcttat aatctcttct ctactactat aataagagag tttatgtaca aaataaggtg    1560
aaattatgta taagtgttct ggatattggt tgttaactcc atattcacac aacctaatca    1620
atagaaaaca tatgttttat taaaacaaaa tttatcatat atcatatata tatatataca    1680
tatatatata tatatatata taaaccgtag caatgcacgg gcatataact agtgcaactt    1740
aatacatgtg tgtattaaga tgaataagag ggtatccaaa taaaaaactt gttcgcttac    1800
gtctggatca aattgggttg gaaacgatta aatctcttcc tagtcaaaat tgaatagaag    1860
gagatttaat ctctcccaat ccccttcgat catccaggtg caaccgtata agtcctaaag    1920
tggtgaggaa cacagaacaa ccatgcattg gcatgtaaag ctccaagaat tgttgtatc     1980 cttaacaact cacagaacat caaccaaaat tgcacgtcaa gggtattggg taagaaacaa    2040
tcaaacaaat cctctctgtg tgcaaagaaa cacggtgagt catgccgaga tcatactcat    2100
ctgatataca tgcttacagc tcacaagaca ttacaaacaa ctcatattgc attacaaaga    2160
tcgtttcatg aaaaataaaa taggccggac aggacaaaaa tccttgacga gtaaagtaaa    2220
tttacaacaa aaaaaaagcc atatgtcaag ctaaatctaa ttcgttttac gtagatcaac    2280
aacctgtaga aggcaacaaa actgagccac gcagaagtac agaatgattc cagatgaacc    2340
atcgacgtgc tacgtaaaga gagtgacgag tcatatacat ttggcaagaa accatgaagc    2400
tgcctacagc cgtctcggtg cataggaac acaagaaatt gtgttaatta atcaaagcta     2460
taaataacgc tcgcatgcct gtgcacttct ccatcaccac cactgggtct tcagaccatt    2520
agctttatct actccagagc gcagaagaac ccgatcgaca ccatgagggt gttgctcgtt    2580
gccctcgctc tcctggctct cgctgcgagc gccacctcca cgcataacag cggcggctgc    2640
ggctgccagc caccgccgcc ggttcatcta ccgccgccgg tgcatctgcc acctccggtt    2700
cacctgccac ctccggtgca tctcccaccg ccggtccacc tgccgccgcc ggtccacctg    2760
ccaccgccgg tccatgtgcc gccgccggtt catctgccgc cgccaccatg ccactaccct    2820
actcaaccgc cccggcctca gcctcatccc agccacacc catgcccgtg ccaacagccg      2880
catccaagcc cgtgccagct gcagggaacc tgcggcgttg gcagcacccc gatcctgggc    2940
cagtgcgtcg agttcctgag gcatcagtgc agcccgacgg cgacgcccta ctgctcgcct    3000
cagtgccagt cgttgcggca gcagtgttgc cagcagctca ggcaggtgga gccacagcac    3060
cggtaccagg cgatcttcgg cttggtcctc cagtccatcc tgcagcagca gccgcaaagt    3120
ggccaggtcg cggggctgtt ggcggcgcag atagcgcagc aactgacggc gatgtgcggt    3180
ctgcagcagc cgactccatg cccctacgct gctgccggcg tgtccccca ctgaagaaac      3240 tatgtgctgt agtatagccg ctgccgctg gctagctagc tagttgagtc atttagcggc      3300
gatgattgag taataatgtg tcacgcatca ccatgggtgg cagtgtcagt gtgagcaatg    3360
```

−continued

```
acctgaatga acaattgaaa tgaaaagaaa atactccatc tgttccaaat taaaattcat    3420
tttaaccttt taataggttt atacaataat tgatatatgt tttctgtata tgtctaattt    3480
gttatcatcc atttagatat agacaaaaaa aaatctaaga actaaaacaa atgctaattt    3540
gaaatgaagg gagtatatat tgggataatg tcgatgagat ccctcgtaat atcaccgaca    3600
tcacacgtgt ccagttaatg tatcagtgat acgtgtattc acatttgttg cgcgtaggcg    3660
tacccaacaa ttttgatcga ctatcagaaa gtcaacggaa gcga                    3704
```

```
<210> SEQ ID NO 24
<211> LENGTH: 21
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 24
ggctcgagta agtatgcagg a                                              21

<210> SEQ ID NO 25
<211> LENGTH: 21
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 25
ggctcgagca ctcggcttgc t                                              21

<210> SEQ ID NO 26
<211> LENGTH: 24
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 26
cgggctgatc ctggccggca ccgt                                           24

<210> SEQ ID NO 27
<211> LENGTH: 24
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 27
gtgttctcct ggatgtacaa gtac                                           24

<210> SEQ ID NO 28
<211> LENGTH: 23
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 28
tccaaggccc gcgacgtcaa gga                                            23
```

METHODS AND COMPOSITIONS FOR EXPRESSION OF TRANSGENES IN PLANTS

BACKGROUND OF THE INVENTION

1. Field of the Invention

The present invention relates generally to transgenic plants. More specifically, it relates to a methods and compositions expressing transgenes in plants.

2. Description of the Related Art

Recent advances in molecular biology have dramatically enhanced the ability of scientists to manipulate the germplasm of animals and plants. Genes controlling specific phenotypes, for example, particular polypeptides that lend insect, antibiotic and herbicide resistance, have been located within certain germplasm and isolated from it. Even more important has been the ability to take the genes which have been isolated from one organism and to introduce them into another organism. This transformation may be accomplished even where the recipient organism is from a different phylum, genus or species from that which donated the gene (heterologous transformation).

Attempts have been made to genetically engineer desired traits into plant genomes by introduction of exogenous genes using a number of genetic engineering techniques. The uptake of new DNA by recipient plant cells has been accomplished by means including Agrobacterium infection (Nester et al., 1984), polyethylene glycol (PEG)-mediated DNA uptake (Lorz et al., 1985), electroporation of protoplasts (Fromm et al., 1986) and microprojectile bombardment (Klein et al., 1987).

While some of the aforementioned techniques have made transformation of plants nearly routine, the expression of exogenous DNA has been more troublesome. One of the most serious problems which has been encountered is a phenomenon known as "co-suppression." This term was coined to describe the inhibition of gene expression of an endogenous gene after the introduction of a homologous transgene (Jorgensen, 1990), and was first described for the chalcone synthase (CHS) gene in Petunia (Napoli et al., 1990; Van der Krol et al., 1990). Co-suppression is not unique to CHS, however, and appears to be a general phenomenon affecting transgenic plants. The degree of co-suppression varies for individual transformants, but in some plants, it may take place to such a degree that a null phenotype is produced for the loci involved.

Numerous transgenic plant systems have exhibited the phenomenon of homology-dependent "gene silencing," which can involve either multiple copies of at least partially homologous transgenes or a transgene and a homologous endogenous sequence (Jorgensen, 1995; Matzke and Matzke, 1995; Meyer, 1995). The most fundamental mechanistic feature distinguishing various cases of silencing is whether the observed inactivation occurs at the transcriptional or post-transcriptional level, and this is determined in turn by the region of homology between the interacting sequences. Transcriptional silencing occurs largely as a result of promoter homology (Neuhuber et al., 1994).

Promoter homology-dependent gene silencing interferes with transcription, and sometimes causes paramutations, leading to heritable changes in gene expression and/or DNA modifications that persist after segregation of the transgene (Lindbo et al., 1993; Jorgensen, 1995; Matzke and Matzke, 1995; Park et al., 1996). The cause of such changes in gene expression are poorly understood, but it is known that silencing is influenced by the length of the homology and by the position of the interacting sequences.

In the case of the nopaline synthase promoter, it was found that a 300 bp region of homology was sufficient to mediate co-suppression in tobacco (Matzke et al., 1993). It has also been found that an endogenous sequence known as $H_2$, which has homology to the nopaline synthase promoter, is a potent silencer of genes driven by the nopaline synthase promoter (Matzke et al., 1993; Matzke et al., 1994). This is believed to involve pairing of the nopaline synthase promoter copies at the silencing and target loci, followed by the imposition of methylation on the target copy to a degree similar to that acquired autonomously by the silencer (Matzke et al., 1994). The most efficient example of co-suppression is a tobacco line carrying a transgene insert with two genes driven by the 19S and 35S promoter of CaMV, respectively. Both genes linked to the two promoters are suppressed, and this locus trans-inactivates newly introduced constructs that provide at least 90 bp of common homology (Vaucheret, 1993).

Transcriptional silencing is particularly troublesome to agricultural biotechnologists, in that many of the most useful promoters for expression of a particular transgene are native to the host genome. This is especially true for one of agriculture's most important crops, maize. Examples of several maize promoters with desirable expression profiles include near constitutive maize promoters such as those of the Adh and sucrose synthase genes (Walker et al., 1987; Yang and Russell, 1990), tissue-specific promoters such as the maize zein and light harvesting complex promoters (Conkling et al., 1990; Simpson, 1986), and inducible promoters such as that of the corn heat shock protein (Odell et al., 1985).

There is, therefore, a great need in the art for improved methods for the expression of endogenous genes in plants, and particularly in agronomically important monocot plants such as maize. Particularly, methods are needed which allow scientists to exploit the desirable characteristics of monocot promoters, yet avoid the problems associated with co-suppression of homologous sequences. Currently technology is limited in this respect by the lack of suitable alternatives to promoters which are native to agronomically important monocot species.

SUMMARY OF THE INVENTION

Therefore, one aspect of the instant invention provides a method of expressing a gene in a monocot plant comprising the steps of (a) providing a selected gene; (b) preparing a construct comprising said gene operably linked to a Coix promoter; (c) transforming recipient monocot cells with said construct; and (d) regenerating a monocot plant which expresses said gene. In particular embodiments of the invention the monocot plant is a plant selected from the group consisting of rice, wheat, barley, rye, sorghum and maize. The step of transforming may comprise any method capable of stably transforming a plant including, for example, microprojectile bombardment, PEG mediated transformation of protoplasts, electroporation, silicon carbide fiber mediated transformation, or Agrobacterium-mediated transformation. In a preferred embodiment of the invention the step of transforming comprises microprojectile bombardment by coating microprojectiles with DNA comprising the construct and contacting the recipient cells with the microprojectiles.

The gene may be potentially any gene which one wishes to have expressed in a transgenic plant including an insect resistance gene, a disease resistance gene, a herbicide resistance gene, a gene affecting grain composition or quality, a nutrient utilization gene, a mycotoxin reduction gene, a male sterility gene, a selectable marker gene, a screenable marker gene, a negative selectable marker gene, a gene affecting plant agronomic characteristics, and an environment or stress resistance gene. In particular embodiments of the invention the promoter from Coix is a promoter from a gene selected from the group consisting of gamma zein, oleosin ole16, globulin1, actin1, actin c1, sucrose synthetase, INOPS, EMB5, globulin2, b-32, ADPG-pyrophosphorylase, Ltp1, Ltp2, oleosin ole17, oleosin ole18, actin2, pollen-specific protein, pollen-specific pectate lyase, anther-specific protein, anther-specific gene RTS2, pollen-specific gene, tapetum-specific gene, tapetum-specific gene RAB24, anthranilate synthase alpha subunit, alpha zein, anthranilate synthase beta subunit, dihydrodipicolinate synthase, Thi1, alcohol dehydrogenase, cab binding protein, H3C4, RUBISCO SS starch branching enzyme, ACCase, actin3, actin7, regulatory protein GF'14–12, ribosomal protein L9, cellulose biosynthetic enzyme, S-adenosyl-L-homocysteine hydrolase, superoxide dismutase, C-kinase receptor, phosphoglycerate mutase, root-specific RCc3 mRNA, glucose-6 phosphate isomerase, pyrophosphate-fructose 6-phosphate1phosphotransferase, ubiquitin, beta-ketoacyl-ACP synthase, 33kDa photosystem II, oxygen evolving protein, 69 kDa vacuolar ATPase subunit, metallothionein-like protein, glyceraldehyde-3-phosphate dehydrogenase, ABA- and ripening-inducible-like protein, phenylalanine ammonia lyase, adenosine triphosphatase S-adenosyl-L-homocysteine hydrolase, α-tubulin, cab, PEPCase, R, lectin, light harvesting complex, heat shock protein, chalcone synthase, zein, globulin-1, auxin-binding protein, UDP glucose flavonoid glycosyl-transferase gene, MPI, oleosin, actin, opaque 2, and b70. In one embodiment of the invention, the Coix promoter is a gamma coixin promoter.

In another aspect, the invention provides a method of producing progeny comprising the steps of (a) preparing a monocot plant according to the methods described above; and (b) crossing the plant with a second plant or with itself.

In yet another aspect, the invention provides a method of plant breeding comprising the steps of: (a) obtaining a progeny plant of any generation of a monocot plant prepared according to the methods described above, wherein the progeny plant comprises said construct; and (b) crossing the plant with itself or a second plant.

In still yet another aspect, the invention provides a method of preventing gene silencing in a monocot plant comprising the steps of: (a) identifying a Coix promoter that is homeologous to a promoter from said monocot plant; (b) cloning said Coix promoter; (c) preparing a construct comprising said Coix promoter operably linked to a selected gene; (d) transforming a recipient cell of said monocot with said construct; and (e) regenerating a plant expressing said gene from said recipient cell. The monocot plant may be potentially any monocot plant, including rice, wheat, barley, rye, sorghum and maize. In one embodiment of the invention, the monocot is maize.

The step of transforming may comprise any suitable method for introducing DNA into a plant genome, including microprojectile bombardment, PEG mediated transformation of protoplasts, electroporation, silicon carbide fiber mediated transformation, or Agrobacterium-mediated transformation. In a preferred embodiment of the invention, the step of transforming comprises microprojectile bombardment achieved by coating microprojectiles with DNA comprising said construct and contacting said recipient cells with said microprojectiles. The selected gene may include, for example, an insect resistance gene, a disease resistance gene (bacterial, viral, fIngal or nematode), a herbicide resistance gene, a gene affecting grain composition or quality, a nutrient utilization gene, a mycotoxin reduction gene, a male sterility gene, a selectable marker gene, a screenable marker gene, a negative selectable marker, a gene affecting plant agronomic characteristics, or an environment or stress resistance gene. In particular embodiment of the invention, the promoter is from a gene selected from the group consisting of gamma zein, oleosin ole16, globulin1, actin1, actin c1, sucrose synthetase, INOPS, EMB5, globulin2, b-32, ADPG-pyrophosphorylase, Ltp1, Ltp2, oleosin ole17, oleosin ole18, actin2, pollen-specific protein, pollen-specific pectate lyase, anther-specific protein, anther-specific gene RTS2, pollen-specific gene, tapetum-specific gene, tapetum-specific gene RAB24, anthranilate synthase alpha subunit, alpha zein, anthranilate synthase beta subunit, dihydrodipicolinate synthase, Thi1, alcohol dehydrogenase, cab binding protein, H3C4, RUBISCO SS starch branching enzyme, ACCase, actin3, actin7, regulatory protein GF'14–12, ribosomal protein L9, cellulose biosynthetic enzyme, S-adenosyl-L-homocysteine hydrolase, superoxide dismutase, C-kinase receptor, phosphoglycerate mutase, root-specific RCc3 mRNA, glucose-6 phosphate isomerase, pyrophosphate-fructose 6-phosphatelphosphotransferase, ubiquitin, beta-ketoacyl-ACP synthase, 33kDa photosystem II, oxygen evolving protein, 69 kDa vacuolar ATPase subunit, metallothionein-like protein, glyceraldehyde-3-phosphate dehydrogenase, ABA- and ripening-inducible-like protein, phenylalanine ammonia lyase, adenosine triphosphatase S-adenosyl-L-homocysteine hydrolase, α-tubulin, cab, PEPCase, R, lectin, light harvesting complex, heat shock protein, chalcone synthase, zein, globulin-1, ABA, auxin-binding protein, UDP glucose flavonoid glycosyl-transferase gene, MPI, oleosin, actin, opaque 2, b70, and oleosin.

In particular embodiments of the invention, the step of identifying comprises hybridization of DNA from the monocot promoter or flanking sequences thereof to DNA from Coix. The DNA from Coix may comprise a library of genomic DNA clones. In other embodiments of the invention, the step of identifying a Coix promoter comprises PCR™.

In still yet another aspect, the invention provides a method of producing progeny comprising the steps of: (a) preparing a monocot plant according to the methods described above, and (b) crossing the plant with a second plant or with itself.

In still yet another aspect, the invention provides a method of plant breeding comprising the steps of: (a) obtaining a progeny plant of any generation of a monocot plant prepared according to the methods of the invention, wherein the progeny plant comprises a construct of the invention; and (b) crossing said plant with itself or a second plant.

In still yet another aspect, the invention provides a method of preparing a maize expression vector comprising the steps of: (a) identifying a monocot promoter having a desirable expression profile; (b) isolating a Coix promoter that is homeologous to said maize promoter; and (c) constructing an expression vector comprising said Coix promoter operably linked to a selected gene. In particular embodiments of the invention, the monocot is selected from the group consisting of rice, wheat, barley, rye, sorghum and maize. In a preferred embodiment of the invention, the monocot is maize. In further embodiments of the invention, the selected gene encodes a trait selected from the group consisting of an insect resistance gene, a disease resistance gene, a herbicide resistance gene, a gene affecting grain composition or quality, a nutrient utilization gene, a mycotoxin reduction gene, a male sterility gene, a selectable marker gene, a screenable marker gene, a negative selectable marker, a gene affecting plant agronomic characteristics, and an environment or stress resistance gene.

In another embodiment of the invention, the monocot promoter is from a gene selected from the group consisting of gamma zein, oleosin ole16, globulin1, actin1, actin c1, sucrose synthetase, INOPS, EMB5, globulin2, b-32, ADPG-pyrophosphorylase, Ltp1, Ltp2, oleosin ole17, oleosin ole18, actin, pollen-specific protein, pollen-specific pectate lyase, anther-specific protein, anther-specific gene RTS2, pollen-specific gene, tapetum-specific gene, tapetum-specific gene RAB24, anthranilate synthase alpha subunit, alpha zein, anthranilate synthase beta subunit, dihydrodipicolinate synthase, Thi1, alcohol dehydrogenase, cab binding protein, H3C4, RUBISCO SS starch branching enzyme, ACCase, actin3, actin7, regulatory protein GF'14–12, ribosomal protein L9, cellulose biosynthetic enzyme, S-adenosyl-L-homocysteine hydrolase, superoxide dismutase, C-kinase receptor, phosphoglycerate mutase, root-specific RCc3 mRNA, glucose-6 phosphate isomerase, pyrophosphate-fructose 6-phosphate1phosphotransferase, ubiquitin, beta-ketoacyl-ACP synthase, 33kDa photosystem II, oxygen evolving protein, 69 kDa vacuolar ATPase subunit, metallothionein-like protein, glyceraldehyde-3-phosphate dehydrogenase, ABA- and ripening-inducible-like protein, phenylalanine ammonia lyase, adenosine triphosphatase S-adenosyl-L-homocysteine hydrolase, α-tubulin, cab, PEPCase, R, lectin, light harvesting complex, heat shock protein, chalcone synthase, zein, globulin-1, ABA, auxin-binding protein, UDP glucose flavonoid glycosyltransferase gene, MPI, oleosin, actin, opaque 2, b70, and oleosin.

The step of identifying, in one embodiment of the invention, comprises hybridization of DNA from said monocot gene or flanking sequences thereof to DNA from Coix, whereby the DNA from Coix may comprise a library of genomic DNA clones. In another embodiment of the invention, the step of identifying a Coix promoter comprises PCR™.

Still yet another aspect of the invention provides an isolated gamma coixin promoter isolatable from the nucleic acid sequence of SEQ ID NO:8. Also provided by the invention, is an isolated nucleic acid sequence comprising from about 80 to about 894 contiguous nucleotides of SEQ ID NO:8. In another embodiment of the invention, the isolated nucleic acid sequence comprises from about 222 to about 894 contiguous nucleotides of SEQ ID NO:8, and may further comprise the nucleic acid sequence of SEQ ID NO:18. The isolated nucleic acid sequence may also comprise from about 412 to about 894 contiguous nucleotides of the nucleic acid sequence of SEQ ID NO:8, and may still further comprise the nucleic acid sequence of SEQ ID NO:19.

Still yet another aspect of the invention provides an isolated DNA encoding a gamma coixin protein or peptide. In particular embodiments of the invention, the DNA segment encodes the polypeptide encoded by SEQ ID NO:16. The DNA segment may also comprise about 100 to about 603 or about 350 to about 603 contiguous nucleotides of the nucleic acid sequence of SEQ ID NO:16, or may comprise the nucleic acid sequence of SEQ ID NO:16.

Still yet another aspect of the invention provides an isolated gamma coixin terminator isolatable from the nucleic acid sequence of SEQ ID NO:11. The gamma coixin terminator may also comprise from about 80 to about 412 contiguous nucleotides of the nucleic acid sequence of SEQ ID NO:11. In further embodiments of the invention, the terminator may comprise from about 200 to about 412 or about 325 to about 412 contiguous nucleotides of the nucleic acid sequence of SEQ ID NO:11. The terminator may also comprise the nucleic acid sequence of SEQ ID NO:11.

Still yet another aspect of the invention provides a Coix oleosin 3 terminator isolatable from the nucleic acid sequence of SEQ ID NO:17. Also provided by the invention is an isolated nucleic acid sequence comprising from about 50 to about 377, about 120 to about 377, about 220 to about 377, or about 300 to about 377 contiguous nucleotides of the nucleic acid sequence of SEQ ID NO:17. In one embodiment of the invention, the nucleic acid comprises the nucleic acid sequence SEQ ID NO:17.

Still yet another aspect of the invention provides a fertile transgenic plant comprising a selected DNA, said selected DNA comprising a gamma coixin promoter. In particular embodiments of the invention, the gamma coixin promoter is isolatable from the nucleic acid sequence of SEQ ID NO:8. In other embodiments of the invention, the promoter comprises an isolated nucleic acid sequence comprising from about 80 to about 894, about 222 to about 894, or about 412 to about 894 contiguous nucleotides of SEQ ID NO:8. In still other embodiments of the invention, the promoter comprises the nucleic acid sequence of SEQ ID NO:8, SEQ ID NO:18, or SEQ ID NO:19. The promoter may be operably linked to potentially any exogenous gene, including an insect resistance gene, a disease resistance gene, a herbicide resistance gene, a gene affecting grain composition or quality, a nutrient utilization gene, a mycotoxin reduction gene, a male sterility gene, a selectable marker gene, a screenable marker gene, a negative selectable marker, a gene affecting plant agronomic characteristics, and an environment or stress resistance gene.

Still yet another aspect of the invention provides a fertile transgenic plant comprising a selected DNA, said selected DNA comprising a gene encoding gamma coixin. In particular embodiments of the invention, the gene encoding gamma coixin encodes the polypeptide encoded by SEQ ID NO:16. In still other embodiments of the invention, the gene encoding gamma coixin comprises from about 100 to about 603, or about 350 to about 603 contiguous nucleotides of the nucleic acid sequence of SEQ ID NO:16. In further embodiments of the invention, the gene encoding gamma coixin comprises the nucleic acid sequence of SEQ ID NO:16.

Still yet another aspect of the invention provides a fertile transgenic plant comprising a selected DNA, said selected DNA comprising a gamma coixin terminator. In particular embodiments of the invention, the gamma coixin terminator is isolatable from the nucleic acid sequence of SEQ ID NO:11. In other embodiments of the invention, the gamma coixin terminator comprises a nucleic acid sequence comprising from about 80 to about 412, from about 200 to about 412, or from about 325 to about 412 contiguous nucleotides of the nucleic acid sequence of SEQ ID NO:11. In further embodiments of the invention, the gamma coixin terminator comprises the nucleic acid sequence of SEQ ID NO:11.

Still yet another aspect of the invention provides a fertile transgenic plant comprising a selected DNA, said selected DNA comprising a Coix oleosin 3 terminator. In particular embodiments of the invention, the Coix oleosin 3 terminator is isolatable from the nucleic acid sequence of SEQ ID NO:17. In another embodiment of the invention, the terminator comprises from about 50 to about 377, about 120 to about 377, about 220 to about 377, or about 300 to about 377 contiguous nucleotides of the nucleic acid sequence of SEQ ID NO:17. In one embodiment of the invention, the terminator comprises the nucleic acid sequence SEQ ID NO:17.

Still yet another aspect of the invention provides a progeny plant of any generation of any of the plants described above, wherein the plant comprises said selected DNA. In particular embodiments of the invention, the plant is a monocot plant selected from the group consisting of rice, wheat, barley, rye, sorghum and maize. In one embodiment of the invention, the monocot is maize. In another embodiment of the invention, the plant is a dicot plant selected from the group consisting of tobacco, tomato, potato, soybean and cotton.

Still yet another aspect of the invention provides a method of plant breeding comprising crossing a fertile transgenic plant of the invention, or a transgenic progeny thereof which has inherited an exogenous DNA of the invention, with itself or a second plant.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 8: Sequence comparison of promoter regions of gamma-prolamine encoding genes from maize, sorghum and Coix. Nucleotides identical in three sequences are indicated by shading. The maize, Coix and sorghum promoter sequences are indicated as gamma zein (SEQ ID NO:23), gamma coixin (SEQ ID NO:8) and gamma kafirin (SEQ ID NO:22), respectively.

DETAILED DESCRIPTION OF THE INVENTION

Figure 1:
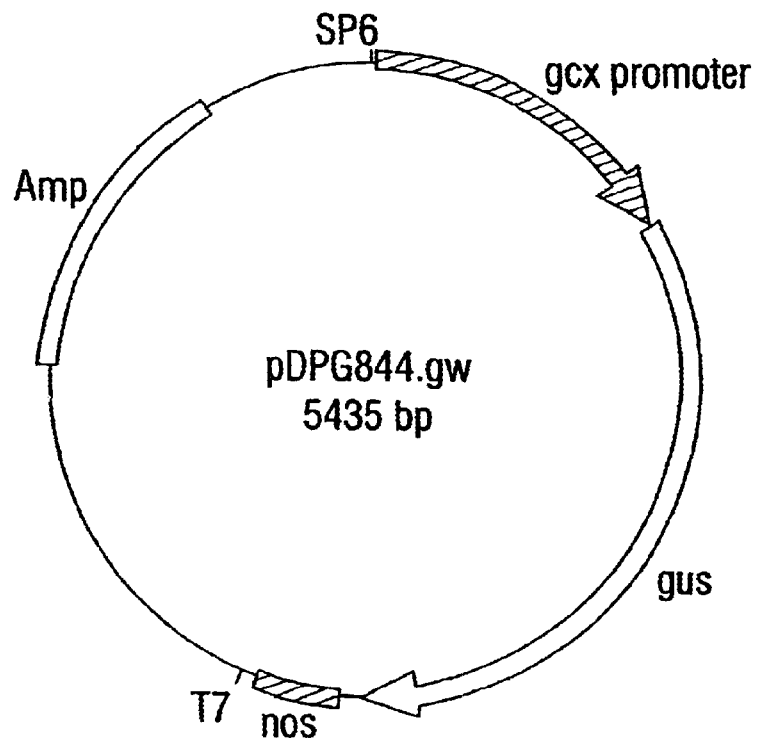
FIG. 1: Map of plasmid pDPG844. The plasmid contains an expression cassette comprised of an 894 bp promoter from the gamma coixin gene (SEQ ID NO:8), the coding sequence of the GUS reporter gene and the nos terminator.

The current invention overcomes deficiencies in the prior art by providing methods for ransgene expression which eliminate or decrease gene silencing. The present invention is significant in that it provides promoters for the expression of exogenous genes in monocots which have similar expression profiles to those of the host genome, yet which are dissimilar enough in sequence to limit gene-silencing. In particular embodiments of the invention, the promoters provided by the invention are from the genus Coix. Promoters derived from Coix will be especially useful in maize, as well as other monocots, such as wheat, rice, barley, rye, sorghum and sugar cane, as well as in dicot species.

The phenomenon of gene-silencing, which has also been referred to as co-suppression, sense suppression, and sense co-suppression, is the decrease or elimination of gene expression upon the introduction of sequences having native homologous copies (Napoli et al., 1990; Van der Krol et al., 1990). Gene silencing, can act at regulatory and/or coding regions of a transgene, and is frequently associated with methylation of the silenced region. In the field of agricultural biotechnology, silencing of regulatory regions is especially problematic in that many endogenous promoters have particularly useful characteristics for transgene expression.

It is specifically contemplated by the inventors that utility of the current invention may be extended to the creation of expression vectors comprising elements from Coix in addition to promoters. In particular, it is contemplated that avoidance of gene-silencing and other problems associated with homology between transgene elements and native sequences may be avoided by use of Coix sequences in transgenes expressed in monocots other than Coix. For example, coding regions homeologous to maize genes could be efficiently expressed in maize, whereas the native maize gene would be silenced. Also deemed especially useful are enhancer elements and terminators from Coix.

I. Promoters for Use With the Invention

The current invention encompasses the use of promoters from the genus Coix for expression of an exogenous gene in monocots such as maize. Such promoters may be isolated de novo from Coix, or alternatively, may be isolated based on genetic information from known monocot promoters. A particularly efficient means contemplated by the inventor for identification of Coix promoters comprises using primers or probes derived from maize genes or promoters to isolate homeologous sequences from Coix.

(i) Exemplary Promoters

Useful promoters include those that are inducible, viral, synthetic, constitutive as described (Poszkowski et al., 1989;

Odell et al., 1985), temporally regulated, spatially regulated, and spatio-temporally regulated (Chau et al., 1989). A promoter is selected for its ability to direct the transformed plant cell's or transgenic plant's transcriptional activity to the coding region. Some examples of maize sequences deemed especially useful for the isolation of Coix promoters include those of the Adh (Walker et al., 1987; Paul and Ferl, 1991; Genbank Accession No. S45022), sucrose synthase (Yang & Russell, 1990), cab (Sullivan et al., 1989, Genbank Accession No. X14794), PEPCase (Hudspeth & Grula, 1989; Yanagisawa and Izui, 1989, Genbank Accession Nos. X14579, X14581, X14580) and R gene complex-associated genes (Chandler et al., 1989; Consonni et al., 1993, Genbank Accession No. X67619; Radicella et al., 1991, Genbank Accession Nos. X57276, S48027). Sequences from other monocots, for example, the rice actin promoter (Genbank Accession No. S44221), may also be useful.

Exemplary genes for isolation of tissue-specific promoters are corn sucrose synthetase 1 (Yang et al., 1990), corn alcohol dehydrogenase 1 (Vogel et al., 1989; Dennis et al., 1984, Genbank Accession Nos. X04049, X00581); corn light harvesting complex (Simpson, 1986; Bansal et al., 1992, Genbank Accession No. M87020;), corn heat shock protein (Odell et al., 1985; Rochester et al., 1986, Genbank Accession No. X03714), maize zein (Reina et al., 1990, Genbank Accession No. X53514; Kriz et al., 1987, Genbank Accession No. X0591 1; Wandelt and Feix, 1989; Genbank Accession No. X14334; Langridge and Feix, 1983, Genbank Accession No. K00543; Reina et al., 1990, Genbank Accession No. X53515), globulin-1 (Belanger and Kriz et al., 1991; Genbank Accession Nos. L22344, L22295), and chalcone synthase genes (Franken et al., 1991;. Genbank Accession No. X60204).

Other similar known maize sequences include root cell promoters (Conkling et al., 1990), and tissue specific enhancers (Fromm et al., 1989). Examples of inducible promoters include ABA- and turgor-inducible promoters and the promoter of the auxin-binding protein gene (Scwob et al., 1993; Genbank Accession No. L08425). Still other known maize sequences which one may use to isolate heterologous promoters include the UDP glucose flavonoid glycosyl-transferase gene (Ralston et al., 1988; Genbank Accession Nos. X07940; Y00616); MPI proteinase inhibitor gene (Cordero et al., 1994; Genbank Accession No. X78988), glyceraldehyde-3-phosphate dehydrogenase gene (Genbank Accession No. U45859; Kohler et al., 1995, Genbank Accession No. L40803; Quigley et al., 1989, Genbank Accession No. X15408; Martinez et al., 1989, Genbank Accession No. X15596), as well as those of chloroplast genes (Genbank Accession No. X86563).

Exemplary genetic elements specifically contemplated by the current inventors for the isolation of Coix sequences for expression in maize and other monocots are listed below, in Table 1. A number of these elements have been used by the current inventors for the preparation of expression vectors, as indicated below.

TABLE 1

Exemplary sequences for the isolation of Coix genetic elements.

| Gene | Organism | Genbank Accession | Coix Genbank Accession |
|---|---|---|---|
| gamma zein[a,c,d] | maize | M16218 | X59850 |
| oleosin ole16[a] | maize | U13701 | |
| globulin1[a] | maize | X59083 | |
| actin rac1[a,b] | rice | X15865 | |
| sucrose synthetase[b] | maize | X02382 | |
| INOPS | maize | AF056326 | |
| EMB5 | maize | M90554 | |
| globulin2 | maize | X53715 | |
| ADPG-pyrophosphorylase | maize | M81603 | |
| b-32[a] | maize | X07987 | |
| Ltp1 | barley | X60292 | |
| Ltp2 | barley | X57270 | |
| oleosin ole17 | maize | U13702 | |
| oleosin ole18 | maize | J05212 | |
| actin rac2 | rice | X15864 | |
| pollen-specific protein | maize | S44171 | |
| pollen-specific pectate lyase | maize | L20140 | |
| anther-specific protein | rice | D21159 | |
| anther-specific gene RTS2 | rice | U12171 | |
| pollen-specific gene | rice | Z16402 | |
| pollen-specific gene | rice | U31771 | |
| tapetum-specific gene | rice | D21159 | |
| tapetum-specific gene | rice | D21160 | |
| RAB24 | rice | D63917 | |
| alpha zein[a] | maize | X05911 | X63113 |
| anthranilate synthase (alpha subunit)[a] | maize | (PCT Patent Application WO 97/26366) | |
| anthranilate synthase (beta subunit) | maize | M95067 | |
| dihydrodipicolinate synthase | maize | X52850 | X61730 |
| thiamine biosynthetic enzyme (Thi1) | maize | U17350 U17351 | |
| alcohol dehydrogenase[a,b] | maize | X04049 | |
| cab binding protein | maize | X53398 | |
| histone (H3C4)[a] | maize | M13379 | |
| RUBISCO SS | maize | Y09214 | |
| starch branching enzyme | maize | U17897, U65948 | |
| ACCase | maize | A25272 | |
| actin rac3 | rice | X15862 | |
| actin rac7 | rice | X15863 | |
| cellulose biosynthetic enzyme | rice | AF030052 | |
| regulatory protein GF14-12 | maize | M96856 | |
| ribosomal protein L9 | rice | D83527 | |
| S-adenosyl-L-homocysteine hydrolase | wheat | L11872 | |
| superoxide dismutase | maize | X17564 | |
| C-kinase receptor | rice | D38231 | |
| phosphoglycerate mutase | maize | Z33612 | |
| root-specific RCc3 mRNA | rice | L27208 | |
| glucose-6 phosphate isomerase | maize | U17225 | |
| pyrophos.-fructose 6-phosphate1phosphotransferase | rice | D21294 | |
| ubiquitin | maize | U29162 | |
| beta-ketoacyl-ACP synthase | barley | Z34269 | |
| 33kDa photosystem II oxygen evolving protein | wheat | X57408 | |
| 69 kDa vacuolar ATPase subunit | maize | U36436 | |
| metallothionein-like protein | maize | I15488 | |
| glyceraldehyde-3-phosph. dehydrogenase | maize | M18976 | |
| ABA- and ripening-inducible-like protein | maize | U09276 | |
| phenylalanine ammonia lyase | maize | M95077 | |
| adenosine triphosphatase | barley | Z33632 | |
| S-adenosyl-L-homocysteine hydrolase | wheat | L11872 | |

[a]promoter indicated has been used for transformation of maize.
[b]intron enhancer indicated has been used for transformation of maize.
[c]Coix promoter has been isolated and used for transformation of maize.
[d]Coix protein coding sequence (CDS) has been isolated and used for transformation of maize.

(ii) Cloning Homeologous Sequences from Coix

Part of the current invention involves isolating regulatory regions from the genus Coix by the use of probes or primers derived from maize genes or flanking sequences thereof. The probes or primers may be directly composed of cloned maize DNA, or alternatively, may be synthetically prepared based on DNA sequence data. Additionally, promoters may be isolated using sequences which are derived from a species other than maize, but which is still closely related to maize and Coix. Other species deemed particularly usefuil for identification of heterologous promoters in Coix include monocotyledonous plants such as rye, wheat, barley, oats, sorghum, rice, and sugarcane.

The term primer, as defined herein, is meant to encompass any nucleic acid that is capable of priming the synthesis of a nascent nucleic acid in a template-dependent process. Typically, primers are oligonucleotides from ten to twenty base pairs in length, but longer sequences can be employed. Primers may be provided in double-stranded or single-stranded form, although the single-stranded form is preferred. Probes are defined differently, although they may act as primers. Probes, while perhaps capable of priming, are designed to binding to the target DNA or RNA and need not be used in an amplification process.

In preferred embodiments, the probes or primers are labeled with radioactive species ($^{32}P$, $^{14}C$, $^{35}S$, $^{3}H$, or other label), with a fluorophore (rhodamine, fluorescein), an antigen (biotin, streptavidin, digoxigenin), or a chemiluminescent agent (luciferase) or direct conjugation with enzymes (alkaline phosphatase).

Following preparation of probes or primers, the first step in cloning of heterologous promoters typically involves preparing and screening of an appropriate library of clones, such as, in the present case, a genomic DNA library from Coix. The screening may be based on the hybridization of oligonucleotide probes, designed from a consideration of portions of the maize promoter sequence, or from the DNA sequences of the gene or related genes. The operation of such screening protocols are well known to those of skill in the art and are described in detail below and in the scientific literature, for example, in Sambrook et al. (1989), specifically incorporated herein by reference in its entirety.

1. Template Dependent Amplification

Template dependent amplification methods, for example PCR, represent one efficient means for isolation of maize-homeologous or other sequences from Coix. In particular, primers may be designed, based on genetic information from homeologous sequences, which can be used for the template dependent amplification of nucleic acids comprising Coix promoters. A number of template dependent processes are available to amplify sequences present in a given template sample. One of the best known amplification methods is the polymerase chain reaction (referred to as PCR™) which is described in detail in U.S. Pat. No. 4,683,195; U.S. Pat. No. 4,683,202; and U.S. Pat. No. 4,800,159, each of which is incorporated herein by reference in its entirety.

Briefly, in PCR™, two primer sequences are prepared that are complementary to regions on opposite complementary strands of the marker sequence. An excess of deoxynucleoside triphosphates are added to a reaction mixture along with a DNA polymerase, e.g., Taq polymerase. If the marker sequence is present in a sample, the primers will bind to the marker and the polymerase will cause the primers to be extended along the marker sequence by adding on nucleotides. By raising and lowering the temperature of the reaction mixture, the extended primers will dissociate from the marker to form reaction products, excess primers will bind to the marker and to the reaction products and the process is repeated.

A reverse transcriptase PCR™ amplification procedure may be performed in order to quantify the amount of mRNA amplified. Methods of reverse transcribing RNA into cDNA are well known and described in Sambrook et al. (1989). Alternative methods for reverse transcription utilize thermostable, RNA-dependent DNA polymerases. These methods are described in PCT/WO90/07641 filed Dec. 21, 1990. Polymerase chain reaction methodologies are well known in the art.

Another method for amplification is the ligase chain reaction ("LCR"), disclosed in EP 0 320 308, incorporated herein by reference in its entirety. In LCR, two complementary probe pairs are prepared, and in the presence of the target sequence, each pair will bind to opposite complementary strands of the target such that they abut. In the presence of a ligase, the two probe pairs will link to form a single unit. By temperature cycling, as in PCR™, bound ligated units dissociate from the target and then serve as "target sequences" for ligation of excess probe pairs. U.S. Pat. No. 4,883,750 describes a method similar to LCR for binding probe pairs to a target sequence.

Qbeta Replicase, described in PCT/US87/00880, may also be used as still another amplification method in the present invention. In this method, a replicative sequence of RNA that has a region complementary to that of a target is added to a sample in the presence of an RNA polymerase. The polymerase will copy the replicative sequence that can then be detected.

An isothermal amplification method, in which restriction endonucleases and ligases are used to achieve the amplification of target molecules that contain nucleotide 5'-[α-thio]-triphosphates in one strand of a restriction site may also be useful in the amplification of nucleic acids in the present invention (Walker et al., 1992).

Strand Displacement Amplification (SDA) is another method of carrying out isothermal amplification of nucleic acids which involves multiple rounds of strand displacement and synthesis, i.e., nick translation. A similar method, called Repair Chain Reaction (RCR), involves annealing several probes throughout a region targeted for amplification, followed by a repair reaction in which only two of the four bases are present. The other two bases can be added as biotinylated derivatives for easy detection. A similar approach is used in SDA. Target specific sequences can also be detected using a cyclic probe reaction (CPR). In CPR, a probe having 3' and 5' sequences of non-specific DNA and a middle sequence of specific RNA is hybridized to DNA that is present in a sample. Upon hybridization, the reaction is treated with RNase H, and the products of the probe identified as distinctive products that are released after digestion. The original template is annealed to another cycling probe and the reaction is repeated.

Still another amplification methods described in GB 2 202 328, and in PCT/US89/01025, each of which is incorporated herein by reference in its entirety, may be used in accordance with the present invention. In the former application, "modified" primers are used in a PCR™-like, template- and enzyme-dependent synthesis. The primers may be modified by labeling with a capture moiety (e.g., biotin) and/or a detector moiety (e.g., enzyme). In the latter application, an excess of labeled probes are added to a sample. In the presence of the target sequence, the probe binds and is cleaved catalytically. After cleavage, the target sequence is released intact to be bound by excess probe. Cleavage of the labeled probe signals the presence of the target sequence.

Other nucleic acid amplification procedures include transcription-based amplification systems (TAS), including nucleic acid sequence based amplification (NASBA) and 3SR (Kwoh et al., 1989; Gingeras et al.; PCT/WO88/10315; incorporated herein by reference in their entirety). In NASBA, the nucleic acids can be prepared for amplification by standard phenol/chloroform extraction, heat denaturation of a clinical sample, treatment with lysis buffer and minispin columns for isolation of DNA and RNA or guanidinium chloride extraction of RNA. These amplification techniques involve annealing a primer which has target specific sequences. Following polymerization, DNA/RNA hybrids are digested with RNase H while double stranded DNA molecules are heat denatured again. In either case the single stranded DNA is made fully double stranded by addition of second target specific primer, followed by polymerization. The double-stranded DNA molecules are then multiply transcribed by an RNA polymerase such as T7 or SP6. In an isothermal cyclic reaction, the RNA's are reverse transcribed into single stranded DNA, which is then converted to double stranded DNA, and then transcribed once again with an RNA polymerase such as T7 or SP6. The resulting products, whether truncated or complete, indicate target specific sequences.

EP 0 329 822 (incorporated herein by reference in its entirety) disclose a nucleic acid amplification process involving cyclically synthesizing single-stranded RNA ("ssRNA"), ssDNA, and double-stranded DNA (dsDNA), which may be used in accordance with the present invention. The ssRNA is a template for a first primer oligonucleotide, which is elongated by reverse transcriptase (RNA-dependent DNA polymerase). The RNA is then removed from the resulting DNA:RNA duplex by the action of ribonuclease H (RNase H, an RNase specific for RNA in duplex with either DNA or RNA). The resultant ssDNA is a template for a second primer, which also includes the sequences of an RNA polymerase promoter (exemplified by T7 RNA polymerase) 5' to its homology to the template. This primer is then extended by DNA polymerase (exemplified by the large "Klenow" fragment of E. coli DNA polymerase I), resulting in a double-stranded DNA ("dsDNA") molecule, having a sequence identical to that of the original RNA between the primers and having additionally, at one end, a promoter sequence. This promoter sequence can be used by the appropriate RNA polymerase to make many RNA copies of the DNA. These copies can then re-enter the cycle leading to very swift amplification. With proper choice of enzymes, this amplification can be done isothermally without addition of enzymes at each cycle. Because of the cyclical nature of this process, the starting sequence can be chosen to be in the form of either DNA or RNA.

PCT/WO89/06700 (incorporated herein by reference in its entirety) disclose a nucleic acid sequence amplification scheme based on the hybridization of a promoter/primer sequence to a target single-stranded DNA ("ssDNA") followed by transcription of many RNA copies of the sequence. This scheme is not cyclic, i.e., new templates are not produced from the resultant NA transcripts. Other amplification methods include "RACE" and "one-sided PCR™" Frohman, 1990; Ohara et al., 1989; each herein incorporated by reference in their entirety).

Methods based on ligation of two (or more) oligonucleotides in the presence of nucleic acid having the sequence of the resulting "di-oligonucleotide," thereby amplifying the di-oligonucleotide, may also be used in the amplification step of the present invention (Wu et al., 1989, incorporated herein by reference in its entirety).

Following amplification, it normally is desirable, at one stage or another, to separate the amplification product from the template and the excess primer for the purpose of determining whether specific amplification has occurred. In one embodiment, amplification products are separated by agarose, agarose-acrylamide or polyacrylamide gel electrophoresis using standard methods (Sambrook et al., 1989).

Alternatively, chromatographic techniques may be employed to effect separation. There are many kinds of chromatography which may be used in the present invention: adsorption, partition, ion-exchange and molecular sieve, and many specialized techniques for using them including column, paper, thin-layer and gas chromatography (Freifelder, 1982).

Products may be visualized in order to confirm amplification of the marker sequences. One typical visualization method involves staining of a gel with ethidium bromide and visualization under UV light. Alternatively, if the amplification products are integrally labeled with radio- or fluorometrically-labeled nucleotides, the amplification products can then be exposed to x-ray film or visualized under the appropriate stimulating spectra, following separation.

In one embodiment, visualization is achieved indirectly. Following separation of amplification products, a labeled nucleic acid probe is brought into contact with the amplified marker sequence. The probe preferably is conjugated to a chromophore but may be radiolabeled.

In another embodiment, the probe is conjugated to a binding partner, such as an antibody or biotin, and the other member of the binding pair carries a detectable moiety.

In another embodiment, detection is by a labeled probe. The techniques involved are well known to those of skill in the art and can be found in many standard books on molecular protocols (Sambrook et al., 1989). For example, chromophore or radiolabeled probes or primers identify the target during or following amplification.

One example of the foregoing is described in U.S. Pat. No. 5,279,721, incorporated by reference herein, which discloses an apparatus and method for the automated electrophoresis and transfer of nucleic acids. The apparatus permits electrophoresis and blotting without external manipulation of the gel and is ideally suited to carrying out methods according to the present invention.

In addition, the amplification products described above may be subjected to sequence analysis to identify specific kinds of variations using standard sequence analysis techniques. Within certain methods, exhaustive analysis of genes is carried out by sequence analysis using primer sets designed for optimal sequencing (Pignon et al., 1994). The present invention provides methods by which any or all of these types of analyses may be used.

2. Southern/Northern Blotting

Blotting techniques represent other methods which are well known to those of skill in the art and may be employed for the identification of nucleic acids in accordance with the current invention. Southern blotting, for example, can be used to isolate a segment of DNA containing a candidate Coix promoter useful in the expression of maize genes. In particular, through hybridization of a cDNA probe from maize to genomic DNA clones of a Coix plant one could isolate clones which include the promoter region of the corresponding gene. Alternatively, the sequence of a promoter itself could be used as a probe to directly identify homeologous Coix promoters.

Southern blotting involves the use of DNA as a target, whereas Northern blotting involves the use of RNA as a target. Each provide different types of information, although cDNA blotting is analogous, in many aspects, to blotting or RNA species. Briefly, a probe is used to target a DNA or RNA species that has been immobilized on a suitable matrix, often a filter of nitrocellulose. The different species should be spatially separated to facilitate analysis. This often is accomplished by gel electrophoresis of nucleic acid species followed by "blotting" on to the filter.

Subsequently, the blotted target is incubated with a probe (usually labeled) under conditions that promote denaturation and rehybridization. Because the probe is designed to base pair with the target, the probe will bind a portion of the target sequence under renaturing conditions. Unbound probe is then removed, and detection is accomplished as described above.

3. Chip Technologies

Specifically contemplated by the present inventor are chip-based DNA technologies such as those described by Hacia et al. (1996) and Shoemaker et al. (1996). Briefly, these techniques involve quantitative methods for analyzing large numbers of genes rapidly and accurately. By tagging genes with oligonucleotides or using fixed probe arrays, one can employ chip technology to segregate target molecules as high density arrays and screen these molecules on the basis of hybridization (Pease et al., 1994; Fodor et al., 1991).

(iii) De Novo Isolation of Coix Promoters

The current invention contemplates the use of Coix promoters which have been isolated without the use of probes or primers derived from the promoters of other species. Means for the cloning of promoters and their construction into suitable vectors for the transformation and expression of exogenous genes in maize is known in the art and disclosed in, for example, Sambrook et al., 1989, specifically incorporated herein by reference in its entirety. Types of Coix promoters deemed to be especially useful for transgene expression in maize are those that are expressed at high levels in a constitutive or non-constitutive manner. Desirable non-constitutive promoters include those that are expressed in a tissue and/or temporally specific manner, or are inducible. By temporally specific, it is meant a promoter which directs expression at one or more specific developmental periods.

A typical first step in the cloning of a promoter comprises identification of a target gene which is expressed in the desired manner, i.e., constitutively or tissue/temporally specific. An efficient means for this will comprise the preparation of a cDNA library from one or more identified target tissues, and identification of high-copy clones therein. Particularly advantageous will be cDNA clones which are highly represented, yet for which the number of gene copies is low. The cDNA clone is then used to isolate genomic DNA comprising the 5' regions flanking the coding sequence, including the promoter region, using standard library screening techniques known to those of skill in the art (see Sambrook et al., 1989).

A preferred method for the cloning of promoters is the use of the "suppression PCR" technique, described in, for example, Siebert et al., 1995, the disclosure of which is specifically incorporated herein by reference in its entirety. This method allows the PCR-amplification of uncloned and unknown sequences as long as a gene specific anchor sequence is known. Using this technique, a known sequence, such as a homologous or homeologous cDNA sequence, can be used to clone flanking regulatory elements including promoters, enhancers or terminators.

1. Quantitation of Gene Expression with Relative Quantitative RT-PCR™

Reverse transcription (RT) of RNA to cDNA followed by relative quantitative PCR™ (RT-PCR™) can be used to determine the relative concentrations of specific mRNA species isolated from plants. By determining that the concentration of a specific mRNA species varies, it is shown that the gene encoding the specific mRNA species is differentially expressed. In this way, candidate promoters can be rapidly identified and screened from Coix for use in the construction of expression vectors for maize transformation.

In PCR™, the number of molecules of the amplified target DNA increase by a factor approaching two with every cycle of the reaction until some reagent becomes limiting. Thereafter, the rate of amplification becomes increasingly diminished until there is no increase in the amplified target between cycles. If a graph is plotted in which the cycle number is on the X axis and the log of the concentration of the amplified target DNA is on the Y axis, a curved line of characteristic shape is formed by connecting the plotted points. Beginning with the first cycle, the slope of the line is positive and constant. This is said to be the linear portion of the curve. After a reagent becomes limiting, the slope of the line begins to decrease and eventually becomes zero. At this point the concentration of the amplified target DNA becomes asymptotic to some fixed value. This is said to be the plateau portion of the curve.

The concentration of the target DNA in the linear portion of the PCR™ amplification is directly proportional to the starting concentration of the target before the reaction began. By determining the concentration of the amplified products of the target DNA in PCR™ reactions that have completed the same number of cycles and are in their linear ranges, it is possible to determine the relative concentrations of the specific target sequence in the original DNA mixture. If the DNA mixtures are cDNAs synthesized from RNAs isolated from different tissues or cells, the relative abundances of the specific mRNA from which the target sequence was derived can be determined for the respective tissues or cells. This direct proportionality between the concentration of the PCR™ products and the relative mRNA abundances is only true in the linear range of the PCR™ reaction.

The final concentration of the target DNA in the plateau portion of the curve is determined by the availability of reagents in the reaction mix and is independent of the original concentration of target DNA. Therefore, the first condition that must be met before the relative abundances of a mRNA species can be determined by RT-PCR™ for a collection of RNA populations is that the concentrations of the amplified PCR™ products must be sampled when the PCR™ reactions are in the linear portion of their curves.

The second condition that must be met for an RT-PCR™ study to successfully determine the relative abundances of a particular mRNA species is that relative concentrations of the amplifiable cDNAs must be normalized to some independent standard. The goal of an RT-PCR™ study is to determine the abundance of a particular mRNA species relative to the average abundance of all mRNA species in the sample.

Most protocols for competitive PCR™ utilize internal PCR™ standards that are approximately as abundant as the target. These strategies are effective if the products of the PCR™ amplifications are sampled during their linear phases. If the products are sampled when the reactions are approaching the plateau phase, then the less abundant product becomes relatively over represented. Comparisons of relative abundances made for many different RNA samples, such as is the case when examining RNA samples for differential expression, become distorted in such a way as to make differences in relative abundances of RNAs appear less than they actually are. This is not a significant problem if the internal standard is much more abundant than the target. If the internal standard is more abundant than the target, then direct linear comparisons can be made between RNA samples.

The above discussion describes theoretical considerations for an RT-PCR™ assay for plant tissue. The problems inherent in plant tissue samples are that they are of variable quantity (making normalization problematic), and that they are of variable quality (necessitating the co-amplification of a reliable internal control, preferably of larger size than the target). Both of these problems are overcome if the RT-PCR™ is performed as a relative quantitative RT-PCR™ with an internal standard in which the internal standard is an amplifiable cDNA fragment that is larger than the target cDNA fragment and in which the abundance of the mRNA encoding the internal standard is roughly 5–100 fold higher than the mRNA encoding the target. This assay measures relative abundance, not absolute abundance of the respective mRNA species.

Other studies may be performed using a more conventional relative quantitative RT-PCR™ assay with an external standard protocol. These assays sample the PCR™ products in the linear portion of their amplification curves. The number of PCR™ cycles that are optimal for sampling must be empirically determined for each target cDNA fragment. In addition, the reverse transcriptase products of each RNA population isolated from the various tissue samples must be carefully normalized for equal concentrations of amplifiable cDNAs. This consideration is very important since the assay measures absolute mRNA abundance. Absolute mRNA abundance can be used as a measure of differential gene expression only in normalized samples. While empirical determination of the linear range of the amplification curve and normalization of cDNA preparations are tedious and time consuming processes, the resulting RT-PCR™ assays can be superior to those derived from the relative quantitative RT-PCR™ assay with an internal standard.

One reason for this advantage is that without the internal standard/competitor, all of the reagents can be converted into a single PCR™ product in the linear range of the amplification curve, thus increasing the sensitivity of the assay. Another reason is that with only one PCR™ product, display of the product on an electrophoretic gel or another display method becomes less complex, has less background and is easier to interpret.

2. Non-targeted Promoter Isolation

As well as cloning promoters in a targeted, specific manner by first identifying a gene with a desired expression profile, one could clone Coix promoters utilizing a "shotgun" screening strategy. For example, one could generate a large number of vectors comprising a selectable or screenable marker gene linked to random segments of Coix DNA. Such vectors could be prepared by mixing and ligating portions of restriction digested marker gene DNA and Coix total genomic DNA, and cloning the DNA into a suitable vector. Alternatively, one could use a "headless horseman" construct in which a cloning site directly precedes a marker gene otherwise lacking a promoter. In this case, the marker gene will only be expressed when a promoter is cloned into cloning site. Once constructed, the vectors can be used to transform a large number of maize sells. By selection for transformants expressing the marker gene, one will identify novel Coix promoters capable of directing expression in maize.

(iv) Assays of Promoters

Once cloned, the identity and/or utility of the promoter can be confirmed by sequencing, and/or expression assays.

For plants, the expression assay may comprise a system utilizing embryogenic or non-embryogenic cells, or alternatively, whole plants. An advantage of using cellular assays is that regeneration of large numbers of plants is not required, however, the systems are limited in that promoter activity in the non-regenerated cells may not directly correlate with expression in a plant. Additionally, assays of tissue or developmental specific promoters are generally not feasible.

The biological sample to be assayed may comprise nucleic acids isolated from the cells of any plant material according to standard methodologies (Sambrook et al., 1989). The nucleic acid may be genomic DNA or fractionated or whole cell RNA. Where RNA is used, it may be desired to convert the RNA to a complementary DNA. In one embodiment, the RNA is whole cell RNA; in another, it is poly-A RNA. Normally, the nucleic acid is amplified.

Depending on the format, the specific nucleic acid of interest is identified in the sample directly using amplification or with a second, known nucleic acid following amplification. Next, the identified product is detected. In certain applications, the detection may be performed by visual means (e.g., ethidium bromide staining of a gel). Alternatively, the detection may involve indirect identification of the product via chemiluminescence, radioactive scintigraphy of radiolabel or fluorescent label or even via a system using electrical or thermal impulse signals (Affymax Technology; Bellus, 1994).

Following detection, one may compare the results seen in a given plant with a statistically significant reference group of non-transformed control plants. Typically, the non-transformed control plants will be of a genetic background similar to the transformed plants. In this way, it is possible to detect differences in the amount or kind of protein detected in various transformed plants. Alternatively, clonal cultures of cells, for example, callus or an immature embryo, may be compared to other cells samples.

As indicated, variety of different assays are contemplated in the screening of cells or plants of the current invention and associated promoters. These techniques may in cases be used to detect for both the presence and expression of the particular genes as well as rearrangements that may have occurred in the gene construct. The techniques include but are not limited to, fluorescent in situ hybridization (FISH), direct DNA sequencing, pulsed field gel electrophoresis (PFGE) analysis, Southern or Northern blotting, single-stranded conformation analysis (SSCA), RNAse protection assay, allele-specific oligonucleotide (ASO), dot blot analysis, denaturing gradient gel electrophoresis, RFLP and PCR™-SSCP Where a clone comprising a promoter has been isolated in accordance with the instant invention, it is contemplated that one may wish to delimit the essential promoter regions within the clone. An efficient means for this comprises deletion analysis. In deletion analysis, a series of constructs are prepared, each containing a different portion of the clone (a subclone), and these constructs are then screened for promoter activity. A suitable means for screening for activity is to attach the deleted promoter constructs to a selectable or screenable marker, and to isolate only those cells expressing the marker gene. In this way, a number of different, deleted promoter constructs are identified which still retain the promoter activity. The smallest segment which is required for promoter activity is thereby identified through comparison of the selected constructs. This segment may then be used for the construction of vectors for the expression of exogenous genes.

II. Methods for Preparing Mutagenized Promoters

It is specifically contemplated by the inventor that one could mutagenize a Coix promoter to potentially improve the utility of the promoter for the expression of transgenes in maize. The mutagenesis of Coix promoters could be carried out at random and the mutagenized promoters screened for utility in a trial-by-error procedure. Alternatively, particular sequences which provide a Coix promoter with desirable expression characteristics could be identified and these or similar sequences introduced into maize promoters via mutation. In addition to maize, promoters from other species could be mutagenized to provide them with the desirable characteristics of a Coix promoter. For example, one could mutagenize a promoter from rice, oats, sorghum, barley, or wheat to provide the mutagenized promoter with enhanced utility for transgene expression in maize.

The means for mutagenizing a DNA segment encoding a promoter of the current invention are well-known to those of skill in the art. Modifications to such promoter regions may be made by random, or site-specific mutagenesis procedures. The promoter region may be modified by altering its structure through the addition or deletion of one or more nucleotides from the sequence which encodes the corresponding un-modified promoter region.

Mutagenesis may be performed in accordance with any of the techniques known in the art such as and not limited to synthesizing an oligonucleotide having one or more mutations within the sequence of a particular promoter region. In particular, site-specific mutagenesis is a technique useful in the preparation of promoter mutants, through specific mutagenesis of the underlying DNA. The technique further provides a ready ability to prepare and test sequence variants, for example, incorporating one or more of the foregoing considerations, by introducing one or more nucleotide sequence changes into the DNA. Site-specific mutagenesis allows the production of mutants through the use of specific oligonucleotide sequences which encode the DNA sequence of the desired mutation, as well as a sufficient number of adjacent nucleotides, to provide a primer sequence of sufficient size and sequence complexity to form a stable duplex on both sides of the deletion junction being traversed. Typically, a primer of about 17 to about 75 nucleotides or more in length is preferred, with about 10 to about 25 or more residues on both sides of the junction of the sequence being altered.

In general, the technique of site-specific mutagenesis is well known in the art, as exemplified by various publications. As will be appreciated, the technique typically employs a phage vector which exists in both a single stranded and double stranded form. Typical vectors useful in site-directed mutagenesis include vectors such as the M13 phage. These phage are readily commercially available and their use is generally well known to those skilled in the art. Double stranded plasmids are also routinely employed in site directed mutagenesis which eliminates the step of transferring the gene of interest from a plasmid to a phage.

In general, site-directed mutagenesis in accordance herewith is performed by first obtaining a single-stranded vector or melting apart of two strands of a double stranded vector which includes within its sequence a DNA sequence which encodes the desired promoter region or peptide. An oligonucleotide primer bearing the desired mutated sequence is prepared, generally synthetically. This primer is then annealed with the single-stranded vector, and subjected to DNA polymerizing enzymes such as *E. Coli* polymerase 1 Klenow fragment, in order to complete the synthesis of the mutation-bearing strand. Thus, a heteroduplex is formed wherein one strand encodes the original non-mutated sequence and the second strand bears the desired mutation. This heteroduplex vector is then used to transform or transfect appropriate cells, such as maize cells, and cells are selected which include recombinant vectors bearing the mutated sequence arrangement. A genetic selection scheme was devised by Kunkel et al. (1987) to enrich for clones incorporating the mutagenic oligonucleotide. Alternatively, the use of PCR™ with commercially available thermostable enzymes such as Taq polymerase may be used to incorporate a mutagenic oligonucleotide primer into an amplified DNA fragment that can then be cloned into an appropriate cloning or expression vector. The PCR™-mediated mutagenesis procedures of Tomic et al. (1990) and Upender et al (1995) provide two examples of such protocols. A PCR™ employing a thermostable ligase in addition to a thermostable polymerase may also be used to incorporate a phosphorylated mutagenic oligonucleotide into an amplified DNA fragment that may then be cloned into an appropriate cloning or expression vector. The mutagenesis procedure described by Michael (1994) provides an example of one such protocol.

The preparation of sequence variants of the selected promoter-encoding DNA segments using site-directed mutagenesis is provided as a means of producing potentially useful species and is not meant to be limiting as there are other ways in which sequence variants of DNA sequences may be obtained. For example, recombinant vectors encoding the desired promoter sequence may be treated with mutagenic agents, such as hydroxylamine, to obtain sequence variants.

As used herein, the term "oligonucleotide directed mutagenesis procedure" refers to template-dependent processes and vector-mediated propagation which result in an increase in the concentration of a specific nucleic acid molecule relative to its initial concentration, or in an increase in the concentration of a detectable signal, such as amplification. As used herein, the term "oligonucleotide directed mutagenesis procedure" also is intended to refer to a process that involves the template-dependent extension of a primer molecule. The term template-dependent process refers to nucleic acid synthesis of an RNA or a DNA molecule wherein the sequence of the newly synthesized strand of nucleic acid is dictated by the well-known rules of complementary base pairing (see, for example, Watson and Ramstad, 1987). Typically, vector mediated methodologies involve the introduction of the nucleic acid fragment into a DNA or RNA vector, the clonal amplification of the vector, and the recovery of the amplified nucleic acid fragment. Examples of such methodologies are provided by U.S. Pat. No. 4,237,224, specifically incorporated herein by reference in its entirety. A number of template dependent processes are available to amplify the target sequences of interest present in a sample, such methods being well known in the art and specifically disclosed herein below.

III. Transformation

There are many methods for transforming DNA segments into cells, but not all are suitable for delivering DNA to plant cells. Suitable methods for use with the current invention are believed to include virtually any method by which DNA can be introduced into a cell, such as by direct delivery of DNA such as by PEG-mediated transformation of protoplasts (Omirulleh et al., 1993), by desiccation/inhibition-mediated DNA uptake (Potrykus et al., 1985), by electroporation (U.S.

Pat. No. 5,384,253, specifically incorporated herein by reference in its entirety), by agitation with silicon carbide fibers (Kaeppler et al., 1990; U.S. Pat. No. 5,302,523, specifically incorporated herein by reference in its entirety; and U.S. Pat. No. 5,464,765, specifically incorporated herein by reference in its entirety), by Agrobacterium-mediated transformation (U.S. Pat. No. 5,591,616 and U.S. Pat. No. 5,563,055; both specifically incorporated herein by reference) and by acceleration of DNA coated particles (U.S. Pat. No. 5,550,318; U.S. Pat. No. 5,538,877; and U.S. Pat. No. 5,538,880; each specifically incorporated herein by reference in its entirety), etc. Through the application of techniques such as these, maize cells as well as those of virtually any other plant species may be stably transformed, and these cells developed into transgenic plants. In certain embodiments, acceleration methods are preferred and include, for example, microprojectile bombardment and the like.

(i) Electroporation

Where one wishes to introduce DNA by means of electroporation, it is contemplated that the method of Krzyzek et al. (U.S. Pat. No. 5,384,253, incorporated herein by reference in its entirety) will be particularly advantageous. In this method, certain cell wall-degrading enzymes, such as pectin-degrading enzymes, are employed to render the target recipient cells more susceptible to transformation by electroporation than untreated cells. Alternatively, recipient cells are made more susceptible to transformation by mechanical wounding.

To effect transformation by electroporation, one may employ either friable tissues, such as a suspension culture of cells or embryogenic callus or alternatively one may transform immature embryos or other organized tissue directly. In this technique, one would partially degrade the cell walls of the chosen cells by exposing them to pectin-degrading enzymes (pectolyases) or mechanically wounding in a controlled manner. Examples of some species which have been transformed by electroporation of intact cells include maize (U.S. Pat. No. 5,384,253; D'Halluin et al., 1992; Rhodes et al., 1995), wheat (Zhou et al., 1993), tomato (Hou and Lin, 1996), soybean (Christou et al., 1987), and tobacco (Lee et al., 1989).

One may also employ protoplasts for electroporation transformation of plants (Bates, 1994; Lazzeri, 1995). For example, the generation of transgenic soybean plants by electroporation of cotyledon-derived protoplasts is described by Dhir and Widholm in Intl. Patent Appl. Publ. No. WO 9217598 (specifically incorporated herein by reference). Other examples of species for which protoplast transformation has been described include barley (Lazerri, 1995), sorghum (Battraw et al., 1991), maize (Bhattacharjee et al., 1997), wheat (He et al., 1994), tomato (Tsukada, 1989), and soybean (Dhir et al., 1992).

(ii) Microprojectile Bombardment

A preferred method for delivering transforming DNA segments to plant cells in accordance with the invention is microprojectile bombardment (U.S. Pat. No. 5,550,318; U.S. Pat. No. 5,538,880; U.S. Pat. No. 5,610, 042; and PCT Application WO 94/09699; each of which is specifically incorporated herein by reference in its entirety). In this method, particles may be coated with nucleic acids and delivered into cells by a propelling force. Exemplary particles include those comprised of tungsten, platinum, and preferably, gold. It is contemplated that in some instances DNA precipitation onto metal particles would not be necessary for DNA delivery to a recipient cell using microprojectile bombardment. However, it is contemplated that particles may contain DNA rather than be coated with DNA. Hence, it is proposed that DNA-coated particles may increase the level of DNA delivery via particle bombardment but are not, in and of themselves, necessary.

An illustrative embodiment of a method for delivering DNA into maize cells by acceleration is the Biolistics Particle Delivery System, which can be used to propel particles coated with DNA or cells through a screen, such as a stainless steel or Nytex screen, onto a filter surface covered with monocot plant cells cultured in suspension. The screen disperses the particles so that they are not delivered to the recipient cells in large aggregates. It is believed that a screen intervening between the projectile apparatus and the cells to be bombarded reduces the size of projectiles aggregate and may contribute to a higher frequency of transformation by reducing the damage inflicted on the recipient cells by projectiles that are too large.

Microprojectile bombardment techniques are widely applicable, and may be used to transform virtually any plant species. Examples of species for which have been transformed by microprojectile bombardment include monocot species such as maize (PCT Application WO 95/06128), barley (Ritala et al., 1994; Hensgens et al., 1993), wheat (U.S. Pat. No. 5,563,055, specifically incorporated herein by reference in its entirety), rice (Hensgens et al., 1993), oat (Torbet et al., 1995; Torbet et al., 1998), rye (Hensgens et al., 1993), sugarcane (Bower et al., 1992), and sorghum (Casa et al., 1993; Hagio et al., 1991); as well as a number of dicots including tobacco (Tomes et al., 1990; Buising and Benbow, 1994), soybean (U.S. Pat. No. 5,322,783, specifically incorporated herein by reference in its entirety), sunflower (Knittel et al. 1994), peanut (Singsit et al., 1997), cotton (McCabe and Martinell, 1993), tomato (VanEck et al. 1995), and legumes in general (U.S. Pat. No. 5,563,055, specifically incorporated herein by reference in its entirety).

For the bombardment, cells in suspension are concentrated on filters or solid culture medium. Alternatively, immature embryos or other target cells may be arranged on solid culture medium. The cells to be bombarded are positioned at an appropriate distance below the macroprojectile stopping plate. If desired, one or more screens may be positioned between the acceleration device and the cells to be bombarded.

(iii) Agrobacterium-mediated Transformation

Agrobacterium-mediated transfer is a widely applicable system for introducing genes into plant cells because the DNA can be introduced into whole plant tissues, thereby bypassing the need for regeneration of an intact plant from a protoplast. The use of Agrobacterium-mediated plant integrating vectors to introduce DNA into plant cells is well known in the art. See, for example, the methods described by Fraley et al., (1985), Rogers et al., (1987) and U.S. Pat. No. 5,563,055, specifically incorporated herein by reference in its entirety.

Agrobacterium-mediated transformation is most efficient in dicotyledonous plants and is the preferable method for transformation of dicots, including Arabidopsis, tobacco, tomato, and potato. Indeed, while Agrobacterium-mediated transformation has been routinely used with dicotyledonous plants for a number of years, it has only recently become applicable to monocotyledonous plants. Advances in Agrobacterium-mediated transformation techniques have now made the technique applicable to nearly all monocotyledonous plants. For example, Agrobacterium-mediated transformation techniques have now been applied to rice (Hiei et al., 1997; Zhang et al., 1997; U.S. Pat. No. 5,591, 616, specifically incorporated herein by reference in its entirety), wheat (McCormac et al., 1998), barley (Tingay et al., 1997; McCormac et al., 1998), and maize (Ishidia et al., 1996).

Modern Agrobacterium transformation vectors are capable of replication in *E. coli* as well as Agrobacterium, allowing for convenient manipulations as described (Klee et al., 1985). Moreover, recent technological advances in vectors for Agrobacterium-mediated gene transfer have improved the arrangement of genes and restriction sites in the vectors to facilitate the construction of vectors capable of expressing various polypeptide coding genes. The vectors described (Rogers et al., 1987) have convenient multi-linker regions flanked by a promoter and a polyadenylation site for direct expression of inserted polypeptide coding genes and are suitable for present purposes. In addition, Agrobacterium containing both armed and disarmed Ti genes can be used for the transformations. In those plant strains where Agrobacterium-mediated transformation is efficient, it is the method of choice because of the facile and defined nature of the gene transfer.

(iv) Other Transformation Methods

Transformation of plant protoplasts can be achieved using methods based on calcium phosphate precipitation, polyethylene glycol treatment, electroporation, and combinations of these treatments (see, e.g., Potrykus et al., 1985; Lorz et al., 1985; Omirulleh et al., 1993; Fromm et al., 1986; Uchimiya et al., 1986; Callis et al., 1987; Marcotte et al., 1988).

Application of these systems to different plant strains depends upon the ability to regenerate that particular plant strain from protoplasts. Illustrative methods for the regeneration of cereals from protoplasts have been described (Fujimara et al., 1985; Toriyama et al., 1986; Yamada et al., 1986; Abdullah et al., 1986; Omirulleh et al., 1993 and U.S. Pat. No. 5,508,184; each specifically incorporated herein by reference in its entirety). Examples of the use of direct uptake transformation of cereal protoplasts include transformation of rice (Ghosh-Biswas et al., 1994), sorghum (Battraw and Hall, 1991), barley (Lazerri, 1995), oat (Zheng and Edwards, 1990) and maize (Omirulleh et al., 1993).

To transform plant strains that cannot be successfully regenerated from protoplasts, other ways to introduce DNA into intact cells or tissues can be utilized. For example, regeneration of cereals from immature embryos or explants can be effected as described (Vasil, 1989). Also, silicon carbide fiber-mediated transformation may be used with or without protoplasting (Kaeppler, 1990; Kaeppler et al., 1992; U.S. Pat. No. 5,563,055, specifically incorporated herein by reference in its entirety). Transformation with this technique is accomplished by agitating silicon carbide fibers together with cells in a DNA solution. DNA passively enters as the cell are punctured. This technique has been used successfully with, for example, the monocot cereals maize (PCT Application WO 95/06128, specifically incorporated herein by reference in its entirety; Thompson, 1995) and rice (Nagatani, 1997).

IV. Optimization of Microprojectile Bombardment

For microprojectile bombardment transformation in accordance with the current invention, both physical and biological parameters may be optimized. Physical factors are those that involve manipulating the DNA/microprojectile precipitate or those that affect the flight and velocity of either the macro- or microprojectiles. Biological factors include all steps involved in manipulation of cells before and immediately after bombardment, such as the osmotic adjustment of target cells to help alleviate the trauma associated with bombardment, the orientation of an immature embryo or other target tissue relative to the particle trajectory, and also the nature of the transforming DNA, such as linearized DNA or intact supercoiled plasmids. It is believed that pre-bombardment manipulations are especially important for successful transformation of immature embryos.

Accordingly, it is contemplated that one may wish to adjust various of the bombardment parameters in small scale studies to fully optimize the conditions. One may particularly wish to adjust physical parameters such as DNA concentration, gap distance, flight distance, tissue distance, and helium pressure. It is further contemplated that the grade of helium may effect transformation efficiency. For example, differences in transformation efficiencies may be witnessed between bombardments using industrial grade (99.99% pure) or ultra pure helium (99.999% pure), although it is not currently clear which is more advantageous for use in bombardment. One may also optimize the trauma reduction factors (TRFs) by modifying conditions which influence the physiological state of the recipient cells and which may therefore influence transformation and integration efficiencies. For example, the osmotic state, tissue hydration and the subculture stage or cell cycle of the recipient cells may be adjusted for optimum transformation.

Both physical and biological parameters for bombardment may be addressed for further optimization of ballistic transformation. Physical factors are those that involve manipulating the DNA/microprojectile precipitate or those that affect the flight and velocity of either the macro- or microprojectiles. Biological factors include all steps involved in manipulation of cells immediately before and after bombardment. The prebombardment culturing conditions, such as osmotic environment, the bombardment parameters, and the plasmid configuration have been adjusted to yield the maximum numbers of stable transformants.

(i) Physical Parameters

1. Gap Distance

The variable nest (macro holder) can be adjusted to vary the distance between the rupture disk and the macroprojectile, i.e., the gap distance. This distance can be varied from 0 to 2 cm. The predicted effects of a shorter gap are an increase of velocity of both the macro- and microprojectiles, an increased shock wave (which leads to tissue splattering and increased tissue trauma), and deeper penetration of microprojectiles. Longer gap distances would have the opposite effects but may increase viability and therefore the total number of recovered stable transformants.

2. Flight Distance

The fixed nest (contained within the variable nest) can be varied between 0.5 and 2.25 cm in predetermined 0.5 cm increments by the placement of spacer rings to adjust the flight path traversed by the macroprojectile. Short flight paths allow for greater stability of the macroprojectile in flight but reduce the overall velocity of the microprojectiles. Increased stability in flight increases, for example, the number of centered GUS foci. Greater flight distances (up to some point) increase velocity but also increase instability in flight. Based on observations, it is recommended that bombardments typically be done with a flight path length of about 1.0 cm to 1.5 cm.

3. Tissue Distance

Placement of tissue within the gun chamber can have significant effects on microprojectile penetration. Increasing the flight path of the microprojectiles will decrease velocity and trauma associated with the shock wave. A decrease in velocity also will result in shallower penetration of the microprojectiles.

4. Helium Pressure

By manipulation of the type and number of rupture disks, pressure can be varied between 400 and 2000 psi within the gas acceleration tube. Optimum pressure for stable transformation has been determined to be between 1000 and 1200 psi.

5. Coating of Microprojectiles.

For microprojectile bombardment, one will attach (i.e. "coat") DNA to the microprojectiles such that it is delivered to recipient cells in a form suitable for transformation thereof. In this respect, at least some of the transforming DNA must be available to the target cell for transformation to occur, while at the same time during delivery the DNA must be attached to the microprojectile. Therefore, availability of the transforming DNA from the microprojectile may comprise the physical reversal of bonds between transforming DNA and the microprojectile following delivery of the microprojectile to the target cell. This need not be the case, however, as availability to a target cell may occur as a result of breakage of unbound segments of DNA or of other molecules which comprise the physical attachment to the microprojectile. Availability may further occur as a result of breakage of bonds between the transforming DNA and other molecules, which are either directly or indirectly attached to the microprojectile. It further is contemplated that transformation of a target cell may occur by way of direct recombination between the transforming DNA and the genomic DNA of the recipient cell. Therefore, as used herein, a "coated" microprojectile will be one which is capable of being used to transform a target cell, in that the transforming DNA will be delivered to the target cell, yet will be accessible to the target cell such that transformation may occur.

Any technique for coating microprojectiles which allows for delivery of transforming DNA to the target cells may be used. Methods for coating microprojectiles which have been demonstrated to work well with the current invention have been specifically disclosed herein. DNA may be bound to microprojectile particles using alternative techniques, however. For example, particles may be coated with streptavidin and DNA end labeled with long chain thiol cleavable biotinylated nucleotide chains. The DNA adheres to the particles due to the streptavidin-biotin interaction, but is released in the cell by reduction of the thiol linkage through reducing agents present in the cell.

Alternatively, particles may be prepared by functionalizing the surface of a gold oxide particle, providing free amine groups. DNA, having a strong negative charge, binds to the functionalized particles. Furthermore, charged particles may be deposited in controlled arrays on the surface of mylar flyer disks used in the PDS-1000 Biolistics device, thereby facilitating controlled distribution of particles delivered to target tissue.

As disclosed above, it further is proposed, that the concentration of DNA used to coat microprojectiles may influence the recovery of transformants containing a single copy of the transgene. For example, a lower concentration of DNA may not necessarily change the efficiency of the transformation, but may instead increase the proportion of single copy insertion events. In this regard, approximately 1 ng to 2000 ng of transforming DNA may be used per each 1.8 mg of starting microprojectiles. In other embodiments of the invention, approximately 2.5 ng to 1000 ng, 2.5 ng to 750 ng, 2.5 ng to 500 ng, 2.5 ng to 250 ng, 2.5 ng to 100 or 2.5 ng to 50 ng of transforming DNA may be used per each 1.8 mg of starting microprojectiles.

Various other methods may also be used to increase transformation efficiency and/or increase the relative proportion of low-copy transformation events. For example, the inventors contemplate end-modifying transforming DNA with alkaline phosphatase or an agent which will blunt DNA ends prior to transformation. Still further, an inert carrier DNA may be included with the transforming DNA, thereby lowering the effective transforming DNA concentration without lowering the overall amount of DNA used. These techniques are further described in U.S. patent application Ser. No. 08/995,451, filed Dec. 22, 1997, the disclosure of which is specifically incorporated herein by reference in its entirety.

(ii) Biological Parameters

Culturing conditions and other factors can influence the physiological state of the target cells and may have profound effects on transformation and integration efficiencies. First, the act of bombardment could stimulate the production of ethylene which could lead to senescence of the tissue. The addition of antiethylene compounds could increase transformation efficiencies. Second, it is proposed that certain points in the cell cycle may be more appropriate for integration of introduced DNA. Hence synchronization of cell cultures may enhance the frequency of production of transformants. For example, synchronization may be achieved using cold treatment, amino acid starvation, or other cell cycle-arresting agents. Third, the degree of tissue hydration also may contribute to the amount of trauma associated with bombardment as well as the ability of the microprojectiles to penetrate cell walls.

The position and orientation of an embryo or other target tissue relative to the particle trajectory may also be important. For example, the PDS-1000 biolistics device does not produce a uniform spread of particles over the surface of a target petri dish. The velocity of particles in the center of the plate is higher than the particle velocity at further distances from the center of the petri dish. Therefore, it is advantageous to situate target tissue on the petri dish such as to avoid the center of the dish, referred to by some as the "zone of death." Furthermore, orientation of the target tissue with regard to the trajectory of targets also can be important. It is contemplated that it is desirable to orient the tissue most likely to regenerate a plant toward the particle stream. For example, the scutellum of an immature embryo comprises the cells of greatest embryogenic potential and therefore should be oriented toward the particle stream.

It also has been reported that slightly plasmolyzed yeast cells allow increased transformation efficiencies (Armaleo et al., 1990). It was hypothesized that the altered osmotic state of the cells helped to reduce trauma associated with the penetration of the microprojectile. Additionally, the growth and cell cycle stage may be important with respect to transformation.

1. Osmotic Adjustment

It has been suggested that osmotic pre-treatment could potentially reduce bombardment associated injury as a result of the decreased turgor pressure of the plasmolyzed cell. In a previous study, the number of cells transiently expressing GUS increased following subculture into both fresh medium and osmotically adjusted medium (PCT Application WO 95/06128, specifically incorporated herein by reference in its entirety). Pretreatment times of 90 minutes showed higher numbers of GUS expressing foci than shorter times. Cells incubated in 500 mOSM/kg medium for 90 minutes showed an approximately 3.5 fold increase in transient GUS foci than the control. Preferably, immature embryos are precultured for 4–5 hours prior to bombardment on culture medium containing 12% sucrose. A second culture on 12% sucrose is performed for 16–24 hours following bombardment. Alternatively, type II cells are pretreated on 0.2M mannitol for 3–4 hours prior to bombardment. It is contemplated that pretreatment of cells with other osmotically active solutes for a period of 1–6 hours may also be desirable.

2. Plasmid Configuration

In some instances, it will be desirable to deliver DNA to maize cells that does not contain DNA sequences necessary for maintenance of the plasmid vector in the bacterial host, e.g., E. coli, such as antibiotic resistance genes, including but not limited to ampicillin, kanamycin, and tetracycline resistance, and prokaryotic origins of DNA replication. In such case, a DNA fragment containing the transforming DNA may be purified prior to transformation. An exemplary method of purification is gel electrophoresis on a 1.2% low melting temperature agarose gel, followed by recovery from the agarose gel by melting gel slices in a 6–10 fold excess of Tris-EDTA buffer (10 mM Tris-HCl pH 8.0, 1 mM EDTA, 70° C.–72° C.); frozen and thawed (37° C.); and the agarose pelleted by centrifugation. A Qiagen Q-100 column then may be used for purification of DNA. For efficient recovery of DNA, the flow rate of the column may be adjusted to 40 ml/hr.

Isolated DNA fragments can be recovered from agarose gels using a variety of electroelution techniques, enzyme digestion of the agarose, or binding of DNA to glass beads (e.g., Gene Clean). In addition, HPLC and/or use of magnetic particles may be used to isolate DNA fragments. As an alternative to isolation of DNA fragments, a plasmid vector can be digested with a restriction enzyme and this DNA delivered to maize cells without prior purification of the expression cassette fragment.

V. Recipient Cells for Transformation

Tissue culture requires media and controlled environments. "Media" refers to the numerous nutrient mixtures that are used to grow cells in vitro, that is, outside of the intact living organism. The medium usually is a suspension of various categories of ingredients (salts, amino acids, growth regulators, sugars, buffers) that are required for growth of most cell types. However, each specific cell type requires a specific range of ingredient proportions for growth, and an even more specific range of formulas for optimum growth. Rate of cell growth also will vary among cultures initiated with the array of media that permit growth of that cell type.

Nutrient media is prepared as a liquid, but this may be solidified by adding the liquid to materials capable of providing a solid support. Agar is most commonly used for this purpose. Bactoagar, Hazelton agar, Gelrite, and Gelgro are specific types of solid support that are suitable for growth of plant cells in tissue culture.

Some cell types will grow and divide either in liquid suspension or on solid media. As disclosed herein, maize cells will grow in suspension or on solid medium, but regeneration of plants from suspension cultures requires transfer from liquid to solid media at some point in development. The type and extent of differentiation of cells in culture will be affected not only by the type of media used and by the environment, for example, pH, but also by whether media is solid or liquid. Table 2 illustrates the composition of various media useful for creation of recipient cells and for plant regeneration.

Recipient cell targets include, but are not limited to, meristem cells, including the shoot apex (U.S. Pat. No. 5,736,369), Type I, Type II, and Type III callus, immature embryos and gametic cells such as microspores, pollen, sperm and egg cells. It is contemplated that any cell from which a fertile plant may be regenerated is useful as a recipient cell. Type I, Type II, and Type III callus may be initiated from tissue sources including, but not limited to, immature embryos, seedling apical meristems, microspores and the like. Those cells which are capable of proliferating as callus are also recipient cells for genetic transformation. The present invention provides techniques for transforming immature embryos and subsequent regeneration of fertile transgenic plants. Transformation of immature embryos obviates the need for long term development of recipient cell cultures. Pollen, as well as its precursor cells, microspores, may be capable of functioning as recipient cells for genetic transformation, or as vectors to carry foreign DNA for incorporation during fertilization. Direct pollen transformation would obviate the need for cell culture. Meristematic cells (i.e., plant cells capable of continual cell division and characterized by an undifferentiated cytological appearance, normally found at growing points or tissues in plants such as root tips, stem apices, lateral buds, etc.) may represent another type of recipient plant cell. Because of their undifferentiated growth and capacity for organ differentiation and totipotency, a single transformed meristematic cell could be recovered as a whole transformed plant. In fact, it is proposed that embryogenic suspension cultures may be an in vitro meristematic cell system, retaining an ability for continued cell division in an undifferentiated state, controlled by the media environment.

Cultured plant cells that can serve as recipient cells for transforming with desired DNA segments may be any plant cells including corn cells, and more specifically, cells from Zea mays L. Somatic cells are of various types. Embryogenic cells are one example of somatic cells which may be induced to regenerate a plant through embryo formation. Non-embryogenic cells are those which typically will not respond in such a fashion. An example of non-embryogenic cells are certain Black Mexican Sweet (BMS) corn cells.

The development of embryogenic maize calli and suspension cultures useful in the context of the present invention, e.g., as recipient cells for transformation, has been described in U.S. Pat. No. 5,134,074; and U.S. Pat. No. 5,489,520; each of which is incorporated herein by reference in its entirety.

Certain techniques may be used that enrich recipient cells within a cell population. For example, Type II callus development, followed by manual selection and culture of friable, embryogenic tissue, generally results in an enrichment of recipient cells for use in, microprojectile transformation. Suspension culturing, particularly using the media disclosed herein, may improve the ratio of recipient to non-recipient cells in any given population. Manual selection techniques which can be employed to select recipient cells may include, e.g., assessing cell morphology and differentiation, or may use various physical or biological means. Cryopreservation is also a possible method of selecting for recipient cells.

Manual selection of recipient cells, e.g., by selecting embryogenic cells from the surface of a Type II callus, is one means that may be used in an attempt to enrich for recipient cells prior to culturing (whether cultured on solid media or in suspension). The preferred cells may be those located at the surface of a cell cluster, and may further be identifiable by their lack of differentiation, their size and dense cytoplasm. The preferred cells will generally be those cells which are less differentiated, or not yet committed to differentiation. Thus, one may wish to identify and select those cells which are cytoplasmically dense, relatively unvacuolated with a high nucleus to cytoplasm ratio (e.g., determined by cytological observations), small in size (e.g., 10–20 $\mu$m), and capable of sustained divisions and somatic proembryo formation.

It is proposed that other means for identifying such cells may also be employed. For example, through the use of dyes, such as Evan's blue, which are excluded by cells with relatively non-permeable membranes, such as embryogenic cells, and taken up by relatively differentiated cells such as root-like cells and snake cells (so-called due to their snake-like appearance).

Other possible means of identifying recipient cells include the use of isozyme markers of embryogenic cells, such as glutamate dehydrogenase, which can be detected by cytochemical stains (Fransz et al., 1989). However, it is cautioned that the use of isozyme markers including glutamate dehydrogenase may lead to some degree of false positives from non-embryogenic cells such as rooty cells which nonetheless have a relatively high metabolic activity.

(i) Culturing Cells to be Recipients for Transformation

The ability to prepare and cryopreserve cultures of maize cells is important to certain aspects of the present invention, in that it provides a means for reproducibly and successfully preparing cells for transformation. A variety of different types of media have been previously developed and may be employed in carrying out various aspects of the invention. The following table, Table 2, sets forth the composition of the media preferred by the inventor for carrying out these aspects of the invention.

TABLE 2

Tissue Culture Media Which are Used for Type II Callus Development, Development of Suspension Cultures and Regeneration of Plant Cells (Particularly Maize Cells)

| MEDIA NO. | BASAL MEDIUM | SUCROSE | pH | OTHER COMPONENTS** (Amount/L) |
|---|---|---|---|---|
| 7 | MS* | 2% | 6.0 | .25 mg thiamine<br>.5 mg BAP<br>.5 mg NAA<br>Bactoagar |
| 10 | MS | 2% | 6.0 | .25 mg thiamine<br>1 mg BAP<br>1 mg 2,4-D<br>400 mg L-proline<br>Bactoagar |
| 19 | MS | 2% | 6.0 | .25 mg thiamine<br>.25 mg BAP<br>.25 mg NAA<br>Bactoagar |
| 20 | MS | 3% | 6.0 | .25 mg thiamine<br>1 mg BAP<br>1 mg NAA<br>Bactoagar |
| 52 | MS | 2% | 6.0 | .25 mg thiamine<br>1 mg 2,4-D<br>$10^{-7}$ M ABA<br>BACTOAGAR |
| 101 | MS | 3% | 6.0 | MS vitamins<br>100 mg myo-inositol<br>Bactoagar |
| 142 | MS | 6% | 6.0 | MS vitamins<br>5 mg BAP<br>0.186 mg NAA<br>0.175 mg IAA<br>0.403 mg 2IP<br>Bactoagar |
| 157 | MS | 6% | 6.0 | MS vitamins<br>100 mg myo-inositol<br>Bactoagar |
| 163 | MS | 3% | 6.0 | MS vitamins<br>3.3 mg dicamba<br>100 mg myo-inositol<br>Bactoagar |

TABLE 2-continued

Tissue Culture Media Which are Used for Type II Callus Development, Development of Suspension Cultures and Regeneration of Plant Cells (Particularly Maize Cells)

| MEDIA NO. | BASAL MEDIUM | SUCROSE | pH | OTHER COMPONENTS** (Amount/L) |
|---|---|---|---|---|
| 171 | MS | 3% | 6.0 | MS vitamins<br>.25 mg 2,4-D<br>10 mg BAP<br>100 mg myo-inositol<br>Bactoagar |
| 173 | MS | 6% | 6.0 | MS vitamins<br>5 mg BAP<br>.186 mg NAA<br>.175 mg IAA<br>.403 mg 2IP<br>$10^{-7}$ M ABA<br>200 mg myo-inositol<br>Bactoagar |
| 177 | MS | 3% | 6.0 | MS vitamins<br>.25 mg 2,4-D<br>10 mg BAP<br>$10^{-7}$ M ABA<br>100 mg myo-inositol<br>Bactoagar |
| 185 | MS | — | 5.8 | 3 mg BAP<br>.04 mg NAA<br>RT vitamins<br>1.65 mg thiamine<br>1.38 g L-proline<br>20 g sorbitol<br>Bactoagar |
| 189 | MS | — | 5.8 | 3 mg BAP<br>.04 mg NAA<br>.5 mg niacin<br>800 mg L-asparagine<br>100 mg casamino acids<br>20 g sorbitol<br>1.4 g L-proline<br>100 mg myo-inositol<br>Gelgro |
| 201 | N6 | 2% | 5.8 | N6 vitamins<br>2 mg L-glycine<br>1 mg 2,4-D<br>100 mg casein hydrolysate<br>2.9 g L-proline<br>Gelgro |
| 205 | N6 | 2% | 5.8 | N6 vitamins<br>2 mg L-glycine<br>.5 mg 2,4-D<br>100 mg casein hydrolysate<br>2.9 g L-proline<br>Gelgro |
| 209 | N6 | 6% | 5.8 | N6 vitamins<br>2 mg L-glycine<br>100 mg casein hydrolysate<br>0.69 g L-proline<br>Bactoagar |
| 210 | N6 | 3% | 5.5 | N6 vitamins<br>2 mg 2,4-D<br>250 mg Ca pantothenate<br>100 mg myo-inositol<br>790 mg L-asparagine<br>100 mg casein hydrolysate<br>1.4 g L-proline<br>Hazelton agar****<br>2 mg L-glycine |
| 212 | N6 | 3% | 5.5 | N6 vitamins<br>2 mg L-glycine<br>2 mg 2,4-D<br>250 mg Ca pantothenate<br>100 mg myo-inositol<br>100 mg casein hydrolysate |

TABLE 2-continued

Tissue Culture Media Which are Used for Type II Callus Development, Development of Suspension Cultures and Regeneration of Plant Cells (Particularly Maize Cells)

| MEDIA NO. | BASAL MEDIUM | SUCROSE | pH | OTHER COMPONENTS** (Amount/L) |
|---|---|---|---|---|
| 227 | N6 | 2% | 5.8 | 1.4 g L-proline<br>Hazelton agar****<br>N6 vitamins<br>2 mg L-glycine<br>13.2 mg dicamba<br>100 mg casein hydrolysate<br>2.9 g L-proline Gelgro |
| 273 (also, 201V, 236S, 201D, 2071, 2366, 201SV, 2377, and 201BV) | N6 | 2% | 5.8 | N6 vitamins<br>2 mg L-glycine<br>1 mg 2,4-D<br>16.9 mg AgNO$_3$<br>100 mg casein hydrolysate<br>2.9 g L-proline |
| 279 | N6 | 2% | 5.8 | 3.3 mg dicamba<br>1 mg thiamine<br>.5 mg niacin<br>800 mg L-asparagine<br>100 mg casein hydrolysate<br>100 mg myoinositol<br>1.4 g L-proline<br>Gelgro**** |
| 288 | N6 | 3% | | 3.3 mg dicamba<br>1 mg thiamine<br>.5 mg niacin<br>.8 g L-asparagine<br>100 mg myo-inosital<br>1.4 g L-proline<br>100 mg casein hydrolysate<br>16.9 mg AgNO$_3$ Gelcro |
| 401 | MS | 3% | 6.0 | 3.73 mg Na$_2$EDTA<br>.25 mg thiamine<br>1 mg 2,4-D<br>2 mg NAA<br>200 mg casein hydrolysate<br>500 mg K$_2$SO$_4$<br>400 mg KH$_2$PO$_4$<br>100 mg myo-inositol |
| 402 | MS | 3% | 6.0 | 3.73 mg Na$_2$EDTA<br>.25 mg thiamine<br>1 mg 2,4-D<br>200 mg casein hydrolysate<br>2.9 g L-proline<br>500 mg K$_2$SO$_4$<br>400 mg KH$_2$PO$_4$<br>100 mg myo-inositol |
| 409 | MS | 3% | 6.0 | 3.73 mg Na$_2$EDTA<br>.25 mg thiamine<br>9.9 mg dicamba<br>200 mg casein hydrolysate<br>2.9 g L-proline<br>500 mg K$_2$SO$_4$<br>400 mg KH$_2$PO$_4$<br>100 mg myo-inositol |
| 501 | Clark's Medium*** | 2% | 5.7 | |
| 607 | ½ × MS | 3% | 5.8 | 1 mg thiamine<br>1 mg niacin<br>Gelrite |
| 615 | MS | 3% | 6.0 | MS vitamins<br>6 mg BAP<br>100 mg myo-inositol<br>Bactoagar |
| 617 | ½ × MS | 1.5% | 6.0 | MS vitamins<br>50 mg myo-inositol<br>Bactoagar |
| 708 | N6 | 2% | 5.8 | N6 vitamins<br>2 mg L-glycine<br>1.5 mg 2,4-D<br>200 mg casein hydrolysate<br>0.69 g L-proline<br>Gelrite |
| 721 | N6 | 2% | 5.8 | 3.3 mg dicamba<br>1 mg thiamine<br>.5 mg niacin<br>800 mg L-asparagine<br>100 mg myo-inositol<br>100 mg casein hydrolysate<br>1.4 g L-proline<br>54.65 g mannitol<br>Gelgro |
| 726 | N6 | 3% | 5.8 | 3.3 mg dicamba<br>.5 mg niacin<br>1 mg thiamine<br>800 mg L-asparagine<br>100 mg myo-inositol<br>100 mg casein hydrolysate<br>1.4 g L-proline |
| 727 | N6 | 3% | 5.8 | N6 vitamins<br>2 mg L-glycine<br>9.9 mg dicamba<br>100 mg casein hydrolysate<br>2.9 g L-proline<br>Gelgro |
| 728 | N6 | 3% | 5.8 | N6 vitamins<br>2 mg L-glycine<br>9.9 mg dicamba<br>16.9 mg AgNO$_3$<br>100 mg casein hydrolysate<br>2.9 g L-proline<br>Gelgro |
| 734 | N6 | 2% | 5.8 | N6 vitamins<br>2 mg L-glycine<br>1.5 mg 2,4-D<br>14 g Fe sequestreene (replaces Fe-EDTA)<br>200 mg casein hydrolyste<br>0.69 g L-proline<br>Gelrite |
| 735 | N6 | 2% | 5.8 | 1 mg 2,4-D<br>.5 mg niacin<br>.91 g L-asparagine<br>100 mg myo-inositol<br>1 mg thiamine<br>.5 g MES<br>.75 g MgCl$_2$<br>100 mg casein hydrolysate<br>0.69 g L-proline<br>Gelgro |
| 2004 | N6 | 3% | 5.8 | 1 mg thiamine<br>0.5 mg niacin<br>3.3 mg dicamba<br>17 mg AgNO$_3$<br>1.4 g L-proline<br>0.8 g L-asparagine<br>100 mg casein hydrolysate<br>100 mg myo-inositol<br>Gelrite |
| 2008 | N6 | 3% | 5.8 | 1 mg thiamine<br>0.5 mg niacin<br>3.3 mg dicamba |

TABLE 2-continued

Tissue Culture Media Which are Used for Type II Callus Development, Development of Suspension Cultures and Regeneration of Plant Cells (Particularly Maize Cells)

| MEDIA NO. | BASAL MEDIUM | SUCROSE | pH | OTHER COMPONENTS** (Amount/L) |
|---|---|---|---|---|
| | | | | 1.4 g L-proline |
| | | | | 0.8 g L-asparagine |
| | | | | Gelrite |

*Basic MS medium described in Murashige and Skoog (1962). This medium is typically modified by decreasing the $NH_4NO_3$ from 1.64 g/l to 1.55 g/l, and omitting the pyridoxine HCl, nicotinic acid, myo-inositol and glycine.
**NAA = Napthol Acetic Acid   IAA = Indole Acetic Acid   2-IP = 2, isopentyl adenine   2,4-D = 2,4-Dichlorophenoxyacetic Acid   BAP = 6-Benzyl aminopurine   ABA = abscisic acid
***Basic medium described in Clark (1982)
****These media may be made with or without solidifying agent.

A number of exemplary maize cultures which may be used for transformation have been developed and are disclosed in PCT Application WO 95/06128, which is specifically incorporated herein by reference.

(ii) Media

In certain embodiments of the current invention, recipient cells may be selected following growth in culture. Where employed, cultured cells may be grown either on solid supports or in the form of liquid suspensions. In either instance, nutrients may be provided to the cells in the form of media, and environmental conditions controlled. There are many types of tissue culture media comprised of various amino acids, salts, sugars, growth regulators and vitamins. Most of the media employed in the practice of the invention will have some similar components (see Table 2), but may differ in the composition and proportions of their ingredients depending on the particular application envisioned. For example, various cell types usually grow in more than one type of media, but will exhibit different growth rates and different morphologies, depending on the growth media. In some media, cells survive but do not divide.

Various types of media suitable for culture of plant cells previously have been described. Examples of these media include, but are not limited to, the N6 medium described by Chu et al. (1975) and MS media (Murashige and Skoog, 1962). It has been discovered that media such as MS which have a high ammonia/nitrate ratio are counterproductive to the generation of recipient cells in that they promote loss of morphogenic capacity. N6 media, on the other hand, has a somewhat lower ammonia/nitrate ratio, and is contemplated to promote the generation of recipient cells by maintaining cells in a proembryonic state capable of sustained divisions.

(iii) Maintenance

The method of maintenance of cell cultures may contribute to their utility as sources of recipient cells for transformation. Manual selection of cells for transfer to fresh culture medium, frequency of transfer to fresh culture medium, composition of culture medium, and environmental factors including, but not limited to, light quality and quantity and temperature are all important factors in maintaining callus and/or suspension cultures that are useful as sources of recipient cells. It is contemplated that alternating callus between different culture conditions may be beneficial in enriching for recipient cells within a culture. For example, it is proposed that cells may be cultured in suspension culture, but transferred to solid medium at regular intervals. After a period of growth on solid medium cells can be manually selected for return to liquid culture medium. It is proposed that by repeating this sequence of transfers to fresh culture medium it is possible to enrich for recipient cells. It also is contemplated that passing cell cultures through a 1.9 mm sieve is useful in maintaining the friability of a callus or suspension culture and may be beneficial in enriching for transformable cells.

(iv) Cryopreservation Methods

Cryopreservation is important because it allows one to maintain and preserve a known transformable cell culture for future use, while eliminating the cumulative detrimental effects associated with extended culture periods.

Cell suspensions and callus were cryopreserved using modifications of methods previously reported (Finkle, 1985; Withers & King, 1979). The cryopreservation protocol comprised adding a pre-cooled (0° C.) concentrated cryoprotectant mixture stepwise over a period of one to two hours to pre-cooled (0° C.) cells. The mixture was maintained at 0C throughout this period. The volume of added cryoprotectant was equal to the initial volume of the cell suspension (1:1 addition), and the final concentration of cryoprotectant additives was 10% dimethyl sulfoxide, 10% polyethylene glycol (6000 MW), 0.23 M proline and 0.23 M glucose. The mixture was allowed to equilibrate at 0° C. for 30 minutes, during which time the cell suspension/cryoprotectant mixture was divided into 1.5 ml aliquot (0.5 ml packed cell volume) in 2 ml polyethylene cryo-vials. The tubes were cooled at 0.5° C./minute to −8° C. and held at this temperature for ice nucleation.

Once extracellular ice formation had been visually confirmed, the tubes were cooled at 0.5° C./minute from −8° C. to −35° C. They were held at this temperature for 45 minutes (to insure uniform freeze-induced dehydration throughout the cell clusters). At this point, the cells had lost the majority of their osmotic volume (i.e., there is little free water left in the cells), and they could be safely plunged into liquid nitrogen for storage. The paucity of free water remaining in the cells in conjunction with the rapid cooling rates from −35° C. to −196° C. prevented large organized ice crystals from forming in the cells. The cells are stored in liquid nitrogen, which effectively immobilizes the cells and slows metabolic processes to the point where long-term storage should not be detrimental.

Thawing of the extracellular solution was accomplished by removing the cryo-tube from liquid nitrogen and swirling it in sterile 42° C. water for approximately 2 minutes. The tube was removed from the heat immediately after the last ice crystals had melted to prevent heating the tissue. The cell suspension (still in the cryoprotectant mixture) was pipetted onto a filter, resting on a layer of BMS cells (the feeder layer which provided a nurse effect during recovery). The cryoprotectant solution is removed by pipetting. Culture medium comprised a callus proliferation medium with increased osmotic strength. Dilution of the cryoprotectant occurred slowly as the solutes diffused away through the filter and nutrients diffused upward to the recovering cells. Once subsequent growth of the thawed cells was noted, the growing tissue was transferred to fresh culture medium. If initiation of a suspension culture was desired, the cell clusters were transferred back into liquid suspension medium as soon as sufficient cell mass had been regained (usually within 1 to 2 weeks). Alternatively, cells were cultured on solid callus proliferation medium. After the culture was reestablished in liquid (within 1 to 2 additional weeks), it was used for transformation experiments. When desired, previously cryopreserved cultures may be frozen again for storage.

VI. Production and Characterization of Stably Transformed Maize

After effecting delivery of exogenous DNA to recipient cells, the next steps generally concern identifying the transformed cells for further culturing and plant regeneration. As mentioned herein, in order to improve the ability to identify transformants, one may desire to employ a selectable or screenable marker gene as, or in addition to, the expressible gene of interest. In this case, one would then generally assay the potentially transformed cell population by exposing the cells to a selective agent or agents, or one would screen the cells for the desired marker gene trait.

(i) Selection

It is believed that DNA is introduced into only a small percentage of target cells in any one experiment. In order to provide an efficient system for identification of those cells receiving DNA and integrating it into their genomes one may employ a means for selecting those cells that are stably transformed. One exemplary embodiment of such a method is to introduce into the host cell, a marker gene which confers resistance to some normally inhibitory agent, such as an antibiotic or herbicide. Examples of antibiotics which may be used include the aminoglycoside antibiotics neomycin, kanamycin and paromomycin, or the antibiotic hygromycin. Resistance to the aminoglycoside antibiotics is conferred by aninoglycoside phosphostransferase enzymes such as neomycin phosphotransferase II (NPT II) or NPT I, whereas resistance to hygromycin is conferred by hygromycin phosphotransferase.

Potentially transformed cells then are exposed to the selective agent. In the population of surviving cells will be those cells where, generally, the resistance-conferring gene has been integrated and expressed at sufficient levels to permit cell survival. Cells may be tested further to confirm stable integration of the exogenous DNA. Using the techniques disclosed herein, greater than 40% of bombarded embryos may yield transformants.

One herbicide which has been suggested as a desirable selection agent is the broad spectrum herbicide bialaphos. Bialaphos is a tripeptide antibiotic produced by *Streptomyces hygroscopicus* and is composed of phosphinothricin (PPT), an analogue of L-glutamic acid, and two L-alanine residues. Upon removal of the L-alanine residues by intracellular peptidases, the PPT is released and is a potent inhibitor of glutamine synthetase (GS), a pivotal enzyme involved in ammonia assimilation and nitrogen metabolism (Ogawa et al., 1973). Synthetic PPT, the active ingredient in the herbicide Liberty™ is also effective as a selection agent. Inhibition of GS in plants by PPT causes the rapid accumulation of ammonia and death of the plant cells.

The organism producing bialaphos and other species of the genus Streptomyces also synthesizes an enzyme phosphinothricin acetyl transferase (PAT) which is encoded by the bar gene in *Streptomyces hygroscopicus* and the pat gene in *Streptomyces viridochromogenes*. The use of the herbicide resistance gene encoding phosphinothricin acetyl transferase (PAT) is referred to in DE 3642 829 A, wherein the gene is isolated from *Streptomyces viridochromogenes*. In the bacterial source organism, this enzyme acetylates the free amino group of PPT preventing auto-toxicity (Thompson et al., 1987). The bar gene has been cloned (Murakami et al., 1986; Thompson et al., 1987) and expressed in transgenic tobacco, tomato, potato (De Block, 1987) Brassica (De Block, 1989) and maize (U.S. Pat. No. 5,550,318). In previous reports, some transgenic plants which expressed the resistance gene were completely resistant to commercial formulations of PPT and bialaphos in greenhouses.

Another example of a herbicide which is useful for selection of transformed cell lines in the practice of the invention is the broad spectrum herbicide glyphosate. Glyphosate inhibits the action of the enzyme EPSPS which is active in the aromatic amino acid biosynthetic pathway. Inhibition of this enzyme leads to starvation for the amino acids phenylalanine, tyrosine, and tryptophan and secondary metabolites derived thereof. U.S. Pat. No. 4,535,060 describes the isolation of EPSPS mutations which confer glyphosate resistance on the *Salmonella typhimurium* gene for EPSPS, aroA. The EPSPS gene was cloned from *Zea mays* and mutations similar to those found in a glyphosate resistant aroA gene were introduced in vitro. Mutant genes encoding glyphosate resistant EPSPS enzymes are described in, for example, International Patent WO 97/4103. The best characterized mutant EPSPS gene conferring glyphosate resistance comprises amino acid changes at residues 102 and 106, although it is anticipated that other mutations will also be useful (PCT/WO97/4103).

To use the bar-bialaphos or the EPSPS-glyphosate selective system, bombarded tissue is cultured for 0–28 days on nonselective medium and subsequently transferred to medium containing from 1–3 mg/l bialaphos or 1–3 mM glyphosate as appropriate. While ranges of 1–3 mg/l bialaphos or 1–3 mM glyphosate will typically be preferred, it is proposed that ranges of 0.1–50 mg/l bialaphos or 0.1–50 mM glyphosate will find utility in the practice of the invention. Tissue can be placed on any porous, inert, solid or semi-solid support for bombardment, including but not limited to filters and solid culture medium. Bialaphos and glyphosate are provided as examples of agents suitable for selection of transformants, but the technique of this invention is not limited to them.

It is further contemplated that the herbicide DALAPON, 2,2-dichloropropionic acid, may be useful for identification of transformed cells. The enzyme 2,2-dichloropropionic acid dehalogenase (deh) inactivates the herbicidal activity of 2,2-dichloropropionic acid and therefore confers herbicidal resistance on cells or plants expressing a gene encoding the dehalogenase enzyme (Buchanan-Wollaston et al., 1992; PCT Application WO 95/06128; U.S. Pat. No. 5,508,468; U.S. Pat. No. 5,508,468).

Alternatively, a gene encoding an anthranilate synthase gene which confers resistance to certain amino acid analogs, e.g., 5-methyltryptophan or 6-methyl anthranilate, may be useful as a selectable marker gene. The use of an anthranilate synthase gene as a selectable marker was described in U.S. Pat. No. 5,508,468; and U.S. patent application Ser. No. 08/604,789.

An example of a screenable marker trait is the red pigment produced under the control of the R-locus in maize. This pigment may be detected by culturing cells on a solid support containing nutrient media capable of supporting growth at this stage and selecting cells from colonies (visible aggregates of cells) that are pigmented. These cells may be cultured further, either in suspension or on solid media. The R-locus is useful for selection of transformants from bombarded immature embryos. In a similar fashion, the introduction of the C1 and B genes will result in pigmented cells and/or tissues.

The enzyme luciferase may be used as a screenable marker in the context of the present invention. In the presence of the substrate luciferin, cells expressing luciferase emit light which can be detected on photographic or x-ray film, in a luminometer (or liquid scintillation counter), by devices that enhance night vision, or by a highly light sensitive video camera, such as a photon counting camera. All of these assays are nondestructive and transformed cells may be cultured further following identification. The photon counting camera is especially valuable as it allows one to identify specific cells or groups of cells which are expressing luciferase and manipulate those in real time. Another screenable marker which may be used is the gene coding for green fluorescent protein (Sheen et al., 1995).

It is further contemplated that combinations of screenable and selectable markers will be useful for identification of transformed cells. In some cell or tissue types a selection agent, such as bialaphos or glyphosate, may either not provide enough killing activity to clearly recognize transformed cells or may cause substantial nonselective inhibition of transformants and nontransformants alike, thus causing the selection technique to not be effective. It is proposed that selection with a growth inhibiting compound, such as bialaphos or glyphosate at concentrations below those that cause 100% inhibition followed by screening of growing tissue for expression of a screenable marker gene such as luciferase would allow one to recover transformants from cell or tissue types that are not amenable to selection alone. It is proposed that combinations of selection and screening may enable one to identify transformants in a wider variety of cell and tissue types.

(ii) Regeneration and Seed Production

Cells that survive the exposure to the selective agent, or cells that have been scored positive in a screening assay, may be cultured in media that supports regeneration of plants. In an exemplary embodiment, MS and N6 media may be modified (see Table 2) by including further substances such as growth regulators. A preferred growth regulator for such purposes is dicamba or 2,4-D. However, other growth regulators may be employed, including NAA, NAA+2,4-D or perhaps even picloram. Media improvement in these and like ways has been found to facilitate the growth of cells at specific developmental stages. Tissue may be maintained on a basic media with growth regulators until sufficient tissue is available to begin plant regeneration efforts, or following repeated rounds of manual selection, until the morphology of the tissue is suitable for regeneration, at least 2 wk, then transferred to media conducive to maturation of embryoids. Cultures are transferred every 2 wk on this medium. Shoot development will signal the time to transfer to medium lacking growth regulators.

The transformed cells, identified by selection or screening and cultured in an appropriate medium that supports regeneration, will then be allowed to mature into plants. Developing plantlets are transferred to soilless plant growth mix, and hardened, e.g., in an environmentally controlled chamber at about 85% relative humidity, 600 ppm $CO_2$, and 25–250 microeinsteins $m^{-2} s^{-1}$ of light. Plants are preferably matured either in a growth chamber or greenhouse. Plants are regenerated from about 6 wk to 10 months after a transformant is identified, depending on the initial tissue. During regeneration, cells are grown on solid media in tissue culture vessels. Illustrative embodiments of such vessels are petri dishes and Plant Cons. Regenerating plants are preferably grown at about 19 to 28° C. After the regenerating plants have reached the stage of shoot and root development, they may be transferred to a greenhouse for further growth and testing.

Note, however, that kernels on transformed plants may occasionally require embryo rescue due to cessation of kernel development and premature senescence of plants. To rescue developing embryos, they are excised from surface-disinfected kernels 10–20 days post-pollination and cultured. An embodiment of media used for culture at this stage comprises MS salts, 2% sucrose, and 5.5 g/l agarose. In embryo rescue, large embryos (defined as greater than 3 mm in length) are germinated directly on an appropriate media. Embryos smaller than that may be cultured for 1 wk on media containing the above ingredients along with $10^{-5}$M abscisic acid and then transferred to growth regulator-free medium for germination.

Progeny may be recovered from the transformed plants and tested for expression of the exogenous expressible gene by localized application of an appropriate substrate to plant parts such as leaves. In the case of bar transformed plants, it was found that transformed parental plants ($R_O$) and their progeny of any generation tested exhibited no bialaphos-related necrosis after localized application of the herbicide Basta to leaves, if there was functional PAT activity in the plants as assessed by an in vitro enzymatic assay. All PAT positive progeny tested contained bar, confirming that the presence of the enzyme and the resistance to bialaphos were associated with the transmission through the germline of the marker gene.

(iii) Characterization

To confirm the presence of the exogenous DNA or "transgene(s)" in the regenerating plants, a variety of assays may be performed. Such assays include, for example, "molecular biological" assays, such as Southern and Northern blotting and PCR™; "biochemical" assays, such as detecting the presence of a protein product, e.g., by immunological means (ELISAs and Western blots) or by enzymatic function; plant part assays, such as leaf or root assays; and also, by analyzing the phenotype of the whole regenerated plant.

1. DNA Integration, RNA Expression and Inheritance

Genomic DNA may be isolated from callus cell lines or any plant parts to determine the presence of the exogenous gene through the use of techniques well known to those skilled in the art. Note, that intact sequences will not always be present, presumably due to rearrangement or deletion of sequences in the cell.

The presence of DNA elements introduced through the methods of this invention may be determined by polymerase chain reaction (PCR™). Using this technique discreet fragments of DNA are amplified and detected by gel electrophoresis. This type of analysis permits one to determine whether a gene is present in a stable transformant, but does not prove integration of the introduced gene into the host cell genome. It is the experience of the inventor, however, that DNA has been integrated into the genome of all transformants that demonstrate the presence of the gene through PCR™ analysis. In addition, it is not possible using PCR™ techniques to determine whether transformants have exogenous genes introduced into different sites in the genome, i.e., whether transformants are of independent origin. It is contemplated that using PCR™ techniques it would be possible to clone fragments of the host genomic DNA adjacent to an introduced gene.

Positive proof of DNA integration into the host genome and the independent identities of transformants may be determined using the technique of Southern hybridization. Using this technique specific DNA sequences that were introduced into the host genome and flanking host DNA sequences can be identified. Hence the Southern hybridization pattern of a given transformant serves as an identifying characteristic of that transformant. In addition it is possible through Southern hybridization to demonstrate the presence of introduced genes in high molecular weight DNA, i.e., confirm that the introduced gene has been integrated into the host cell genome. The technique of Southern hybridization provides information that is obtained using PCR™, e.g., the presence of a gene, but also demonstrates integration into the genome and characterizes each individual transformant.

It is contemplated that using the techniques of dot or slot blot hybridization which are modifications of Southern hybridization techniques one could obtain the same information that is derived from PCR™, e.g., the presence of a gene.

Both PCR™ and Southern hybridization techniques can be used to demonstrate transmission of a transgene to progeny. In most instances the characteristic Southern hybridization pattern for a given transformant will segregate in progeny as one or more Mendelian genes (Spencer et al., 1992) indicating stable inheritance of the transgene.

Whereas DNA analysis techniques may be conducted using DNA isolated from any part of a plant, RNA will only be expressed in particular cells or tissue types and hence it will be necessary to prepare RNA for analysis from these tissues. PCR™ techniques may also be used for detection and quantitation of RNA produced from introduced genes. In this application of PCR™ it is first necessary to reverse transcribe RNA into DNA, using enzymes such as reverse transcriptase, and then through the use of conventional PCR™ techniques amplify the DNA. In most instances PCR™ techniques, while useful, will not demonstrate integrity of the RNA product. Further information about the nature of the RNA product may be obtained by Northern blotting. This technique will demonstrate the presence of an RNA species and give information about the integrity of that RNA. The presence or absence of an RNA species can also be determined using dot or slot blot Northern hybridizations. These techniques are modifications of Northern blotting and will only demonstrate the presence or absence of an RNA species.

2. Gene Expression

While Southern blotting and PCR™ may be used to detect the gene(s) in question, they do not provide information as to whether the gene is being expressed. Expression may be evaluated by specifically identifying the protein products of the introduced genes or evaluating the phenotypic changes brought about by their expression.

Assays for the production and identification of specific proteins may make use of physical-chemical, structural, functional, or other properties of the proteins. Unique physical-chemical or structural properties allow the proteins to be separated and identified by electrophoretic procedures, such as native or denaturing gel electrophoresis or isoelectric focusing, or by chromatographic techniques such as ion exchange or gel exclusion chromatography. The unique structures of individual proteins offer opportunities for use of specific antibodies to detect their presence in formats such as an ELISA assay. Combinations of approaches may be employed with even greater specificity such as western blotting in which antibodies are used to locate individual gene products that have been separated by electrophoretic techniques. Additional techniques may be employed to absolutely confirm the identity of the product of interest such as evaluation by amino acid sequencing following purification. Although these are among the most commonly employed, other procedures may be additionally used.

Assay procedures also may be used to identify the expression of proteins by their functionality, especially the ability of enzymes to catalyze specific chemical reactions involving specific substrates and products. These reactions may be followed by providing and quantifying the loss of substrates or the generation of products of the reactions by physical or chemical procedures. Examples are as varied as the enzyme to be analyzed and may include assays for PAT enzymatic activity by following production of radiolabeled acetylated phosphinothricin from phosphinothricin and $^{14}$C-acetyl CoA or for anthranilate synthase activity by following loss of fluorescence of anthranilate, to name two.

Very frequently the expression of a gene product is determined by evaluating the phenotypic results of its expression. These assays also may take many forms including but not limited to analyzing changes in the chemical composition, morphology, or physiological properties of the plant. Chemical composition may be altered by expression of genes encoding enzymes or storage proteins which change amino acid composition and may be detected by amino acid analysis, or by enzymes which change starch quantity which may be analyzed by near infrared reflectance spectrometry. Morphological changes may include greater stature or thicker stalks. Most often changes in response of plants or plant parts to imposed treatments are evaluated under carefully controlled conditions termed bioassays.

VII. Breeding Plants of the Invention

In addition to direct transformation of a particular genotype with a construct according to the current invention, plants of the invention may be made by crossing a plant having a construct of the invention to a second, plant lacking the construct. Therefore, the current invention not only encompasses a plant directly regenerated from cells which have been transformed in accordance with the current invention, but also the progeny of said plant. As used herein the term "progeny" denotes the offspring of any generation of a parent plant prepared in accordance with the instant invention. "Crossing" a plant to provide a plant line having one or more added transgenes relative to a starting plant line, as disclosed herein, is defined as the techniques that result in a transgene of the invention being introduced into a plant line by crossing a starting line with a donor plant line that comprises a transgene of the invention. To achieve this one would, generally, perform the following steps:

(a) plant seeds of the first (starting line) and second (donor plant line that comprises a transgene of the invention) parent plants;

(b) grow the seeds of the first and second parent plants into plants that bear flowers;

(c) pollinate the female flower of the first parent plant with the pollen of the second parent plant; and (d) harvest seeds produced on the parent plant bearing the female flower.

Backcross conversion is herein defined as the process including the steps of:

(a) crossing a plant of a first genotype containing a desired gene, DNA sequence or element to a plant of a second genotype lacking said desired gene, DNA sequence or element;

(b) selecting one or more progeny plant containing the desired gene, DNA sequence or element;

(c) crossing the progeny plant to a plant of the second genotype; and (d) repeating steps (b) and (c) for the purpose of transferring said desired gene, DNA sequence or element from a plant of a first genotype to a plant of a second genotype.

Introgression of a DNA element into a plant genotype is defined as the result of the process of backcross conversion. A plant genotype into which a DNA sequence has been introgressed may be referred to as a backcross converted genotype, line, inbred, or hybrid. Similarly a plant genotype lacking said desired DNA sequence may be referred to as an unconverted genotype, line, inbred, or hybrid.

VIII. Plant Transgene Compositions

A particularly important advance of the present invention is that it provides improved methods for expressing transgenes including marker genes and others. Such transgenes will often be genes that direct the expression of a particular protein or polypeptide product, but they may also be non-expressible DNA segments, e.g., transposons such as Ds that do no direct their own transposition. As used herein, an "expressible gene" is any gene that is capable of being transcribed into RNA (e.g., mRNA, antisense RNA, etc.) or translated into a protein, expressed as a trait of interest, or the like, etc., and is not limited to selectable, screenable or non-selectable marker genes. The invention also contemplates that, where both an expressible gene that is not necessarily a marker gene is employed in combination with a marker gene, one may employ the separate genes on either the same or different DNA segments for transformation. In the latter case, the different vectors are delivered concurrently to recipient cells to maximize cotransformation.

The choice of the particular DNA segments to be delivered to the recipient cells will often depend on the purpose of the transformation. One of the major purposes of transformation of crop plants is to add some commercially desirable, agronomically important traits to the plant. Such traits include, but are not limited to, herbicide resistance or tolerance; insect resistance or tolerance; disease resistance or tolerance (viral, bacterial, fungal, nematode); stress tolerance and/or resistance, as exemplified by resistance or tolerance to drought, heat, chilling, freezing, excessive moisture, salt stress; oxidative stress; increased yields; food content and makeup; physical appearance; male sterility; drydown; standability; prolificacy; starch properties; oil quantity and quality; and the like. One may desire to incorporate one or more genes conferring any such desirable trait or traits, such as, for example, a gene or genes encoding herbicide resistance.

In certain embodiments, the present invention contemplates the transformation of a recipient cell with more than one advantageous transgene. Two or more transgenes can be supplied in a single transformation event using either distinct transgene-encoding vectors, or using a single vector incorporating two or more gene coding sequences. Of course, any two or more transgenes of any description, such as those conferring herbicide, insect, disease (viral, bacterial, fungal, nematode) or drought resistance, male sterility, drydown, standability, prolificacy, starch properties, oil quantity and quality, or those increasing yield or nutritional quality may be employed as desired.

It is well known in the art that virtually any DNA composition may be introduced with any given transformation technique to ultimately produce fertile transgenic plants. The construction of vectors which may be employed in conjunction with the present invention will be known to those of skill of the art in light of the present disclosure (see for example, Sambrook et al., 1989; Gelvin et al., 1990). The techniques of the current invention are thus not limited to any particular DNA sequences. For example, DNA segments in the form of vectors and plasmids, or linear DNA fragments, in some instances containing only the DNA element to be expressed in the plant, and the like, may be employed.

In certain embodiments, it is contemplated that one may wish to employ replication-competent viral vectors in monocot transformation. Such vectors include, for example, wheat dwarf virus (WDV) "shuttle" vectors, such as pW1-11 and PW1-GUS (Ugaki et al., 1991). These vectors are capable of autonomous replication in maize cells as well as E. coli, and as such may provide increased sensitivity for detecting DNA delivered to transgenic cells. A replicating vector also may be useful for delivery of genes flanked by DNA sequences from transposable elements such as Ac, Ds, or Mu. It has been proposed (Laufs et al., 1990) that transposition of these elements within the maize genome requires DNA replication. It also is contemplated that transposable elements would be useful for introducing DNA fragments lacking elements necessary for selection and maintenance of the plasmid vector in bacteria, e.g., antibiotic resistance genes and origins of DNA replication. It also is proposed that use of a transposable element such as Ac, Ds, or Mu would actively promote integration of the desired DNA and hence increase the frequency of stably transformed cells.

It further is contemplated that one may wish to co-transform plants or plant cells with 2 or more vectors. Co-transformation may be achieved using a vector containing the marker and another gene or genes of interest. Alternatively, different vectors, e.g., plasmids, may contain the different genes of interest, and the plasmids may be concurrently delivered to the recipient cells. Using this method, the assumption is made that a certain percentage of cells in which the marker has been introduced, have also received the other gene(s) of interest. Thus, not all cells selected by means of the marker, will express the other genes of interest which had been presented to the cells concurrently.

Vectors, plasmids, cosmids, YACs (yeast artificial chromosomes), BACs (bacterial artificial chromosomes) and other DNA segments for use in transforming plant cells will, of course, generally comprise the cDNA, gene or genes which one desires to introduce into the cells. These DNA constructs can further include structures such as promoters, enhancers, polylinkers, or even regulatory genes as desired. The DNA segment or gene chosen for cellular introduction will often encode a protein which will be expressed in the resultant recombinant cells, such as will result in a screenable or selectable trait and/or which will impart an improved phenotype to the regenerated plant. However, this may not always be the case, and the present invention also encompasses transgenic plants incorporating non-expressed transgenes. Preferred components likely to be included with vectors used in the current invention are as follows.

(i) Regulatory Elements

Constructs prepared in accordance with the current invention will generally include a promoter which limits gene silencing in maize or another moncot. As such, this promoter will be isolated from a species other than the monocot in which transgene expression is desired. Preferred constructs will generally include a promoter from the genus Coix. The promoters may be isolated de novo from Coix, or alternatively, may be isolated based on data from known genes or promoters. Examples of known monocot genes and promoters deemed to be particularly useful for the isolation of promoters from Coix have been specifically disclosed herein above.

In addition to promoters, other types of elements can regulate gene expression. One such element is the DNA sequence between the transcription initiation site and the start of the coding sequence, termed the untranslated leader sequence. The leader sequence can influence gene expression and compilations of leader sequences have been made to predict optimum or sub-optimum sequences and generate "consensus" and preferred leader sequences (Joshi, 1987). Preferred leader sequences are contemplated to include those which have sequences predicted to direct optimum expression of the attached gene, i.e., to include a preferred consensus leader sequence which may increase or maintain mRNA stability and prevent inappropriate initiation of translation. The choice of such sequences will be known to those of skill in the art in light of the present disclosure. Sequences that are derived from genes that are highly expressed in plants, and in maize in particular, will be most preferred.

Transcription enhancers or duplications of enhancers could be used to increase expression. These enhancers often are found 5' to the start of transcription in a promoter that functions in eukaryotic cells, but can often be inserted in the forward or reverse orientation 5' or 3' to the coding sequence. In some instances, these 5' enhancing elements are introns. Examples of enhancers include elements from the CaMV 35S promoter, octopine synthase genes (Ellis et al., 1987), the rice actin 1 gene, the maize alcohol dehydrogenase gene, the maize shrunken 1 gene and promoters from non-plant eukaryotes (e.g. yeast; Ma et al., 1988).

Specifically contemplated for use in accordance with the present invention are vectors which include the ocs enhancer element. This element was first identified as a 16 bp palindromic enhancer from the octopine synthase (ocs) gene of Agrobacterium (Ellis et al., 1987), and is present in at least 10 other promoters (Bouchez et al., 1989). It is proposed that the use of an enhancer element, such as the ocs element and particularly multiple copies of the element, may be used to increase the level of transcription from adjacent promoters when applied in the context of monocot transformation.

It is contemplated that introduction of large DNA sequences comprising more than one gene may be desirable. Introduction of such sequences may be facilitated by use of bacterial or yeast artificial chromosomes (BACs or YACs, respectively), or even plant artificial chromosomes. For example, the use of BACs for Agrobacterium-mediated transformation was disclosed by Hamilton et al. (1996).

Ultimately, the most desirable DNA segments for introduction into a monocot genome may be homologous genes or gene families which encode a desired trait (for example, increased yield per acre), and which are introduced under the control of novel promoters or enhancers in accordance with the present invention. Tissue specific regulatory regions may be particularly useful in this respect. Indeed, it is envisioned that a particular use of the present invention may be the production of transformants comprising a transgene which is targeted in a tissue-specific manner. For example, insect resistant genes may be expressed specifically in the whorl and collar/sheath tissues which are targets for the first and second broods, respectively, of European Corn Borer (ECB). Likewise, genes encoding proteins with particular activity against rootworm may be targeted directly to root tissues. In addition, expression of certain genes which affect the nutritional composition of the grain must be targeted to the seed, e.g., endosperm or embryo.

Vectors for use in tissue-specific targeting of gene expression in transgenic plants typically will include tissue-specific promoters and may also include other tissue-specific control elements such as enhancer sequences. Promoters which direct specific or enhanced expression in certain plant tissues in accordance with the invention will be known to those of skill in the art in light of the present disclosure.

It is also contemplated that tissue specific expression may be functionally accomplished by introducing a constitutively expressed gene (all tissues) in combination with an antisense gene that is expressed only in those tissues where the gene product is not desired. For example, a gene coding for the crystal toxin protein from *B. thuringiensis* (*Bt*) may be introduced such that it is expressed in all tissues using a constitutive promoter, for example with an actin promoter from Coix. Furthermore, it is contemplated that promoters combining elements from more than one promoter may be useful. For example, U.S. Pat. No. 5,491,288 discloses combining a Cauliflower Mosaic Virus promoter with a histone promoter. Expression of an antisense transcript of the *Bt* gene in a maize kernel, using for example a zein promoter, would prevent accumulation of the *Bt* protein in seed. Hence the protein encoded by the introduced gene would be present in all tissues except the kernel.

Alternatively, one may wish to obtain novel tissue-specific promoter sequences from Coix for use in accordance with the present invention. To achieve this, one may first isolate cDNA clones from the tissue concerned and identify those clones which are expressed specifically in that tissue, for example, using Northern blotting. Ideally, one would like to identify a gene that is not present in a high copy number, but which gene product is relatively abundant in specific tissues. The promoter and control elements of corresponding genomic clones may then be localized using the techniques of molecular biology known to those of skill in the art.

Another useful method for identifying tissue-specific promoters is differential display (see, e.g., U.S. Pat. No. 5,599,672, the disclosure of which is specifically incorporated herein by reference in its entirety). In differential display, mRNAs are compared from different tissue types. By identifying mRNA species which are present in only a particular tissue type, or set of tissues types, one can identify the corresponding genes which are expressed is a tissue specific manner. The RNAs can be transcribed by reverse transcriptase to produce a cDNA, and the cDNA in turn be used to isolate clones containing the full-length genes. As specifically disclosed herein, the cDNA can also be used to isolate homeologous or homologous promoters, enhancers or terminators from the respective gene using, for example, suppression PCR.

It is contemplated that expression of some genes in transgenic plants will be desired only under specified conditions. For example, it is proposed that expression of certain genes that confer resistance to environmental stress factors such as drought will be desired only under actual stress conditions. It further is contemplated that expression of such genes throughout a plants development may have detrimental effects. It is known that a large number of genes exist that respond to the environment. For example, expression of some genes such as rbcS, encoding the small subunit of ribulose bisphosphate carboxylase, are regulated by light as mediated through phytochrome. Other genes are induced by secondary stimuli. For example, synthesis of abscisic acid (ABA) is induced by certain environmental factors, including but not limited to water stress. A number of genes have been shown to be induced by ABA (Skriver and Mundy, 1990). It also is anticipated that expression of genes conferring resistance to insect predation would be desired only under conditions of actual insect infestation. Therefore, for some desired traits, inducible expression of genes in transgenic plants will be desired.

It is proposed that, in some embodiments of the present invention, expression of a gene in a transgenic plant will be desired only in a certain time period during the development of the plant. Developmental timing frequently is correlated with tissue specific gene expression. For example, expression of zein storage proteins is initiated in the endosperm about 10 days after pollination.

It also is contemplated that it may be useful to target DNA itself within a cell. For example, it may be useful to target introduced DNA to the nucleus as this may increase the frequency of transformation. Within the nucleus itself it would be useful to target a gene in order to achieve site specific integration. For example, it would be useful to have a gene introduced through transformation replace an existing gene in the cell.

(ii) Terminators

Constructs will typically include the gene of interest along with a 3' end DNA sequence that acts as a signal to terminate transcription and allow for the poly-adenylation of the resultant mRNA. The most preferred 3' elements are contemplated to be those from the nopaline synthase gene of *Agrobacterium tumefaciens* (nos 3' end) (Bevan et al., 1983), the terminator for the T7 transcript from the octopine synthase gene of *Agrobacterium tumefaciens*, and the 3' end of the protease inhibitor I or II genes from potato or tomato. Regulatory elements such as Adh intron 1(Callis et al., 1987), sucrose synthase intron (Vasil et al., 1989) or TMV omega element (Gallie, et al., 1989), may further be included where desired. Alternatively, the terminator may be isolated in accordance with the invention from Coix, as described above for promoter sequences.

Particularly preferred terminators are those which have been isolated from Coix. For example, the gamma coixin terminators and Coix oleosin 3 terminators. The cloning of these terminators is described below, in Example 2 and Example 3. Nucleic acid sequences of the gamma coixin and oleosin 3 terminators is given in, for example, SEQ ID NO:11 and SEQ ID NO:17, respectively.

(iii) Transit or signal peptides.

Sequences that are joined to the coding sequence of the resistance gene, which are removed post-translationally from the initial translation product and which facilitate the transport of the protein into or through intracellular or extracellular membranes are termed transit (usually into vacuoles, vesicles, plastids and other intracellular organelles) and signal sequences (usually to the endoplasmic reticulum, golgi apparatus and outside of the cellular membrane). By facilitating the transport of the protein into compartments inside and outside the cell, these sequences may increase the accumulation of gene product protecting them from proteolytic degradation. These sequences also allow for additional mRNA sequences from highly expressed genes to be attached to the coding sequence of the genes. Since mRNA being translated by ribosomes is more stable than naked mRNA, the presence of translatable mRNA in front of the gene may increase the overall stability of the mRNA transcript from the gene and thereby increase synthesis of the gene product. Since transit and signal sequences are usually post-translationally removed from the initial translation product, the use of these sequences allows for the addition of extra translated sequences that may not appear on the final polypeptide. It is further contemplated that targeting of certain proteins may be desirable in order to enhance the stability of the protein (U.S. Pat. No. 5,545,818, incorporated herein by reference in its entirety).

Additionally, vectors may be constructed and employed in the intracellular targeting of a specific gene product within the cells of a transgenic plant or in directing a protein to the extracellular environment. This generally will be achieved by joining a DNA sequence encoding a transit or signal peptide sequence to the coding sequence of a particular gene. The resultant transit, or signal, peptide will transport the protein to a particular intracellular, or extracellular destination, respectively, and will then be post-translationally removed.

A particular example of such a use concerns the direction of a protein conferring herbicide resistance, such as the mutant EPSPS protein, to a particular organelle such as the chloroplast rather than to the cytoplasm. This is exemplified by the use of the rbcS transit peptide, the chloroplast transit peptide described in U.S. Pat. No. 5,728,925, or the optimized transit peptide described in U.S. Pat. No. 5,510,471, which confers plastid-specific targeting of proteins. In addition, it may be desirable to target certain genes responsible for male sterility to the mitochondria, or to target certain genes for resistance to phytopathogenic organisms to the extracellular spaces, or to target proteins to the vacuole. A further use concerns the direction of enzymes involved in amino acid biosynthesis or oil synthesis to the plastid. Such enzymes include dihydrodipicolinic acid synthase which may contribute to increasing lysine content of a feed.

(iv) Marker Genes

In order to improve the ability to identify transformants, one may employ a selectable or screenable marker gene as, or in addition to, the expressible gene of interest. "Marker genes" are genes that impart a distinct phenotype to cells expressing the marker gene and thus allow such transformed cells to be distinguished from cells that do not have the marker. Such genes may encode either a selectable or screenable marker, depending on whether the marker confers a trait which one can "select" for by chemical means, i.e., through the use of a selective agent (e.g., a herbicide, antibiotic, or the like), or whether it is simply a trait that one can identify through observation or testing, i.e., by "screening" (e.g., the green fluorescent protein). Of course, many examples of suitable marker genes are known to the art and can be employed in the practice of the invention.

Included within the terms selectable or screenable marker genes are also genes which encode a "secretable marker" whose secretion can be detected as a means of identifying or selecting for transformed cells. Examples include markers which encode a secretable antigen that can be identified by antibody interaction, or even secretable enzymes which can be detected by their catalytic activity. Secretable proteins fall into a number of classes, including small, diffusible proteins detectable, e.g., by ELISA; small active enzymes detectable in extracellular solution (e.g., ($\alpha$-amylase, $\beta$-lactamase, phosphinothricin acetyltransferase); and proteins that are inserted or trapped in the cell wall (e.g., proteins that include a leader sequence such as that found in the expression unit of extensin or tobacco PR-S).

With regard to selectable secretable markers, the use of a gene that encodes a protein that becomes sequestered in the cell wall, and which protein includes a unique epitope is considered to be particularly advantageous. Such a secreted antigen marker would ideally employ an epitope sequence that would provide low background in plant tissue, a promoter-leader sequence that would impart efficient expression and targeting across the plasma membrane, and would produce protein that is bound in the cell wall and yet accessible to antibodies. A normally secreted wall protein modified to include a unique epitope would satisfy all such requirements.

One example of a protein suitable for modification in this manner is extensin, or hydroxyproline rich glycoprotein (HPRG). The use of maize HPRG (Steifel et al., 1990) is preferred, as this molecule is well characterized in terms of molecular biology, expression and protein structure. However, any one of a variety of extensins and/or glycine-rich wall proteins (Keller et al., 1989) could be modified by the addition of an antigenic site to create a screenable marker.

One exemplary embodiment of a secretable screenable marker concerns the use of a maize sequence encoding the wall protein HPRG, modified to include a 15 residue epitope from the pro-region of murine interleukin-1-β (IL-1-β). However, virtually any detectable epitope may be employed in such embodiments, as selected from the extremely wide variety of antigen:antibody combinations known to those of skill in the art. The unique extracellular epitope, whether derived from IL-1β or any other protein or epitopic substance, can then be straightforwardly detected using antibody labeling in conjunction with chromogenic or fluorescent adjuncts.

1. Selectable Markers

Many selectable marker genes may be used in connection with the present invention including, but not limited to, a neo gene (Potrykus et al., 1985) which codes for kanamycin resistance and can be selected for using kanamycin, G418, paromomycin, etc.; a bar gene which confers bialaphos resistance; a mutant EPSP synthase protein (Hinchee et al., 1988) conferring glyphosate resistance; a nitrilase gene such as bxn from *Klebsiella ozaenae* which confers resistance to bromoxynil (Stalker et al., 1988); a mutant acetolactate synthase gene (ALS) which confers resistance to imidazolinone, sulfonylurea or other ALS inhibiting chemicals (European Patent Application 154,204, 1985); a methotrexate resistant DHFR gene (Thillet et al., 1988), a dalapon dehalogenase gene that confers resistance to the herbicide dalapon; or a mutated anthranilate synthase gene that confers resistance to 5-methyl tryptophan. Where a mutant EPSP synthase gene is employed, additional benefit may be realized through the incorporation of a suitable chloroplast transit peptide, CTP (U.S. Pat. No. 5,188,642) or OTP (U.S. Pat. No. 5,633,448) and use of a modified maize EPSPS gene (PCT Application WO 97/04103).

An illustrative embodiment of selectable marker genes capable of being used in systems to select transformants are the genes that encode the enzyme phosphinothricin acetyltransferase, such as the bar gene from *Streptomyces hygroscopicus* or the pat gene from *Streptomyces viridochromogenes*. The enzyme phosphinothricin acetyl transferase (PAT) inactivates the active ingredient in the herbicide bialaphos, phosphinothricin (PPT). PPT inhibits glutamine synthetase, (Murakami et al., 1986; Twell et al., 1989) causing rapid accumulation of ammonia and cell death.

Where one desires to employ a bialaphos resistance gene in the practice of the invention, the inventor has discovered that particularly useful genes for this purpose are the bar or pat genes obtainable from species of *Streptomyces* (e.g, ATCC No. 21,705). The cloning of the bar gene has been described (Murakami et al., 1986; Thompson et al., 1987) as has the use of the bar gene in the context of plants (De Block et al., 1987; De Block et al., 1989; U.S. Pat. No. 5,550,318).

2. Screenable Markers

Screenable markers that may be employed include a β-glucuronidase or uidA gene (GUS) which encodes an enzyme for which various chromogenic substrates are known; an R-locus gene, which encodes a product that regulates the production of anthocyanin pigments (red color) in plant tissues (Dellaporta et al., 1988); a β-lactamase gene (Sutcliffe, 1978), which encodes an enzyme for which various chromogenic substrates are known (e.g., PADAC, a chromogenic cephalosporin); a xylE gene (Zukowsky et al., 1983) which encodes a catechol dioxygenase that can convert chromogenic catechols; an α-amylase gene (Ikuta et al., 1990); a tyrosinase gene (Katz et al., 1983) which encodes an enzyme capable of oxidizing tyrosine to DOPA and dopaquinone which in turn condenses to form the easily-detectable compound melanin; a β-galactosidase gene, which encodes an enzyme for which there are chromogenic substrates; a luciferase (lux) gene (Ow et al., 1986), which allows for bioluminescence detection; an aequorin gene (Prasher et al., 1985) which may be employed in calcium-sensitive bioluminescence detection; or a gene encoding for green fluorescent protein (Sheen et al., 1995; Haseloff et al., 1997; Reichel et al., 1996; Tian et al., 1997; WO 97/41228).

Genes from the maize R gene complex are contemplated to be particularly useful as screenable markers. The R gene complex in maize encodes a protein that acts to regulate the production of anthocyanin pigments in most seed and plant tissue. Maize strains can have one, or as many as four, R alleles which combine to regulate pigmentation in a developmental and tissue specific manner. Thus, an R gene introduced into such cells will cause the expression of a red pigment and, if stably incorporated, can be visually scored as a red sector. If a maize line carries dominant alleles for genes encoding for the enzymatic intermediates in the anthocyanin biosynthetic pathway (C2, A1, A2, Bz1 and Bz2), but carries a recessive allele at the R locus, transformation of any cell from that line with R will result in red pigment formation. Exemplary lines include Wisconsin 22 which contains the rg-Stadler allele and TR112, a K55 derivative which is r-g, b, P1. Alternatively, any genotype of maize can be utilized if the C1 and R alleles are introduced together.

It is further proposed that R gene regulatory regions may be employed in chimeric constructs in order to provide mechanisms for controlling the expression of chimeric genes. More diversity of phenotypic expression is known at the R locus than at any other locus (Coe et al., 1988). It is contemplated that regulatory regions obtained from regions 5' to the structural R gene would be valuable in directing the expression of genes for, e.g., insect resistance, herbicide tolerance or other protein coding regions. For the purposes of the present invention, it is believed that any of the various R gene family members may be successfully employed (e.g., P, S, Lc, etc.). However, the most preferred will generally be Sn (particularly Sn:bol3). Sn is a dominant member of the R gene complex and is functionally similar to the R and B loci in that Sn controls the tissue specific deposition of anthocyanin pigments in certain seedling and plant cells, therefore, its phenotype is similar to R.

A further screenable marker contemplated for use in the present invention is firefly luciferase, encoded by the lux gene. The presence of the lux gene in transformed cells may be detected using, for example, X-ray film, scintillation counting, fluorescent spectrophotometry, low-light video cameras, photon counting cameras or multiwell luminometry. It also is envisioned that this system may be developed for populational screening for bioluminescence, such as on tissue culture plates, or even for whole plant screening. The gene which encodes green fluorescent protein is contemplated as a particularly useful reporter (Sheen et al., 1995; Haseloff et al., 1997; Reichel et al., 1996; Tian et al., 1997; WO 97/41228). Expression of green fluorescent protein may be visualized in a cell or plant as fluorescence following illumination by particular wavelengths of light.

(v) Transgenes for Modification of Monocots

A particularly important advance of the present invention is that it provides methods and compositions for the efficient expression in plant cells of genes in addition to, or other than, marker genes. Such transgenes often will be genes that direct the expression of a particular protein or polypeptide product, but they may also be non-expressible DNA segments, e.g., transposons such as Ds that do not direct their own transposition. As used herein, an "expressible gene" is any gene that is capable of being transcribed into RNA (e.g., mRNA, antisense RNA, etc.) or translated into a protein, expressed as a trait of interest, or the like, etc., and is not limited to selectable, screenable or non-selectable marker genes. The invention also contemplates that, where both an expressible gene that is not necessarily a marker gene is employed in combination with a marker gene, one may employ the separate genes on either the same or different DNA segments for transformation. In the latter case, the different vectors are delivered concurrently to recipient cells to maximize cotransformation.

The choice of the particular DNA segments to be delivered to the recipient cells often will depend on the purpose of the transformation. One of the major purposes of transformation of crop plants is to add some commercially desirable, agronomically important traits to the plant. Such traits include, but are not limited to, herbicide resistance or tolerance; insect resistance or tolerance; disease resistance or tolerance (viral, bacterial, fungal, nematode); stress tolerance and/or resistance, as exemplified by resistance or tolerance to drought, heat, chilling, freezing, excessive moisture, salt stress; oxidative stress; increased yields; food content and makeup; physical appearance; male sterility; drydown; standability; prolificacy; starch quantity and quality; oil quantity and quality; protein quality and quantity; amino acid composition; and the like. One may desire to incorporate one or more genes conferring any such desirable trait or traits, such as, for example, a gene or genes encoding herbicide resistance.

In certain embodiments, the present invention contemplates the transformation of a recipient cell with more than one exogenous gene. As used herein, an "exogenous gene," is a gene not normally found in the host genome in an identical context. By this, it is meant that the gene may be isolated from a different species than that of the host genome, or alternatively, isolated from the host genome but operably linked to one or more regulatory regions which differ from those found in the unaltered, native gene. Two or more exogenous genes also can be supplied in a single transformation event using either distinct transgene-encoding vectors, or using a single vector incorporating two or more gene coding sequences. For example, plasmids bearing the bar and aroA expression units in either convergent, divergent, or colinear orientation, are considered to be particularly useful. Further preferred combinations are those of an insect resistance gene, such as a *Bt* gene, along with a protease inhibitor gene such as pinII, or the use of bar in combination with either of the above genes. Of course, any two or more transgenes of any description, such as those conferring herbicide, insect, disease (viral, bacterial, fungal, nematode) or drought resistance, male sterility, drydown, standability, prolificacy, starch properties, oil quantity and quality, or those increasing yield or nutritional quality may be employed as desired.

1. Herbicide Resistance

The genes encoding phosphinothricin acetyltransferase (bar and pat), glyphosate tolerant EPSP synthase genes, the glyphosate degradative enzyme gene gox encoding glyphosate oxidoreductase, deh (encoding a dehalogenase enzyme that inactivates dalapon), herbicide resistant (e.g., sulfonylurea and imidazolinone) acetolactate synthase, and bxn genes (encoding a nitrilase enzyme that degrades bromoxynil) are good examples of herbicide resistant genes for use in transformation. The bar and pat genes code for an enzyme, phosphinothricin acetyltransferase (PAT), which inactivates the herbicide phosphinothricin and prevents this compound from inhibiting glutamine synthetase enzymes. The enzyme 5-enolpyruvylshikimate 3-phosphate synthase (EPSP Synthase), is normally inhibited by the herbicide N-(phosphonomethyl)glycine (glyphosate). However, genes are known that encode glyphosate-resistant EPSP synthase enzymes. These genes are particularly contemplated for use in monocot transformation. The deh gene encodes the enzyme dalapon dehalogenase and confers resistance to the herbicide dalapon. The bxn gene codes for a specific nitrilase enzyme that converts bromoxynil to a non-herbicidal degradation product.

2. Insect Resistance

Potential insect resistance genes that can be introduced include *Bacillus thuringiensis* crystal toxin genes or *Bt* genes (Watrud et al., 1985). *Bt* genes may provide resistance to lepidopteran or coleopteran pests such as European Corn Borer (ECB). Preferred *Bt* toxin genes for use in such embodiments include the CryIA(b) and CryIA(c) genes. Endotoxin genes from other species of *B. thuringiensis* which affect insect growth or development may also be employed in this regard.

It is contemplated that preferred *Bt* genes for use in the transformation protocols disclosed herein will be those in which the coding sequence has been modified to effect increased expression in plants, and more particularly, in maize. Means for preparing synthetic genes are well known in the art and are disclosed in, for example, U.S. Pat. No. 5,500,365 and U.S. Pat. No. 5,689,052, each of the disclosures of which are specifically incorporated herein by reference in their entirety. Examples of such modified *Bt* toxin genes include a synthetic *Bt* CryIA(b) gene (Perlak et al., 1991), and the synthetic CryIA(c) gene termed 1800b (PCT Application WO 95/06128). Some examples of other *Bt* toxin genes known to those of skill in the art are given in Table 3 below.

TABLE 3

*Bacillus thuringiensis* δ-Endotoxin Genes[a]

| New Nomenclature | Old Nomenclature | GenBank Accession # |
| --- | --- | --- |
| Cry1Aa | CryIA(a) | M11250 |
| Cry1Ab | CryIA(b) | M13898 |
| Cry1Ac | CryIA(c) | M11068 |
| Cry1Ad | CryIA(d) | M73250 |
| Cry1Ae | CryIA(e) | M65252 |
| Cry1Ba | CryIB | X06711 |
| Cry1Bb | ET5 | L32020 |
| Cry1Bc | PBG5 | Z46442 |
| Cry1Bd | CryE1 | U70726 |
| Cry1Ca | CryIC | X07518 |
| Cry1Cb | CryIC(b) | M97880 |
| Cry1Da | CryID | X54160 |
| Cry1Db | PrtB | Z22511 |
| Cry1Ea | CryIE | X53985 |
| Cry1Eb | CryIE(b) | M73253 |
| Cry1Fa | CryIF | M63897 |
| Cry1Fb | PrtD | Z22512 |
| Cry1Ga | PrtA | Z22510 |
| Cry1Gb | CryH2 | U70725 |
| Cry1Ha | PrtC | Z22513 |
| Cry1Hb | | U35780 |
| Cry1Ia | CryV | X62821 |
| Cry1Ib | CryV | U07642 |
| Cry1Ja | ET4 | L32019 |
| Cry1Jb | ET1 | U31527 |
| Cry1K | | U28801 |
| Cry2Aa | CryIIA | M31738 |
| Cry2Ab | CryIIB | M23724 |
| Cry2Ac | CryIIC | X57252 |
| Cry3A | CryIIIA | M22472 |
| Cry3Ba | CryIIIB | X17123 |
| Cry3Bb | CryIIIB2 | M89794 |
| Cry3C | CryIIID | X59797 |

TABLE 3-continued

*Bacillus thuringiensis* δ-Endotoxin Genes[a]

| New Nomenclature | Old Nomenclature | GenBank Accession # |
|---|---|---|
| Cry4A | CryIVA | Y00423 |
| Cry4B | CryIVB | X07423 |
| Cry5Aa | CryVA(a) | L07025 |
| Cry5Ab | CryVA(b) | L07026 |
| Cry6A | CryVIA | L07022 |
| Cry6B | CryVIB | L07024 |
| Cry7Aa | CryIIIC | M64478 |
| Cry7Ab | CryIIICb | U04367 |
| Cry8A | CryIIIE | U04364 |
| Cry8B | CryIIIG | U04365 |
| Cry8C | CryIIIF | U04366 |
| Cry9A | CryIG | X58120 |
| Cry9B | CryIX | X75019 |
| Cry9C | CryIH | Z37527 |
| Cry10A | CryIVC | M12662 |
| Cry11A | CryIVD | M31737 |
| Cry11B | Jeg80 | X86902 |
| Cry12A | CryVB | L07027 |
| Cry13A | CryVC | L07023 |
| Cry14A | CryVD | U13955 |
| Cry15A | 34kDa | M76442 |
| Cry16A | cbm71 | X94146 |
| Cry17A | cbm71 | X99478 |
| Cry18A | CryBP1 | X99049 |
| Cry19A | Jeg65 | Y08920 |
| Cyt1Aa | CytA | X03182 |
| Cyt1Ab | CytM | X98793 |
| Cyt2A | CytB | Z14147 |
| Cyt2B | CytB | U52043 |

[a]Adapted from: http://epunix.biols.susx.ac.uk/Home/Neil_Crickmore/Bt/index.html Protease inhibitors also may provide insect resistance (Johnson et al., 1989), and will thus have utility in plant transformation. The use of a protease inhibitor II gene, pinII, from tomato or potato is envisioned to be particularly useful. Even more advantageous is the use of a pinII gene in combination with a *Bt* toxin gene, the combined effect of which has been discovered to produce synergistic insecticidal activity. Other genes which encode inhibitors of the insect's digestive system, or those that encode enzymes or co-factors that facilitate the production of inhibitors, also may be useful. This group may be exemplified by oryzacystatin and amylase inhibitors such as those from wheat and barley.

Also, genes encoding lectins may confer additional or alternative insecticide properties. Lectins (originally termed phytohemagglutinins) are multivalent carbohydrate-binding proteins which have the ability to agglutinate red blood cells from a range of species. Lectins have been identified recently as insecticidal agents with activity against weevils, ECB and rootworm (Murdock et al., 1990; Czapla & Lang, 1990). Lectin genes contemplated to be useful include, for example, barley and wheat germ agglutinin (WGA) and rice lectins (Gatehouse et al., 1984), with WGA being preferred.

Genes controlling the production of large or small polypeptides active against insects when introduced into the insect pests, such as, e.g., lytic peptides, peptide hormones and toxins and venoms, form another aspect of the invention. For example, it is contemplated that the expression of juvenile hormone esterase, directed towards specific insect pests, may also result in insecticidal activity, or perhaps cause cessation of metamorphosis (Hammock et al., 1990).

Transgenic maize expressing genes which encode enzymes that affect the integrity of the insect cuticle form yet another aspect of the invention. Such genes include those encoding, e.g., chitinase, proteases, lipases and also genes for the production of nikkomycin, a compound that inhibits chitin synthesis, the introduction of any of which is contemplated to produce insect resistant maize plants. Genes that code for activities that affect insect molting, such as those affecting the production of ecdysteroid UDP-glucosyl transferase, also fall within the scope of the useful transgenes of the present invention.

Genes that code for enzymes that facilitate the production of compounds that reduce the nutritional quality of the host plant to insect pests are also encompassed by the present invention. It may be possible, for instance, to confer insecticidal activity on a plant by altering its sterol composition. Sterols are obtained by insects from their diet and are used for hormone synthesis and membrane stability. Therefore alterations in plant sterol composition by expression of novel genes, e.g., those that directly promote the production of undesirable sterols or those that convert desirable sterols into undesirable forms, could have a negative effect on insect growth and/or development and hence endow the plant with insecticidal activity. Lipoxygenases are naturally occurring plant enzymes that have been shown to exhibit anti-nutritional effects on insects and to reduce the nutritional quality of their diet. Therefore, further embodiments of the invention concern transgenic plants with enhanced lipoxygenase activity which may be resistant to insect feeding.

*Tripsacum dactyloides* is a species of grass that is resistant to certain insects, including corn root worm. It is anticipated that genes encoding proteins that are toxic to insects or are involved in the biosynthesis of compounds toxic to insects will be isolated from Tripsacum and that these novel genes will be useful in conferring resistance to insects. It is known that the basis of insect resistance in Tripsacum is genetic, because said resistance has been transferred to *Zea mays* via sexual crosses (Branson and Guss, 1972). It is further anticipated that other cereal, monocot or dicot plant species may have genes encoding proteins that are toxic to insects which would be useful for producing insect resistant corn plants.

Further genes encoding proteins characterized as having potential insecticidal activity may also be used as transgenes in accordance herewith. Such genes include, for example, the cowpea trypsin inhibitor (CpTI; Hilder et al., 1987) which may be used as a rootworm deterrent; genes encoding avermectin (*Avermectin and Abamectin.*, Campbell, W. C., Ed., 1989; Ikeda et al., 1987) which may prove particularly useful as a corn rootworm deterrent; ribosome inactivating protein genes; and even genes that regulate plant structures. Transgenic maize including anti-insect antibody genes and genes that code for enzymes that can convert a non-toxic insecticide (pro-insecticide) applied to the outside of the plant into an insecticide inside the plant are also contemplated.

3. Environment or Stress Resistance

Improvement of corn's ability to tolerate various environmental stresses such as, but not limited to, drought, excess moisture, chilling, freezing, high temperature, salt, and oxidative stress, can also be effected through expression of novel genes. It is proposed that benefits may be realized in terms of increased resistance to freezing temperatures through the introduction of an "antifreeze" protein such as that of the Winter Flounder (Cutler et al., 1989) or synthetic gene derivatives thereof. Improved chilling tolerance may also be conferred through increased expression of glycerol-3-phosphate acetyltransferase in chloroplasts (Wolter et al., 1992). Resistance to oxidative stress (often exacerbated by conditions such as chilling temperatures in combination with high light intensities) can be conferred by expression of superoxide dismutase (Gupta et al., 1993), and may be improved by glutathione reductase (Bowler et al., 1992). Such strategies may allow for tolerance to freezing in newly emerged fields as well as extending later maturity higher yielding varieties to earlier relative maturity zones.

It is contemplated that the expression of novel genes that favorably effect plant water content, total water potential, osmotic potential, and turgor will enhance the ability of the plant to tolerate drought. As used herein, the terms "drought resistance" and "drought tolerance" are used to refer to a plants increased resistance or tolerance to stress induced by a reduction in water availability, as compared to normal circumstances, and the ability of the plant to function and survive in lower-water environments. In this aspect of the invention it is proposed, for example, that the expression of genes encoding for the biosynthesis of osmotically-active solutes, such as polyol compounds, may impart protection against drought. Within this class are genes encoding for mannitol-L-phosphate dehydrogenase (Lee and Saier, 1982) and trehalose-6-phosphate synthase (Kaasen et al., 1992). Through the subsequent action of native phosphatases in the cell or by the introduction and coexpression of a specific phosphatase, these introduced genes will result in the accumulation of either mannitol or trehalose, respectively, both of which have been well documented as protective compounds able to mitigate the effects of stress. Mannitol accumulation in transgenic tobacco has been verified and preliminary results indicate that plants expressing high levels of this metabolite are able to tolerate an applied osmotic stress (Tarczynski et al., 1992, 1993).

Similarly, the efficacy of other metabolites in protecting either enzyme function (e.g., alanopine or propionic acid) or membrane integrity (e.g., alanopine) has been documented (Loomis et al., 1989), and therefore expression of genes encoding for the biosynthesis of these compounds might confer drought resistance in a manner similar to or complimentary to mannitol. Other examples of naturally occurring metabolites that are osmotically active and/or provide some direct protective effect during drought and/or desiccation include fructose, erythritol (Coxson et al., 1992), sorbitol, dulcitol (Karsten et al., 1992), glucosylglycerol (Reed et al., 1984; ErdMann et al., 1992), sucrose, stachyose (Koster and Leopold, 1988; Blackman et al., 1992), raffinose (Bernal-Lugo and Leopold, 1992), proline (Rensburg et al., 1993), glycine betaine, ononitol and pinitol (Vernon and Bohnert, 1992). Continued canopy growth and increased reproductive fitness during times of stress will be augmented by introduction and expression of genes such as those controlling the osmotically active compounds discussed above and other such compounds. Currently preferred genes which promote the synthesis of an osmotically active polyol compound are genes which encode the enzymes mannitol-1-phosphate dehydrogenase, trehalose-6-phosphate synthase and myo-inositol 0-methyltransferase.

It is contemplated that the expression of specific proteins may also increase drought tolerance. Three classes of Late Embryogenic Proteins have been assigned based on structural similarities (see Dure et al., 1989). All three classes of LEAs have been demonstrated in maturing (i.e. desiccating) seeds. Within these 3 types of LEA proteins, the Type-II (dehydrin-type) have generally been implicated in drought and/or desiccation tolerance in vegetative plant parts (i.e. Mundy and Chua, 1988; Piatkowski et al., 1990; Yamaguchi-Shinozaki et al., 1992). Recently, expression of a Type-III LEA (HVA-1) in tobacco was found to influence plant height, maturity and drought tolerance (Fitzpatrick, 1993). In rice, expression of the HVA-1 gene influenced tolerance to water deficit and salinity (Xu et al., 1996). Expression of structural genes 10 from all three LEA groups may therefore confer drought tolerance. Other types of proteins induced during water stress include thiol proteases, aldolases and transmembrane transporters (Guerrero et al., 1990), which may confer various protective and/or repair-type functions during drought stress. It is also contemplated that genes that effect lipid biosynthesis and hence membrane composition might also be useful in conferring drought resistance on the plant.

Many of these genes for improving drought resistance have complementary modes of action. Thus, it is envisaged that combinations of these genes might have additive and/or synergistic effects in improving drought resistance in corn. Many of these genes also improve freezing tolerance (or resistance); the physical stresses incurred during freezing and drought are similar in nature and may be mitigated in similar fashion. Benefit may be conferred via constitutive expression of these genes, but the preferred means of expressing these novel genes may be through the use of a turgor-induced promoter (such as the promoters for the turgor-induced genes described in Guerrero et al., 1990 and Shagan et al., 1993 which are incorporated herein by reference). Spatial and temporal expression patterns of these genes may enable corn to better withstand stress.

It is proposed that expression of genes that are involved with specific morphological traits that allow for increased water extractions from drying soil would be of benefit. For example, introduction and expression of genes that alter root characteristics may enhance water uptake. It is also contemplated that expression of genes that enhance reproductive fitness during times of stress would be of significant value. For example, expression of genes that improve the synchrony of pollen shed and receptiveness of the female flower parts, i.e., silks, would be of benefit. In addition it is proposed that expression of genes that minimize kernel abortion during times of stress would increase the amount of grain to be harvested and hence be of value.

Given the overall role of water in determining yield, it is contemplated that enabling corn to utilize water more efficiently, through the introduction and expression of novel genes, will improve overall performance even when soil water availability is not limiting. By introducing genes that improve the ability of corn to maximize water usage across a full range of stresses relating to water availability, yield stability or consistency of yield performance may be realized.

4. Disease Resistance

It is proposed that increased resistance to diseases may be realized through introduction of genes into monocotyledonous plants such as maize. It is possible to produce resistance to diseases caused by viruses, bacteria, fungi and nematodes. It is also contemplated that control of mycotoxin producing organisms may be realized through expression of introduced genes.

Resistance to viruses may be produced through expression of novel genes. For example, it has been demonstrated that expression of a viral coat protein in a transgenic plant can impart resistance to infection of the plant by that virus and perhaps other closely related viruses (Cuozzo et al., 1988, Hemenway et al., 1988, Abel et al., 1986). It is contemplated that expression of antisense genes targeted at essential viral functions may impart resistance to said virus. For example, an antisense gene targeted at the gene responsible for replication of viral nucleic acid may inhibit replication and lead to resistance to the virus. It is believed that interference with other viral functions through the use of antisense genes may also increase resistance to viruses. Further, it is proposed that it may be possible to achieve resistance to viruses through other approaches, including, but not limited to the use of satellite viruses. Examples of viral and viral-like diseases, for which one could introduce resistance to in a transgenic plant in accordance with the instant invention, are listed below, in Table 4.

TABLE 4

Plant Virus and Virus-like Diseases

| DISEASE | CAUSATIVE AGENT |
| --- | --- |
| American wheat striate (wheat striate mosaic) | American wheat striate mosaic virus mosaic (AWSMV) |
| Barley stripe mosaic | Barley stripe mosaic virus (BSMV) |
| Barley yellow dwarf | Barley yellow dwarf virus (BYDV) |
| Brome mosaic | Brome mosaic virus (BMV) |
| Cereal chlorotic mottle* | Cereal chlorotic mottle virus (CCMV) |
| Corn chlorotic vein banding (Brazilian maize mosaic)[1] | Corn chlorotic vein banding virus (CCVBV) |
| Corn lethal necrosis | Virus complex (Maize chlorotic mottle virus[MCMV] and Maize dwarf mosaic virus [MDMV] A or B or Wheat streak mosaic virus[WSMV]) |
| Cucumber mosaic | Cucumber mosaic virus (CMV) |
| Cynodon chlorotic streak*,[1] | Cynodon chlorotic streak virus (CCSV) |
| Johnsongrass mosaic | Johnsongrass mosaic virus (JGMV) |
| Maize bushy stunt | Mycoplasma-like organism (MLO) associated |
| Maize chlorotic dwarf | Maize chlorotic dwarf virus (MCDV) |
| Maize chlorotic mottle | Maize chlorotic mottle virus (MCMV) |
| Maize dwarf mosaic | Maize dwarf mosaic virus (MDMV) strains A, D, E and F |
| Maize leaf fleck | Maize leaf fleck virus (MLFV) |
| Maize line* | Maize line virus (MLV) |
| Maize mosaic (corn leaf stripe, enanismo ravado) | Maize mosaic virus (MMV) |
| Maize mottle and chlorotic stunt | Maize mottle and chlorotic stunt virus* |
| Maize pellucid ringspot* | Maize pellucid ringspot virus (MPRV) |
| Maize raya gruesa*,[1] | Maize raya gruesa virus (MRGV) |
| maize rayado fino* (fine striping disease) | Maize rayado fino virus (MRFV) |
| Maize red leaf and red stripe* | Mollicute? |
| Maize red stripe* | Maize red stripe virus (MRSV) |
| Maize ring mottle* | Maize ring mottle virus (MRMV) |
| Maize rio IV* | Maize rio cuarto virus (MRCV) |
| Maize rough dwarf* (nanismo ruvido) | Maize rough dwarf virus (MRDV) (= Cereal tillering disease virus*) |
| Maize sterile stunt* | Maize sterile stunt virus (strains of barley yellow striate virus) |
| Maize streak* | Maize streak virus (MSV) |
| Maize stripe (maize chlorotic stripe, maize hoja blanca) | Maize stripe virus |
| Maize stunting*,[1] | Maize stunting virus |
| Maize tassel abortion* | Maize tassel abortion virus (MTAV) |
| Maize vein enation* | Maize vein enation virus (MVBV) |
| Maize wallaby ear* | Maize wallaby ear virus (MWEV) |
| Maize white leaf* | Maize white leaf virus |
| Maize white line mosaic | Maize white line mosaic virus (MWLMV) |
| Millet red leaf* | Millet red leaf virus (MRLV) |
| Northern cereal mosaic* | Northern cereal mosaic virus (NCMV) |
| Oat pseudorosette* (zakuklivanie) | Oat pseudorosette virus |
| Oat sterile dwarf* | Oat sterile dwarf virus (OSDV) |
| Rice black-streaked dwarf* | Rice black-streaked dwarf virus (RBSDV) |
| Rice stripe* | Rice stripe virus (RSV) |
| Sorghum mosaic | Sorghum mosaic virus (SrMV), formerly sugarcane mosaic virus (SCMV) strains H, I and M |
| Sugarcane Fiji disease* | Sugarcane Fiji disease virus (FDV) |
| Sugarcane mosaic | Sugarcane mosaic virus (SCMV) strains A, B, D, E,SC, BC, Sabi and MB (formerly MDMV-B) |
| Vein enation*,[1] | Virus? |
| Wheat spot mosaic[1] | Wheat spot mosaic virus (WSMV) |

*Not known to occur naturally on corn in the United States.
[1]Minor viral disease.

It is proposed that increased resistance to diseases caused by bacteria and fungi may be realized through introduction of novel genes. It is contemplated that genes encoding so-called "peptide antibiotics," pathogenesis related (PR) proteins, toxin resistance, and proteins affecting host-pathogen interactions such as morphological characteristics will be useful. Peptide antibiotics are polypeptide sequences which are inhibitory to growth of bacteria and other microorganisms. For example, the classes of peptides referred to as cecropins and magainins inhibit growth of many species of bacteria and fungi. It is proposed that expression of PR proteins in monocotyledonous plants such as maize may be useful in conferring resistance to bacterial disease. These genes are induced following pathogen attack on a host plant and have been divided into at least five classes of proteins (Bol, Linthorst, and Cornelissen, 1990). Included amongst the PR proteins are β-1, 3-glucanases, chitinases, and osmotin and other proteins that are believed to function in plant resistance to disease organisms. Other genes have been identified that have antifungal properties, e.g., UDA (stinging nettle lectin) and hevein (Broakaert et al., 1989; Barkai-Golan et al., 1978). It is known that certain plant diseases are caused by the production of phytotoxins. It is proposed that resistance to these diseases would be achieved through expression of a novel gene that encodes an enzyme capable of degrading or otherwise inactivating the phytotoxin. It also is contemplated that expression of novel genes that alter the interactions between the host plant and pathogen may be useful in reducing the ability of the disease organism to invade the tissues of the host plant, e.g., an increase in the waxiness of the leaf cuticle or other morphological characteristics. Examples of bacterial and fungal diseases, including downy mildews, for which one could introduce resistance to in a transgenic plant in accordance with the instant invention, are listed below, in Tables 5, 6 and 7.

TABLE 5

Plant Bacterial Diseases

| DISEASE | CAUSATIVE AGENT |
| --- | --- |
| Bacterial leaf blight and stalk rot | *Pseudomonas avenae* subsp. *avenae* |
| Bacterial leaf spot | *Xanthomonas campestris* pv. *holcicola* |
| Bacterial stalk rot | *Enterobacter dissolvens* = *Erwinia dissolvens* |
| Bacterial stalk and top rot | *Erwinia carotovora* subsp. *carotovora*, *Erwinia chrysanthemi* pv. *zeae* |
| Bacterial stripe | *Pseudomonas andropogonis* |
| Chocolate spot | *Pseudomonas syringae* pv. *coronafaciens* |
| Goss's bacterial wilt and blight (leaf freckles and wilt) | *Clavibacter michiganensis* subsp. *nebraskensis* =*Corynebacterium michiganense* pv. *nebraskense* |
| Holcus spot | *Pseudomonas syringae* pv. *syringae* |
| Purple leaf sheath | Hemiparasitic bacteria + (See under Fungi) |
| Seed rot-seedling blight | *Bacillus subtilis* |
| Stewart's disease (bacterial wilt) | *Pantoea stewartii* = *Erwinia stewartii* |
| Corn stunt (achapparramiento, maize stunt, Mesa Central or Rio Grande maize stunt) | *Spiroplasma kunkelii* |

TABLE 6

Plant Fungal Diseases

| DISEASE | PATHOGEN |
| --- | --- |
| Anthracnose leaf blight and anthracnose stalk rot | *Colletotrichum graminicola* (teleomorph: *Glomerella graminicola* Politis), *Glomerella tucumanensis* (anamorph: *Glomerella falcatum* Went) |
| Aspergillus ear and kernel rot | *Aspergillus flavus* Link: Fr. |
| Banded leaf and sheath spot* | *Rhizoctonia solani* Kühn = *Rhizoctonia microsclerotia* J. Matz (teleomorph: *Thanatephorus cucumeris*) |

TABLE 6-continued

Plant Fungal Diseases

| DISEASE | PATHOGEN |
| --- | --- |
| Black bundle disease | *Acremonium strictum* W. Gams = *Cephalosporium acremonium* Auct. non Corda |
| Black kernel rot* | *Lasiodiplodia theobromae* = *Botryodiplodia theobromae* |
| Borde blanco* | *Marasmiellus* sp. |
| Brown spot (black spot, stalk rot) | *Physoderma maydis* |
| Cephalosporium kernel rot | *Acremonium strictum* = *Cephalosporium acremonium* |
| Charcoal rot | *Macrophomina phaseolina* |
| Corticium ear rot* | *Thanatephorus cucumeris* = *Corticium sasakii* |
| Curvularia leaf spot | *Curvularia clavata*, *C. eragrostidis*, = *C. maculans* (teleomorph: *Cochliobolus eragrostidis*), *Curvularia inaequalis*, *C. intermedia* (teleomorph: *Cochliobolus intermedius*), *Curvularia lunata* (teleomorph: *Cochliobolus lunatus*), *Curvularia pallescens* (teleomorph: *Cochliobolus pallescens*), *Curvularia senegalensis*, *C. tuberculata* (teleomorph: *Cochliobolus tuberculatus*) |
| Didymella leaf spot* | *Didymella exitalis* |
| Diplodia ear rot and stalk rot | *Diplodia frumenti* (teleomorph: *Botryosphaeria festucae*) |
| Diplodia ear rot, stalk rot, seed rot and seedling blight | *Diplodia maydis* = *Stenocarpella maydis* |
| Diplodia leaf spot or leaf streak | *Stenocarpella macrospora* = *Diplodia macrospora* |

*Not known to occur naturally on corn in the United States.

TABLE 7

Plant Downy Mildews

| DISEASE | CAUSATIVE AGENT |
| --- | --- |
| Brown stripe downy mildew* | *Sclerophthora rayssiae* var. *zeae* |
| Crazy top downy mildew | *Sclerophthora macrospora* = *Sclerospora macrospora* |
| Green ear downy mildew (graminicola downy mildew) | *Sclerospora graminicola* |
| Java downy mildew* | *Peronosclerospora maydis* = *Sclerospora maydis* |
| Philippine downy mildew* | *Peronosclerospora philippinensis* = *Sclerospora philippinensis* |
| Sorghum downy mildew | *Peronosclerospora sorghi* = *Sclerospora sorghi* |
| Spontaneum downy mildew* | *Peronosclerospora spontanea* = *Sclerospora spontanea* |
| Sugarcane downy mildew* | *Peronosclerospora sacchari* = *Sclerospora sacchari* |
| Dry ear rot (cob, kernel and stalk rot) | *Nigrospora oryzae* (teleomorph: *Khuskia oryzae*) |
| Ear rots, minor | *Alternaria alternata* = *A. tenuis*, *Aspergillus glaucus*, *A. niger*, *Aspergillus* spp., *Botrytis cinerea* (teleomorph: *Botryotinia fuckeliana*), *Cunninghamella* sp., *Curvularia pallescens*, *Doratomyces stemonitis* = *Cephalotrichum stemonitis*, *Fusarium culmorum*, *Gonatobotrys simplex*, *Pithomyces maydicus*, *Rhizopus microsporus* Tiegh., *R. stolonifer* = *R. nigricans*, *Scopulariopsis brumptii* |

TABLE 7-continued

Plant Downy Mildews

| DISEASE | CAUSATIVE AGENT |
|---|---|
| Ergot* (horse's tooth, diente de caballo) | Claviceps gigantea (anamorph: Sphacelia sp.) |
| Eyespot | Aureobasidium zeae = Kabatiella zeae |
| Fusarium ear and stalk rot | Fusarium subglutinans = F. moniliforme var. subglutinans |
| Fusarium kernel, root and stalk rot, seed rot and seedling blight | Fusarium moniliforme (teleomorph: Gibberella fujikuroi) |
| Fusarium stalk rot, seedling root rot | Fusarium avenaceum (teleomorph: Gibberella avenacea) |
| Gibberella ear and stalk rot | Gibberella zeae (anamorph: Fusarium graminearum) |
| Gray ear rot | Botryosphaeria zeae = Physalospora zeae (anamorph: Macrophoma zeae) |
| Gray leaf spot (Cercospora leaf spot) | Cercospora sorghi = C. sorghi var. maydis, C. zeae-maydis |
| Helminthosporium root rot | Exserohilum pedicellatum = Helminthosporium pedicellatum (teleomorph: Setosphaeria pedicellata) |
| Hormodendrum ear rot (Cladosporium rot) | Cladosporium cladosporioides = Hormodendrum cladosporioides, C. herbarum |
| Hyalothyridium leaf spot* | Hyalothyridium maydis |
| Late wilt* | Cephalosporium maydis |
| Leaf spots, minor | Alternaria alternata, Ascochyta maydis, A. tritici, A. zeicola, Bipolaris victoriae = Helminthosporium victoriae (teleomorph: Cochliobolus victoriae), C. sativus (anamorph: Bipolaris sorokiniana = H. sorokinianum = H. sativum), Epicoccum nigrum, Exserohilum prolatum = Drechslera prolata (teleomorph: Setosphaeria prolata) Graphium penicillioides, Leptosphaeria maydis, Leptothyrium zeae, Ophiosphaerella herpotricha, (anamorph: Scolecosporiella sp.), Paraphaeosphaeria michotii, Phoma sp., Septoria zeae, S. zeicola, S. zeina |
| Northern corn leaf blight (white blast, crown stalk rot, stripe) | Setosphaeria turcica (anamorph: Exserohilum turcicum = Helminthosporium turcicum) |
| Northern corn leaf spot, Helminthosporium ear rot (race 1) | Cochliobolus carbonum (anamorph: Bipolaris zeicola = Helminthbsporium carbonum) |
| Penicillium ear rot (blue eye, blue mold) | Penicillium spp., P. chrysogenum, P. expansum, P. oxalicum |
| Phaeocytostroma stalk rot and root rot | Phaeocytostroma ambiguum, = Phaeocytosporella zeae |
| Phaeosphaeria leaf spot* | Phaeosphaeria maydis = Sphaerulina maydis |
| Physalospora ear rot (Botryosphaeria ear rot) | Botryosphaeria festucae = Physalospora zeicola (anamorph: Diplodia frumenti) |
| Purple leaf sheath | Hemiparasitic bacteria and fungi |
| Pyrenochaeta stalk rot and root rot | Phoma terrestris = Pyrenochaeta terrestris |
| Pythium root rot | Pythium spp., P. arrhenomanes, P. graminicola |
| Pythium stalk rot | Pythium aphanidermatum = P. butleri L. |
| Red kernel disease (ear mold, leaf and seed rot) | Epicoccum nigrum |
| Rhizoctonia ear rot (sclerotial rot) | Rhizoctonia zeae (teleomorph: Waitea circinata) |
| Rhizoctonia root rot and stalk rot | Rhizoctonia solani, Rhizoctonia zeae |
| Root rots, minor | Alternaria alternata, Cercospora sorghi, Dictochaeta fertilis, Fusarium acuminatum (teleomorph: Gibberella acuminata), F. equiseti (teleomorph: G. intricans), F. oxysporum, F. pallidoroseum, F. poae, F. roseum, G. cyanogena, (anamorph: F. sulphureum), Microdochium bolleyi, Mucor sp., Periconia circinata, Phytophthora cactorum, P. drechsleri, P. nicotianae var. parasitica, Rhizopus arrhizus |
| Rostratum leaf spot (Helminthosporium leaf disease, ear and stalk rot) | Setosphaeria rostrata, (anamorph: Exserohilum rostratum = Helminthosporium rostratum) |
| Rust, common corn | Puccinia sorghi |
| Rust, southern corn | Puccinia polysora |
| Rust, tropical corn | Physopella pallescens, P. zeae = Angiopsora zeae |
| Sclerotium ear rot* (southern blight) | Sclerotium rolftii Sacc. (teleomorph: Athelia rolfsii) |
| Seed rot-seedling blight | Bipolaris sorokiniana, B. zeicola = Helminthosporium carbonum, Diplodia maydis, Exserohilum pedicillatum, Exserohilum turcicum = Helminthosporium turcicum, Fusarium avenaceum, F. culmorum, F. moniliforme, Gibberella zeae (anamorph: F. graminearum), Macrophomina phaseolina, Penicillium spp., Phomopsis sp., Pythium spp., Rhizoctonia solani, R. zeae, Sclerotium rolfsii, Spicaria sp. |
| Selenophoma leaf spot* | Selenophoma sp. |
| Sheath rot | Gaeumannomyces graminis |
| Shuck rot | Myrothecium gramineum |
| Silage mold | Monascus purpureus, M. ruber |
| Smut, common | Ustilago zeae = U. maydis) |
| Smut, false | Ustilaginoidea virens |
| Smut, head | Sphacelotheca reiliana = Sporisorium holci-sorghi |
| Southern corn leaf blight and stalk rot | Cochliobolus heterostrophus (anamorph: Bipolaris maydis = Helminthosporium maydis) |
| Southern leaf spot | Stenocarpella macrospora = Diplodia macrospora |
| Stalk rots, minor | Cercospora sorghi, Fusarium episphaeria, F. merismoides, F. oxysporum Schlechtend, F. poae, F. roseum, F. solani (teleomorph: Nectria haematococca), F. tricinctum, Mariannaea elegans, Mucor sp., Rhopographus zeae, Spicaria sp. |
| Storage rots | Aspergillus spp., Penicillium spp. and other fungi |
| Tar spot* | Phyllachora maydis |
| Trichoderma ear rot and root rot | Trichoderma viride = T. lignorum teleomorph: Hypocrea sp. |
| White ear rot, root and stalk rot | Stenocarpella maydis = Diplodia zeae |
| Yellow leaf blight | Ascochyta ischaemi, Phyllosticta maydis (teleomorph: Mycosphaerella zeae-maydis) |
| Zonate leaf spot | Gloeocercospora sorghi |

*Not known to occur naturally on corn in the United States.

Plant parasitic nematodes are a cause of disease in many plants, including maize. It is proposed that it would be possible to make the corn plant resistant to these organisms through the expression of novel genes. It is anticipated that control of nematode infestations would be accomplished by altering the ability of the nematode to recognize or attach to a host plant and/or enabling the plant to produce nematicidal compounds, including but not limited to proteins. Examples of nematode-associated plant diseases, for which one could introduce resistance to in a transgenic plant in accordance with the invention are given below, in Table 8.

TABLE 8

Parasitic Nematodes

| DISEASE | PATHOGEN |
| --- | --- |
| Awl | Dolichodorus spp., *D. heterocephalus* |
| Bulb and stem (Europe) | *Ditylenchus dipsaci* |
| Burrowing | *Radopholus similis* |
| Cyst | *Heterodera avenae, H. zeae, Punctodera chalcoensis* |
| Dagger | Xiphinema spp., *X. americanum, X. mediterraneum* |
| False root-knot | *Nacobbus dorsalis* |
| Lance, Columbia | *Hoplolaimus columbus* |
| Lance | Hoplolaimus spp., *H. galeatus* |
| Lesion | Pratylenchus spp., *P. brachyurus, P. crenatus, P. hexincisus, P. neglectus, P. penetrans, P. scribneri, P. thornei, P. zeae* |
| Needle | Longidorus spp., *L. breviannulatus* |
| Ring | Criconemella spp., *C. ornata* |
| Root-knot | Meloidogyne spp., *M. chitwoodi, M. incognita, M. javanica* |
| Spiral | Helicotylenchus spp. |
| Sting | Belonolaimus spp., *B. longicaudatus* |
| Stubby-root | Paratrichodorus spp., *P. christiei, P. minor, Quinisulcius acutus,* Trichodorus spp. |
| Stunt | *Tylenchorhynchus dubius* |

5. Mycotoxin Reduction/Elimination

Production of mycotoxins, including aflatoxin and furmonisin, by fungi associated with monocotyledonous plants such as maize is a significant factor in rendering the grain not useful. These fungal organisms do not cause disease symptoms and/or interfere with the growth of the plant, but they produce chemicals (mycotoxins) that are toxic to animals. It is contemplated that inhibition of the growth of these fungi would reduce the synthesis of these toxic substances and therefore reduce grain losses due to mycotoxin contamination. It also is proposed that it may be possible to introduce novel genes into monocotyledonous plants such as maize that would inhibit synthesis of the mycotoxin without interfering with fungal growth. Further, it is contemplated that expression of a novel gene which encodes an enzyme capable of rendering the mycotoxin nontoxic would be useful in order to achieve reduced mycotoxin contamination of grain. The result of any of the above mechanisms would be a reduced presence of mycotoxins on grain.

6. Grain Composition or Quality

Genes may be introduced into monocotyledonous plants, particularly commercially important cereals such as maize, to improve the grain for which the cereal is primarily grown. A wide range of novel transgenic plants produced in this manner may be envisioned depending on the particular end use of the grain.

The largest use of maize grain is for feed or food. Introduction of genes that alter the composition of the grain may greatly enhance the feed or food value. The primary components of maize grain are starch, protein, and oil. Each of these primary components of maize grain may be improved by altering its level or composition. Several examples may be mentioned for illustrative purposes, but in no way provide an exhaustive list of possibilities.

The protein of cereal grains including maize is suboptimal for feed and food purposes especially when fed to pigs, poultry, and humans. The protein is deficient in several amino acids that are essential in the diet of these species, requiring the addition of supplements to the grain. Limiting essential amino acids may include lysine, methionine, tryptophan, threonine, valine, arginine, and histidine. Some amino acids become limiting only after corn is supplemented with other inputs for feed formulations. For example, when corn is supplemented with soybean meal to meet lysine requirements methionine becomes limiting. The levels of these essential amino acids in seeds and grain may be elevated by mechanisms which include, but are not limited to, the introduction of genes to increase the biosynthesis of the amino acids, decrease the degradation of the amino acids, increase the storage of the amino acids in proteins, or increase transport of the amino acids to the seeds or grain.

One mechanism for increasing the biosynthesis of the amino acids is to introduce genes that deregulate the amino acid biosynthetic pathways such that the plant can no longer adequately control the levels that are produced. This may be done by deregulating or bypassing steps in the amino acid biosynthetic pathway which are normally regulated by levels of the amino acid end product of the pathway. Examples include the introduction of genes that encode deregulated versions of the enzymes aspartokinase or dihydrodipicolinic acid (DHDP)-synthase for increasing lysine and threonine production, and anthranilate synthase for increasing tryptophan production. Reduction of the catabolism of the amino acids may be accomplished by introduction of DNA sequences that reduce or eliminate the expression of genes encoding enzymes that catalyze steps in the catabolic pathways such as the enzyme lysine-ketoglutarate reductase. It is anticipated that it may be desirable to target expression of genes relating to amino acid biosynthesis to the endosperm or embryo of the seed. More preferably, the gene will be targeted to the embryo. It will also be preferable for genes encoding proteins involved in amino acid biosynthesis to target the protein to a plastid using a plastid transit peptide sequence.

The protein composition of the grain may be altered to improve the balance of amino acids in a variety of ways including elevating expression of native proteins, decreasing expression of those with poor composition, changing the composition of native proteins, or introducing genes encoding entirely new proteins possessing superior composition. Examples may include the introduction of DNA that decreases the expression of members of the zein family of storage proteins. This DNA may encode ribozymes or antisense sequences directed to impairing expression of zein proteins or expression of regulators of zein expression such as the opaque-2 gene product. It also is proposed that the protein composition of the grain may be modified through the phenomenon of co-suppression, i.e., inhibition of expression of an endogenous gene through the expression of an identical structural gene or gene fragment introduced through transformation (Goring et al., 1991). Additionally, the introduced DNA may encode enzymes which degrade zeins. The decreases in zein expression that are achieved may be accompanied by increases in proteins with more desirable amino acid composition or increases in other major seed constituents such as starch. Alternatively, a chimeric gene may be introduced that comprises a coding sequence for a native protein of adequate amino acid composition such as for one of the globulin proteins or 10 kD delta zein, 20 kD delta zein, or 27 kD gamma zein of maize and a promoter or other regulatory sequence designed to elevate expression of said protein. The coding sequence of said gene may include additional or replacement codons for essential amino acids. Further, a coding sequence obtained from another species, or, a partially or completely synthetic sequence encoding a completely unique peptide sequence designed to enhance the amino acid composition of the seed may be employed. It is anticipated that it may be preferable to target expression of these transgenes encoding proteins with superior composition to the endosperm of the seed.

The introduction of genes that alter the oil content of the grain may be of value. Increases in oil content may result in increases in metabolizable-energy-content and density of the seeds for use in feed and food. The introduced genes may encode enzymes that remove or reduce rate-limitations or regulated steps in fatty acid or lipid biosynthesis. Such genes may include, but are not limited to, those that encode acetyl-CoA carboxylase, ACP-acyltransferase, β-ketoacyl-ACP synthase, plus other well known fatty acid biosynthetic activities. Other possibilities are genes that encode proteins that do not possess enzymatic activity such as acyl carrier protein. Genes may be introduced that alter the balance of fatty acids present in the oil providing a more healthful or nutritive feedstuff. The introduced DNA also may encode sequences that block expression of enzymes involved in fatty acid biosynthesis, altering the proportions of fatty acids present in the grain such as described below. Some other examples of genes specifically contemplated by the inventors for use in creating transgenic plants with altered oil composition traits include 2-acetyltransferase, oleosin, pyruvate dehydrogenase complex, acetyl CoA synthetase, ATP citrate lyase, ADP-glucose pyrophosphorylase, and genes of the carnitine-CoA-acetyl-CoA shuttles. It is anticipated that expression of genes related to oil biosynthesis will be targeted to the plastid, using a plastid transit peptide sequence and preferably expressed in the seed embryo.

Genes may be introduced that enhance the nutritive value of the starch component of the grain, for example by increasing the degree of branching, resulting in improved utilization of the starch in cows by delaying its metabolism. It is anticipated that expression of genes related to starch biosynthesis will preferably be targeted to the endosperm of the seed.

Besides affecting the major constituents of the grain, genes may be introduced that affect a variety of other nutritive, processing, or other quality aspects of the grain as used for feed or food. For example, pigmentation of the grain may be increased or decreased. Enhancement and stability of yellow pigmentation is desirable in some animal feeds and may be achieved by introduction of genes that result in enhanced production of xanthophylls and carotenes by eliminating rate-limiting steps in their production. Such genes may encode altered forms of the enzymes phytoene synthase, phytoene desaturase, or lycopene synthase. Alternatively, unpigmented white corn is desirable for production of many food products and may be produced by the introduction of DNA which blocks or eliminates steps in pigment production pathways.

Most of the phosphorous content of the grain is in the form of phytate, a form of phosphate storage that is not metabolized by monogastric animals. Therefore, in order to increase the availability of seed phosphate, it is anticipated that one will desire to decrease the amount of phytate in seed and increase the amount of free phosphorous. Alternatively, one may express a gene in corn seed which will be activated, e.g., by pH, in the gastric system of a monogastric animal and will release phosphate from phytate, e.g., phytase.

Feed or food comprising primarily maize or other cereal grains possesses insufficient quantities of vitamins and must be supplemented to provide adequate nutritive value. Introduction of genes that enhance vitamin biosynthesis in seeds may be envisioned including, for example, vitamins A, E, $B_{12}$, choline, and the like. Maize grain also does not possess sufficient mineral content for optimal nutritive value. Genes that affect the accumulation or availability of compounds containing phosphorus, sulfur, calcium, manganese, zinc, and iron among others would be valuable. An example may be the introduction of a gene that reduced phytic acid production or encoded the enzyme phytase which enhances phytic acid breakdown. These genes would increase levels of available phosphate in the diet, reducing the need for supplementation with mineral phosphate.

Numerous other examples of improvement of maize or other cereals for feed and food purposes might be described. The improvements may not even necessarily involve the grain, but may, for example, improve the value of the corn for silage. Introduction of DNA to accomplish this might include sequences that alter lignin production such as those that result in the "brown midrib" phenotype associated with superior feed value for cattle.

In addition to direct improvements in feed or food value, genes also may be introduced which improve the processing of corn and improve the value of the products resulting from the processing. The primary method of processing corn is via wetmilling. Maize may be improved though the expression of novel genes that increase the efficiency and reduce the cost of processing such as by decreasing steeping time.

Improving the value of wetmilling products may include altering the quantity or quality of starch, oil, corn gluten meal, or the components of corn gluten feed. Elevation of starch may be achieved through the identification and elimination of rate limiting steps in starch biosynthesis or by decreasing levels of the other components of the grain resulting in proportional increases in starch. An example of the former may be the introduction of genes encoding ADP-glucose pyrophosphorylase enzymes with altered regulatory activity or which are expressed at higher level. Examples of the latter may include selective inhibitors of, for example, protein or oil biosynthesis expressed during later stages of kernel development.

The properties of starch may be beneficially altered by changing the ratio of amylose to amylopectin, the size of the starch molecules, or their branching pattern. Through these changes a broad range of properties may be modified which include, but are not limited to, changes in gelatinization temperature, heat of gelatinization, clarity of films and pastes, rheological properties, and the like. To accomplish these changes in properties, genes that encode granule-bound or soluble starch synthase activity or branching enzyme activity may be introduced alone or combination. DNA such as antisense constructs may also be used to decrease levels of endogenous activity of these enzymes. The introduced genes or constructs may possess regulatory sequences that time their expression to specific intervals in starch biosynthesis and starch granule development. Furthermore, it may be worthwhile to introduce and express genes that result in the in vivo derivatization, or other modification, of the glucose moieties of the starch molecule. The covalent attachment of any molecule may be envisioned, limited only by the existence of enzymes that catalyze the derivatizations and the accessibility of appropriate substrates in the starch granule. Examples of important derivations may include the addition of functional groups such as amines, carboxyls, or phosphate groups which provide sites for subsequent in vitro derivatizations or affect starch properties through the introduction of ionic charges. Examples of other modifications may include direct changes of the glucose units such as loss of hydroxyl groups or their oxidation to aldehyde or carboxyl groups.

Oil is another product of wetmilling of corn, the value of which may be improved by introduction and expression of genes. The quantity of oil that can be extracted by wetmilling may be elevated by approaches as described for feed and food above. Oil properties also may be altered to improve its performance in the production and use of cooking oil, shortenings, lubricants or other oil-derived products or improvement of its health attributes when used in the food-related applications. Novel fatty acids also may be synthesized which upon extraction can serve as starting materials for chemical syntheses. The changes in oil properties may be achieved by altering the type, level, or lipid arrangement of the fatty acids present in the oil. This in turn may be accomplished by the addition of genes that encode enzymes that catalyze the synthesis of novel fatty acids and the lipids possessing them or by increasing levels of native fatty acids while possibly reducing levels of precursors. Alternatively, DNA sequences may be introduced which slow or block steps in fatty acid biosynthesis resulting in the increase in precursor fatty acid intermediates. Genes that might be added include desaturases, epoxidases, hydratases, dehydratases, and other enzymes that catalyze reactions involving fatty acid intermediates. Representative examples of catalytic steps that might be blocked include the desaturations from stearic to oleic acid and oleic to linolenic acid resulting in the respective accumulations of stearic and oleic acids. Another example is the blockage of elongation steps resulting in the ccumulation of $C_8$ to $C_{12}$ saturated fatty acids.

Improvements in the other major corn wetmilling products, corn gluten meal and corn gluten feed, may also be achieved by the introduction of genes to obtain novel corn plants. Representative possibilities include but are not limited to those described above for improvement of food and feed value.

In addition, it may further be considered that the corn plant be used for the production or manufacturing of useful biological compounds that were either not produced at all, or not produced at the same level, in the corn plant previously. The novel corn plants producing these compounds are made possible by the introduction and expression of genes by corn transformation methods. The vast array of possibilities include but are not limited to any biological compound which is presently produced by any organism such as proteins, nucleic acids, primary and intermediary metabolites, carbohydrate polymers, etc. The compounds may be produced by the plant, extracted upon harvest and/or processing, and used for any presently recognized useful purpose such as pharmaceuticals, fragrances, and industrial enzymes to name a few.

Further possibilities to exemplify the range of grain traits or properties potentially encoded by introduced genes in transgenic plants include grain with less breakage susceptibility for export purposes or larger grit size when processed by dry milling through introduction of genes that enhance γ-zein synthesis, popcorn with improved popping quality and expansion volume through genes that increase pericarp thickness, corn with whiter grain for food uses though introduction of genes that effectively block expression of enzymes involved in pigment production pathways, and improved quality of alcoholic beverages or sweet corn through introduction of genes which affect flavor such as the shrunken 1 gene (encoding sucrose synthase) or the shrunken 2 gene (encoding ADPG pyrophosphorylase) for sweet corn.

7. Plant Agronomic Characteristics

Two of the factors determining where corn can be grown are the average daily temperature during the growing season and the length of time between frosts. Within the areas where it is possible to grow corn, there are varying limitations on the maximal time it is allowed to grow to maturity and be harvested. The corn to be grown in a particular area is selected for its ability to mature and dry down to harvestable moisture content within the required period of time with maximum possible yield. Therefore, corn of varying maturities is developed for different growing locations. Apart from the need to dry down sufficiently to permit harvest, it is desirable to have maximal drying take place in the field to minimize the amount of energy required for additional drying post-harvest. Also, the more readily the grain can dry down, the more time there is available for growth and kernel fill. It is considered that genes that influence maturity and/or dry down can be identified and introduced into corn lines using transformation techniques to create new corn varieties adapted to different growing locations or the same growing location, but having improved yield to moisture ratio at harvest. Expression of genes that are involved in regulation of plant development may be especially useful, e.g., the liguleless and rough sheath genes that have been identified in corn.

It is contemplated that genes may be introduced into monocots that would improve standability and other plant growth characteristics. Expression of novel genes which confer stronger stalks, improved root systems, or prevent or reduce ear droppage would be of great value to the farmer. It is proposed that introduction and expression of genes that increase the total amount of photoassimilate available by, for example, increasing light distribution and/or interception would be advantageous. In addition, the expression of genes that increase the efficiency of photosynthesis and/or the leaf canopy would further increase gains in productivity. It is contemplated that expression of a phytochrome gene in corn may be advantageous. Expression of such a gene may reduce apical dominance, confer semidwarfism on a plant, and increase shade tolerance (U.S. Pat. No. 5,268,526). Such approaches would allow for increased plant populations in the field.

Delay of late season vegetative senescence would increase the flow of assimilate into the grain and thus increase yield. It is proposed that overexpression of genes within corn that are associated with "stay green" or the expression of any gene that delays senescence would be advantageous. For example, a nonyellowing mutant has been identified in *Festuca pratensis* (Davies et al., 1990). Expression of this gene as well as others may prevent premature breakdown of chlorophyll and thus maintain canopy function.

8. Nutrient Utilization

The ability to utilize available nutrients may be a limiting factor in growth of monocotyledonous plants such as maize. It is proposed that it would be possible to alter nutrient uptake, tolerate pH extremes, mobilization through the plant, storage pools, and availability for metabolic activities by the introduction of novel genes. These modifications would allow a plant such as maize to more efficiently utilize available nutrients. It is contemplated that an increase in the activity of, for example, an enzyme that is normally present in the plant and involved in nutrient utilization would increase the availability of a nutrient. An example of such an enzyme would be phytase. It is further contemplated that enhanced nitrogen utilization by the corn plant is desirable. Expression of a glutamate dehydrogenase gene in maize, e.g., *E. coli* gdhA genes, may lead to increased fixation of nitrogen in organic compounds. Furthermore, expression of gdhA in corn may lead to enhanced resistance to the herbicide glufosinate by incorporation of excess ammonia into glutamate, thereby detoxifying the ammonia. It is also contemplated that expression of a novel gene may make a nutrient source available that was previously not accessible, e.g., an enzyme that releases a component of nutrient value from a more complex molecule, perhaps a macromolecule.

9. Male Sterility

Male sterility is useful in the production of hybrid seed. It is proposed that male sterility may be produced through expression of novel genes. For example, it has been shown that expression of genes that encode proteins that interfere with development of the male inflorescence and/or gametophyte result in male sterility. Chimeric ribonuclease genes that express in the anthers of transgenic tobacco and oilseed rape have been demonstrated to lead to male sterility (Mariani et al., 1990).

A number of mutations were discovered in maize that confer cytoplasmic male sterility. One mutation in particular, referred to as T cytoplasm, also correlates with sensitivity to Southern corn leaf blight. A DNA sequence, designated TURF-13 (Levings, 1990), was identified that correlates with T cytoplasm. It is proposed that it would be possible through the introduction of TURF-13 via transformation, to separate male sterility from disease sensitivity. As it is necessary to be able to restore male fertility for breeding purposes and for grain production, it is proposed that genes encoding restoration of male fertility may also be introduced.

10. Negative Selectable Markers

Introduction of genes encoding traits that can be selected against may be useful for eliminating undesirable linked genes. It is contemplated that when two or more genes are introduced together by cotransformation that the genes will be linked together on the host chromosome. For example, a gene encoding a *Bt* gene that confers insect resistance on the plant may be introduced into a plant together with a bar gene that is useful as a selectable marker and confers resistance to the herbicide Liberty® on the plant. However, it may not be desirable to have an insect resistant plant that is also resistant to the herbicide Liberty®. It is proposed that one could also introduce an antisense bar gene that is expressed in those tissues where one does not want expression of the bar gene, e.g., in whole plant parts. Hence, although the bar gene is expressed and is useful as a selectable marker, it is not useful to confer herbicide resistance on the whole plant. The bar antisense gene is a negative selectable marker.

It also is contemplated that negative selection is necessary in order to screen a population of transformants for rare homologous recombinants generated through gene targeting. For example, a homologous recombinant may be identified through the inactivation of a gene that was previously expressed in that cell. The antisense gene to neomycin phosphotransferase II (NPT II) has been investigated as a negative selectable marker in tobacco (*Nicotiana tabacum*) and *Arabidopsis thaliana* (Xiang. and Guerra, 1993). In this example, both sense and antisense NPT II genes are introduced into a plant through transformation and the resultant plants are sensitive to the antibiotic kanamycin. An introduced gene that integrates into the host cell chromosome at the site of the antisense NPT II gene, and inactivates the antisense gene, will make the plant resistant to kanamycin and other aminoglycoside antibiotics. Therefore, rare, site-specific recombinants may be identified by screening for antibiotic resistance. Similarly, any gene, native to the plant or introduced through transformation, that when inactivated confers resistance to a compound, may be useful as a negative selectable marker.

It is contemplated that negative selectable markers may also be useful in other ways. One application is to construct transgenic lines in which one could select for transposition to unlinked sites. In the process of tagging it is most common for the transposable element to move to a genetically linked site on the same chromosome. A selectable marker for recovery of rare plants in which transposition has occurred to an unlinked locus would be useful. For example, the enzyme cytosine deaminase may be useful for this purpose (Stouggard, 1993). In the presence of this enzyme the compound 5-fluorocytosine is converted to 5-fluorouracil which is toxic to plant and animal cells. If a transposable element is linked to the gene for the enzyme cytosine deaminase, one may select for transposition to unlinked sites by selecting for transposition events in which the resultant plant is now resistant to 5-fluorocytosine. The parental plants and plants containing transpositions to linked sites will remain sensitive to 5-fluorocytosine. Resistance to 5-fluorocytosine is due to loss of the cytosine deaminase gene through genetic segregation of the transposable element and the cytosine deaminase gene. Other genes that encode proteins that render the plant sensitive to a certain compound will also be useful in this context. For example, T-DNA gene 2 from *Agrobacterium tumefaciens* encodes a protein that catalyzes the conversion of α-naphthalene acetamide (NAM) to α-naphthalene acetic acid (NAA) renders plant cells sensitive to high concentrations of NAM (Depicker et al., 1988).

It also is contemplated that negative selectable markers may be useful in the construction of transposon tagging lines. For example, by marking an autonomous transposable element such as Ac, Master Mu, or En/Spn with a negative selectable marker, one could select for transformants in which the autonomous element is not stably integrated into the genome. It is proposed that this would be desirable, for example, when transient expression of the autonomous element is desired to activate in trans the transposition of a defective transposable element, such as Ds, but stable integration of the autonomous element is not desired. The presence of the autonomous element may not be desired in order to stabilize the defective element, i.e., prevent it from further transposing. However, it is proposed that if stable integration of an autonomous transposable element is desired in a plant the presence of a negative selectable marker may make it possible to eliminate the autonomous element during the breeding process.

(vi) Non-Protein-Expressing Sequences

1. RNA-Expressing

DNA may be introduced into corn and other monocots for the purpose of expressing RNA transcripts that function to affect plant phenotype yet are not translated into protein. Two examples are antisense RNA and RNA with ribozyme activity. Both may serve possible functions in reducing or eliminating expression of native or introduced plant genes.

Genes may be constructed or isolated, which when transcribed, produce antisense RNA that is complementary to all or part(s) of a targeted messenger RNA(s). The antisense RNA reduces production of the polypeptide product of the messenger RNA. The polypeptide product may be any protein encoded by the plant genome. The aforementioned genes will be referred to as antisense genes. An antisense gene may thus be introduced into a plant by transformation methods to produce a novel transgenic plant with reduced expression of a selected protein of interest. For example, the protein may be an enzyme that catalyzes a reaction in the plant. Reduction of the enzyme activity may reduce or eliminate products of the reaction which include any enzymatically synthesized compound in the plant such as fatty acids, amino acids, carbohydrates, nucleic acids and the like. Alternatively, the protein may be a storage protein, such as a zein, or a structural protein, the decreased expression of which may lead to changes in seed amino acid composition or plant morphological changes respectively. The possibilities cited above are provided only by way of example and do not represent the full range of applications.

Genes also may be constructed or isolated, which when transcribed produce RNA enzymes, or ribozymes, which can act as endoribonucleases and catalyze the cleavage of RNA molecules with selected sequences. The cleavage of selected messenger RNAs can result in the reduced production of their encoded polypeptide products. These genes may be used to prepare novel transgenic plants which possess them. The transgenic plants may possess reduced levels of polypeptides including, but not limited to, the polypeptides cited above that may be affected by antisense RNA.

It is also possible that genes may be introduced to produce novel transgenic plants which have reduced expression of a native gene product by a mechanism of co-suppression. It has been demonstrated in tobacco, tomato, and petunia (Goring et al., 1991; Smith et al., 1990; Napoli et al., 1990; van der Krol et al., 1990) that expression of the sense transcript of a native gene will reduce or eliminate expression of the native gene in a manner similar to, that observed for antisense genes. The introduced gene may encode all or part of the targeted native protein but its translation may not be required for reduction of levels of that native protein.

2. Non-RNA-Expressing

DNA elements including those of transposable elements such as Ds, Ac, or Mu, may be inserted into a gene to cause mutations. These DNA elements may be inserted in order to inactivate (or activate) a gene and thereby "tag" a particular trait. In this instance the transposable element does not cause instability of the tagged mutation, because the utility of the element does not depend on its ability to move in the genome. Once a desired trait is tagged, the introduced DNA sequence may be used to clone the corresponding gene, e.g., using the introduced DNA sequence as a PCR primer together with PCR gene cloning techniques (Shapiro, 1983; Dellaporta el al., 1988). Once identified, the entire gene(s) for the particular trait, including control or regulatory regions where desired, may be isolated, cloned and manipulated as desired. The utility of DNA elements introduced into an organism for purposes of gene tagging is independent of the DNA sequence and does not depend on any biological activity of the DNA sequence, i e., transcription into RNA or translation into protein. The sole function of the DNA element is to disrupt the DNA sequence of a gene.

It is contemplated that unexpressed DNA sequences, including novel synthetic sequences, could be introduced into cells as proprietary "labels" of those cells and plants and seeds thereof. It would not be necessary for a label DNA element to disrupt the function of a gene endogenous to the host organism, as the sole function of this DNA would be to identify the origin of the organism. For example, one could introduce a unique DNA sequence into a plant and this DNA element would identify all cells, plants, and progeny of these cells as having arisen from that labeled source. It is proposed that inclusion of label DNAs would enable one to distinguish proprietary germplasm or germplasm derived from such, from unlabelled germplasm.

Another possible element which may be introduced is a matrix attachment region element (MAR), such as the chicken lysozyme A element (Stief, 1989), which can be positioned around an expressible gene of interest to effect an increase in overall expression of the gene and diminish position dependent effects upon incorporation into the plant genome (Stief et al., 1989; Phi-Van et al., 1990).

IX. Site Specific Integration or Excision of Transgenes

It is specifically contemplated by the inventors that one could employ techniques for the site-specific integration or excision of transgenes prepared in accordance with the instant invention. An advantage of site-specific integration or excision is that it can be used to overcome problems associated with conventional transformation techniques, in which transgenes typically randomly integrate into a host genome and in multiple copies. This random insertion of introduced DNA into the genome of host cells can be lethal if the foreign DNA inserts into an essential gene. In addition, the expression of a transgene may be influenced by "position effects" caused by the surrounding genomic DNA. Further, because of difficulties associated with transformation of multiple transgene copies, including gene silencing, recombination and unpredictable inheritance, it is typically desirable to control the copy number of the inserted DNA, often only desiring the insertion of a single copy of the DNA sequence.

Site-specific integration or excision of transgenes or parts of transgenes can be achieved in plants by means of homologous recombination (see, for example, U.S. Pat. No. 5,527, 695, specifically incorporated herein by reference in its entirety). Homologous recombination is a reaction between any pair of DNA sequences having a similar sequence of nucleotides, where the two sequences interact (recombine) to form a new recombinant DNA species. The frequency of homologous recombination increases as the length of the shared nucleotide DNA sequences increases, and is higher with linearized plasmid molecules than with circularized plasmid molecules. Homologous recombination can occur between two DNA sequences that are less than identical, but the recombination frequency declines as the divergence between the two sequences increases.

Introduced DNA sequences can be targeted via homologous recombination by linking a DNA molecule of interest to sequences sharing homology with endogenous sequences of the host cell. Once the DNA enters the cell, the two homologous sequences can interact to insert the introduced DNA at the site where the homologous genomic DNA sequences were located. Therefore, the choice of homologous sequences contained on the introduced DNA, will determine the site where the introduced DNA is integrated via homologous recombination. For example, if the DNA sequence of interest is linked to DNA sequences sharing homology to a single copy gene of a host plant cell, the DNA sequence of interest will be inserted via homologous recombination at only that single specific site. However, if the DNA sequence of interest is linked to DNA sequences sharing homology to a multicopy gene of the host eukaryotic cell, then the DNA sequence of interest can be inserted via homologous recombination at each of the specific sites where a copy of the gene is located.

DNA can be inserted into the host genome by a homologous recombination reaction involving either a single reciprocal recombination (resulting in the insertion of the entire length of the introduced DNA) or through a double reciprocal recombination (resulting in the insertion of only the DNA located between the two recombination events). For example if one wishes to insert a foreign gene into the genomic site where a selected gene is located, the introduced DNA should contain sequences homologous to the selected gene. A single homologous recombination event would then result in the entire introduced DNA sequence being inserted into the selected gene. Alternatively, a double recombination event can be achieved by flanking each end of the DNA sequence of interest (the sequence intended to be inserted into the genome) with DNA sequences homologous to the selected gene. A homologous recombination event involving each of the homologous flanking regions will result in the insertion of the foreign DNA. Thus only those DNA sequences located between the two regions sharing genomic homology become integrated into the genome.

Although introduced sequences can be targeted for insertion into a specific genomic site via homologous recombination, in higher eukaryotes homologous recombination is a relatively rare event compared to random insertion events. In plant cells, foreign DNA molecules find homologous sequences in the cell's genome and recombine at a frequency of approximately $0.5-4.2 \times 10^{-4}$. Thus any transformed cell that contains an introduced DNA sequence integrated via homologous recombination will also likely contain numerous copies of randomly integrated introduced DNA sequences. Therefore, to maintain control over the copy number and the location of the inserted DNA, these randomly inserted DNA sequences can be removed. One manner of removing these random insertions is to utilize a site-specific recombinase system. In general, a site specific recombinase system consists of three elements: two pairs of DNA sequence (the site-specific recombination sequences) and a specific enzyme (the site-specific recombinase). The site-specific recombinase will catalyze a recombination reaction only between two site-specific recombination sequences.

A number of different site specific recombinase systems could be employed in accordance with the instant invention, including, but not limited to, the Cre/lox system of bacteriophage P1 (U.S. Pat. No. 5,658,772, specifically incorporated herein by reference in its entirety), the FLP/FRT system of yeast (Golic and Lindquist, 1989), the Gin recombinase of phage Mu (Maeser et al., 1991), the Pin recombinase of *E. coli* (Enomoto et al., 1983), and the R/RS system of the pSR1 plasmid (Araki et al., 1992). The bacteriophage P1 Cre/lox and the yeast FLP/FRT systems constitute two particularly useful systems for site specific integration or excision of transgenes. In these systems a recombinase (Cre or FLP) will interact specifically with its respective site-specific recombination sequence (lox or FRT respectively) to invert or excise the intervening sequences. The sequence for each of these two systems is relatively short (34 bp for lox and 47 bp for FRT) and therefore, convenient for use with transformation vectors.

The FLP/FRT recombinase system has been demonstrated to function efficiently in plant cells. Experiments on the performance of the FLP/FRT system in both maize and rice protoplasts indicate that FRT site structure, and amount of the FLP protein present, affects excision activity. In general, short incomplete FRT sites leads to higher accumulation of excision products than the complete full-length FRT sites. The systems can catalyze both intra- and intermolecular reactions in maize protoplasts, indicating its utility, for DNA excision as well as integration reactions. The recombination reaction is reversible and this reversibility can compromise the efficiency of the reaction in each direction. Altering the structure of the site-specific recombination sequences is one approach to remedying this situation. The site-specific recombination sequence can be mutated in a manner that the product of the recombination reaction is no longer recognized as a substrate for the reverse reaction, thereby stabilizing the integration or excision event.

In the Cre-lox system, discovered in bacteriophage P1, recombination between loxP sites occurs in the presence of the Cre recombinase (see, e.g., U.S. Pat. No. 5,658,772, specifically incorporated herein by reference in its entirety). This system has been utilized to excise a gene located between two lox sites which had been introduced into a yeast genome (Sauer, 1987). Cre was expressed from an inducible yeast GAL1 promoter and this Cre gene was located on an autonomously replicating yeast vector.

Since the lox site is an asymmetrical nucleotide sequence, lox sites on the same DNA molecule can have the same or opposite orientation with respect to each other. Recombination between lox sites in the same orientation results in a deletion of the DNA Segment located between the two lox sites and a connection between the resulting ends of the original DNA molecule. The deleted DNA segment forms a circular molecule of DNA. The original DNA molecule and the resulting circular molecule each contain a single lox site. Recombination between lox sites in opposite orientations on the same DNA molecule result in an inversion of the nucleotide sequence of the DNA segment located between the two lox sites. In addition, reciprocal exchange of DNA segments proximate to lox sites located on two different DNA molecules can occur. All of these recombination events are catalyzed by the product of the Cre coding region.

X. Purification of Proteins

It may, in particular embodiments of the current invention, be desirable to purify proteins encoded by transgenes of the current invention. Alternatively, native proteins may be isolated from a plant as part of an effort to clone a gene encoding the isolated protein, or the promoter directing expression of the gene. Once a protein is in hand, the protein can be sequenced and the coding sequence of the gene deduced. Probes or primers can be produced based on the deduced DNA sequence, thereby allowing efficient cloning of the corresponding gene.

Protein purification techniques are well known to those of skill in the art. These techniques involve, at one level, the crude fractionation of the cellular milieu to polypeptide and non-polypeptide fractions. Having separated the polypeptide from other proteins, the polypeptide of interest may be further purified using chromatographic and electrophoretic techniques to achieve partial or complete purification (or purification to homogeneity). Analytical methods particularly suited to the preparation of a pure peptide are ion-exchange chromatography, exclusion chromatography; polyacrylamide gel electrophoresis; and isoelectric focusing. A particularly efficient method of purifying peptides is fast protein liquid chromatography or even HPLC.

Various techniques suitable for use in protein purification will be well known to those of skill in the art. These include, for example, precipitation with ammonium sulphate, PEG, antibodies and the like or by heat denaturation, followed by centrifugation; chromatography steps such as ion exchange, gel filtration, reverse phase, hydroxylapatite and affinity chromatography; isoelectric focusing; gel electrophoresis; and combinations of such and other techniques. As is generally known in the art, it is believed that the order of conducting the various purification steps may be changed, or that certain steps may be omitted, and still result in a suitable method for the preparation of a substantially purified protein or peptide.

There is no general requirement that the protein or peptide always be provided in their most purified state. Indeed, it is contemplated that less substantially purified products will have utility in certain embodiments. Partial purification may be accomplished by using fewer purification steps in combination, or by utilizing different forms of the same general purification scheme. For example, it is appreciated that a cation-exchange column chromatography performed utilizing an HPLC apparatus will generally result in a greater "-fold" purification than the same technique utilizing a low pressure chromatography system. Methods exhibiting a lower degree of relative purification may have advantages in total recovery of protein product, or in maintaining the activity of an expressed protein.

It is known that the migration of a polypeptide can vary, sometimes significantly, with different conditions of SDS/PAGE (Capaldi et al., 1977). It will therefore be appreciated that under differing electrophoresis conditions, the apparent molecular weights of purified or partially purified expression products may vary.

High Performance Liquid Chromatography (HPLC) is characterized by a very rapid separation with extraordinary resolution of peaks. This is achieved by the use of very fine particles and high pressure to maintain an adequate flow rate. Separation can be accomplished in a matter of minutes, or at most an hour. Moreover, only a very small volume of the sample is needed because the particles are so small and close-packed that the void volume is a very small fraction of the bed volume. Also, the concentration of the sample need not be very great because the bands are so narrow that there is very little dilution of the sample.

Gel chromatography, or molecular sieve chromatography, is a special type of partition chromatography that is based on molecular size. The theory behind gel chromatography is that the column, which is prepared with tiny particles of an inert substance that contain small pores, separates larger molecules from smaller molecules as they pass through or around the pores, depending on their size. As long as the material of which the particles are made does not adsorb the molecules, the sole factor determining rate of flow is the size. Hence, molecules are eluted from the column in decreasing size, so long as the shape is relatively constant. Gel chromatography is unsurpassed for separating molecules of different size because separation is independent of all other factors such as pH, ionic strength, temperature, etc. There also is virtually no adsorption, less zone spreading and the elution volume is related in a simple matter to molecular weight.

Affinity Chromatography is a chromatographic procedure that relies on the specific affinity between a substance to be isolated and a molecule that it can specifically bind to. This is a receptor-ligand type interaction. The column material is synthesized by covalently coupling one of the binding partners to an insoluble matrix. The column material is then able to specifically adsorb the substance from the solution. Elution occurs by changing the conditions to those in which binding will not occur (alter pH, ionic strength, temperature, etc.).

A particular type of affinity chromatography useful in the purification of carbohydrate containing compounds is lectin affinity chromatography. Lectins are a class of substances that bind to a variety of polysaccharides and glycoproteins. Lectins are usually coupled to agarose by cyanogen bromide. Conconavalin A coupled to Sepharose was the first material of this sort to be used and has been widely used in the isolation of polysaccharides and glycoproteins other lectins that have been include lentil lectin, wheat germ agglutinin which has been useful in the purification of N-acetyl glucosaminyl residues and *Helix pomatia* lectin. Lectins themselves are purified using affinity chromatography with carbohydrate ligands. Lactose has been used to purify lectins from castor bean and peanuts; maltose has been useful in extracting lectins from lentils and jack bean; N-acetyl-D galactosamine is used for purifying lectins from soybean; N-acetyl glucosaminyl binds to lectins from wheat germ; D-galactosamine has been used in obtaining lectins from clams and L-fucose will bind to lectins from lotus.

The matrix should be a substance that itself does not adsorb molecules to any significant extent and that has a broad range of chemical, physical and thermal stability. The ligand should be coupled in such a way as to not affect its binding properties. The ligand should also provide relatively tight binding. And it should be possible to elute the substance without destroying the sample or the ligand. One of the most common forms of affinity chromatography is immunoaffinity chromatography. The generation of antibodies that would be. suitable for use in accord with the present invention is discussed below.

XI. Definitions

Exogenous gene: A gene which is not normally present in a given host genome in the exogenous gene's present form In this respect, the gene itself may be native to the host genome, however, the exogenous gene will comprise the native gene altered by the addition or deletion of one or more different regulatory elements. One type of exogenous gene contemplated by the inventor to be of particular utility in the current invention comprises a maize gene operably linked to a promoter from the genus Coix.

Expression: The combination of intracellular processes, including transcription and translation undergone by a coding DNA molecule such as a structural gene to produce a polypeptide.

Progeny: Any subsequent generation, including the seeds and plants therefrom, which is derived from a particular parental plant or set of parental plants.

Promoter: A recognition site on a DNA sequence or group of DNA sequences that provide an expression control element for a structural gene and to which RNA A polymerase specifically binds and initiates RNA synthesis (transcription) of that gene.

Regeneration: The process of growing a plant from a plant cell (e.g., plant protoplast or explant).

Selected DNA: A segment of DNA which has been introduced into a host genome. Preferred selected DNAs will include one or more exogenous genes and the elements for expressing an exogenous gene in a host cell, for example, a promoter and a terminator. Benefit may be realized by including one or more enhancer elements with the selected DNA.

Transformation: A process of introducing an exogenous DNA sequence or construct (e.g., a vector or expression cassette) into a cell or protoplast in which that exogenous DNA is incorporated into a chromosome or is capable of autonomous replication.

Transformed cell: A cell whose DNA has been altered by the introduction of an exogenous DNA molecule into that cell.

Transgene: A segment of DNA which is introduced into a host genome. Exemplary transgenes will provide the host cell, or plants regenerated therefrom, with a novel phenotype relative to the corresponding non-transformed cell or plant. Transgenes may encode proteins, RNA only or not be transcribed or translated. An individual plant may be provided with a transgene directly by transformation or by inheritance from or both of the parents of the plant.

Transgenic cell: Any cell derived or regenerated from a transformed cell. Exemplary transgenic cells include plant calli derived from a transformed plant cell and particular cells such as leaf, root, stem, e.g., somatic cells, or reproductive (germ) cells obtained from a transgenic plant.

Transgenic plant: A plant or progeny of any subsequent generation derived therefrom, of a transformed plant cell or protoplast, wherein the plant DNA contains an introduced exogenous DNA molecule not originally present in a native, non-transgenic plant of the same strain. The transgenic plant may additionally contain sequences which are native to the plant being transformed, but wherein the "exogenous" gene has been altered by gene technological means in order to alter the level or pattern of expression of the gene.

Transit Peptide: A polypeptide sequence which is capable of directing a polypeptide to a particular organelle or other location within a cell.

Vector: A DNA molecule capable of replication in a host cell and/or to which another DNA segment can be operatively linked so as to bring about replication of the attached segment. A plasmid is an exemplary vector or a DNA molecule used to carry new genes into cells. A plasmid is an exemplary vector which is an independent, stable, self-replicating piece of DNA.

XII. EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

Example 1

Cloning of Homeologous Sequences From Coix

Coix lacryma-jobi seeds (PI 320865) were obtained from the USDA/ARS Plant Introduction Station, Ames, Iowa. Seeds were germinated and allowed to grow in the greenhouse for several weeks. Genomic DNA was prepared from 2–3 week old leaf material according to the following protocol. Frozen leaf tissue (2 grams flesh weight) was ground into a fine powder with a glass rod under liquid nitrogen. Powdered tissue was mixed thoroughly with 8 ml of extraction buffer (100 mM Tris, pH 8.0; 50 mM EDTA; 1% v/v SDS; 500 mM NaCl), pre-warmed to 60° C., followed by a 45 minute incubation at 60° C. The sample was then mixed with 2.5 ml of ice-cold 5 M potassium acetate and then incubated on ice for 20 minutes. Protein aggregates were removed by centrifugation at 3750 rpm for 20 minutes and the supernatant was poured through a layer of Miracloth followed by precipitation of DNA by the mixing with 5 ml of isopropyl alcohol. Precipitated DNA was collected by centrifugation at 3750 rpm for 15 minutes. The supernatant was poured off from the pelleted DNA and the tube was inverted for 5 minutes to allow residual supernatant to drain from the pellet. DNA was resuspended in 300 $\mu$l of water containing 50 mM Tris, pH 8.0, 10 mM EDTA and 3 $\mu$l of RNase (10 mg/ml stock). The DNA was precipitated again by the mixing with 50 $\mu$L of 4.4 M ammonium acetate, pH 5.2, and 350 $\mu$L of isopropyl alcohol, followed by centrifugation in a microcentrifuge at 14,000 rpm for 10 minutes. The DNA pellet was washed with 750 $\mu$L of 80 % v/v ethanol and then allowed to drain by inversion for 10 minutes. The DNA was resuspended in 200 $\mu$L of water containing 10 mM Tris, pH 8.0, and 1 mM EDTA. Genomic DNA libraries were made, for use as PCR templates, with the Genome Walker PCR kit (Clontech, Palo Alto, Calif.) according to the manufacturer's instructions.

A DNA segment located 5' of the gamma-coixin protein coding sequence was then PCR-amplified as follows. A nested set of oligonucleotide primers were prepared designated, gCoix5' nest2 (SEQ ID NO:1) and gCoix5' nest3 (SEQ ID NO:2), which correspond to positions 267–288 and 26–53 respectively of the published gamma coixin sequence (Genbank Accession number X59850). Primers, designated AP1 (SEQ ID NO:3) and AP2 (SEQ ID NO:4), were also used and were provided in the "Genome Walker" kit from (Clontech). The sequence of the primers is as follows:

```
gCoix5' nest2 = CTGGAACTGGAACGGGCTTGGA
gCoix5' nest3 = GCGAGGGCAACGAGCAGCACCTTCATGG
         AP1 = GTAATACGACTCACTATAGGGC
         AP2 = ACTATAGGGCACGCGTGGT
```

PCR was performed as follows: First, the Long Template PCR System (Boehringer Mannheim (Indianapolis, Ind.) was used according to the manufacturers instructions with the following exceptions, each reaction contained: 350 $\mu$M dNTP's, 500 nM of each primer, 50 mM Tris-HCl, pH 9.2; 14 mM $(NH_4)_2SO_4$, 3.0 mM $MgCl_2$ and 2 $\mu$l (<25 ng) of template DNA from the Genome Walker library. The primers first used were gCoix5' nest2 and the adapter primer AP1. The following cycling conditions were carried out using an MJ Research PTC-100 thermocycler with a heated lid:

| | |
|---|---|
| 95° - 1 min. | 1 cycle |
| 94° - 30 sec. | |
| 72° - 3 min. | 7 cycles |
| 94° - 30 sec. | |
| 67° - 3 min. | 32 cycles |
| 67° - 4 min. | 1 cycle |
| 4° - hold | |

The products from this reaction were then diluted 1:25 with water and 2 $\mu$l was used as template for a second round of amplification. Primers were changed to the nested set of gCoix5' nest3 and adapter primer AP2. The only other changes were in the cycling itself, which was as follows:

| | |
|---|---|
| 95° - 1 min. | 1 cycle |
| 94° - 30 sec. | |
| 72° - 3 min. | 5 cycles |
| 94° - 30 sec. | |
| 67° - 3 min. | 20 cycles |
| 67° - 4 min. | 1 cycle |
| 4° - hold | |

Appropriate size bands (500 bp or larger) were isolated by gel electrophoresis and band excision and cloned into the plasmid vector pCR2.1, according to manufacturer's instructions (Invitrogen, Carlsbad, Calif.). DNA sequencing was performed using custom oligonucleotides or vector-localized primers and the ABI dye-deoxy sequencing kit (Perkin-Elmer, Applied Biosystems, Norwalk, Conn.) according to the manufacturer's instructions. Sequencing reactions were analyzed using an ABI Prism 373 DNA sequencer (Perkin-Elmer, Applied Biosystems). After obtaining the sequence of the 3' and 5' ends of the PCR product, primers were designed with convenient restriction enzyme site tails to allow for the amplification and subsequent cloning of the gamma coixin promoter directly from genomic DNA. The primers gcx-1000seq5'xho (SEQ ID NO:5), gcx-1pcr3'xba (SEQ ID NO:6) and gcx-1pcr3'nco (SEQ ID NO:7) were synthesized. The sequences of the primers were as follows:

```
gcx-1000seq5'xho = GGCTCGAGGGACCGGTTACAGCACACCACTG
gcx-1pcr3'xba   = GGTCTAGAGGTGTCGATCTTCTGTGCTCT
gcx-1pcr3'nco   = GGCCATGGGGTGTCGATCTTCTGTGCTCT
```

Amplification of the gamma coixin promoter was then carried out with the gcx-1pcr3'nco and gcx-1000seq5'xho primers using the High Fidelity PCR Kit (Boehringer Mannheim). The reaction mix contained 200 ng Coix genomic DNA template, 200 μM dNTPs, 500 nM of each primer, and 5 μl 10xbuffer #2. The cycling conditions, carried out with an MJ Research PTC-100 thermocycler with a heated lid, were as follows:

| | |
|---|---|
| 95° - 2 min. | 1 cycle |
| 94° - 1 min. | |
| 56° - 1 min. | |
| 72° - 1 min. | 32 cycles |
| 72° - 4 min. | |
| 4° - hold | |

Following amplification, the amplicon was digested with NcoI and XbaI for directional cloning into the GUS expression vector pDPG827 (mcs/GUS/nos in pSP72 backbone; Promega Corp., Madison, Wis.). The entire promoter insert, as well as the insertion junctions, were sequenced and the vector was designated pDPG844 (FIG. 1). DNA sequencing was then performed using custom oligonucleotides or vector-localized primers and the ABI dye-deoxy sequencing kit (Perkin-Elmer, Applied Biosystems, Norwalk, Conn.) according to the manufacturer's instructions. Sequencing reactions were analyzed using an ABI Prism 373 DNA sequencer (Perkin-Elmer, Applied Biosystems). The sequence of the promoter insert is given in SEQ ID NO:8.

Figure 2:
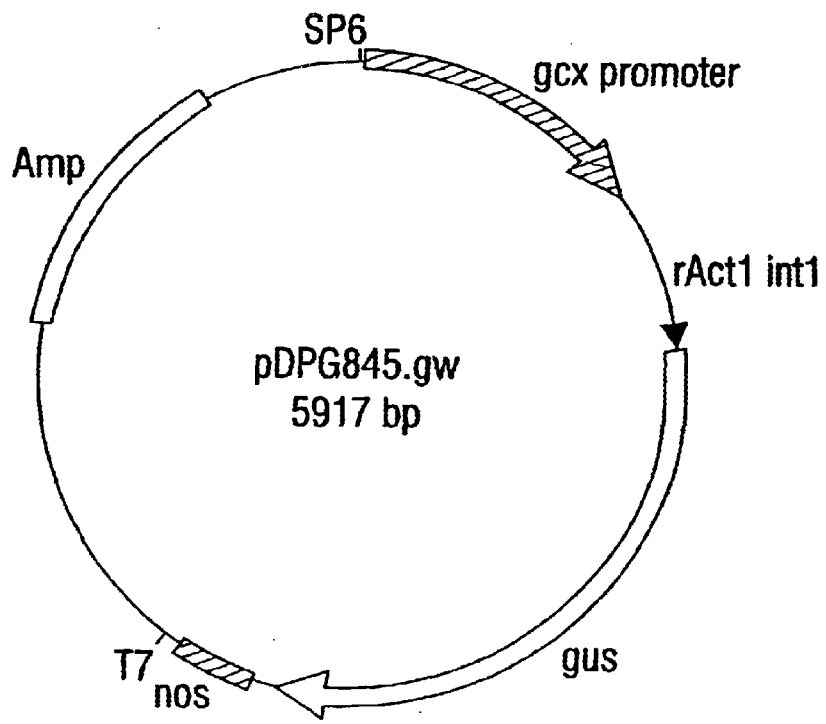
FIG. 2: Map of plasmid pDPG845. The construct contains an expression cassette comprised of an 894 bp promoter from the gamma coixin gene (SEQ ID NO:8), the rice actin1 intron1, the coding sequence of the GUS reporter gene and the nos terminator.

A parallel amplification of the gamma coixin promoter fragment was performed using the gcx-1pcr3'xba and gcx-1000seq5'xho primers. The amplification product was digested with XbaI and XhoI and ligated into the GUS expression vector pDPG828 (mcs/rice Actin intron1/GUS/nos in pSP72 backbone). Insertion junctions as well as entire insert were sequenced and the vector was designated pDPG 845 (FIG. 2).

Figure 3:
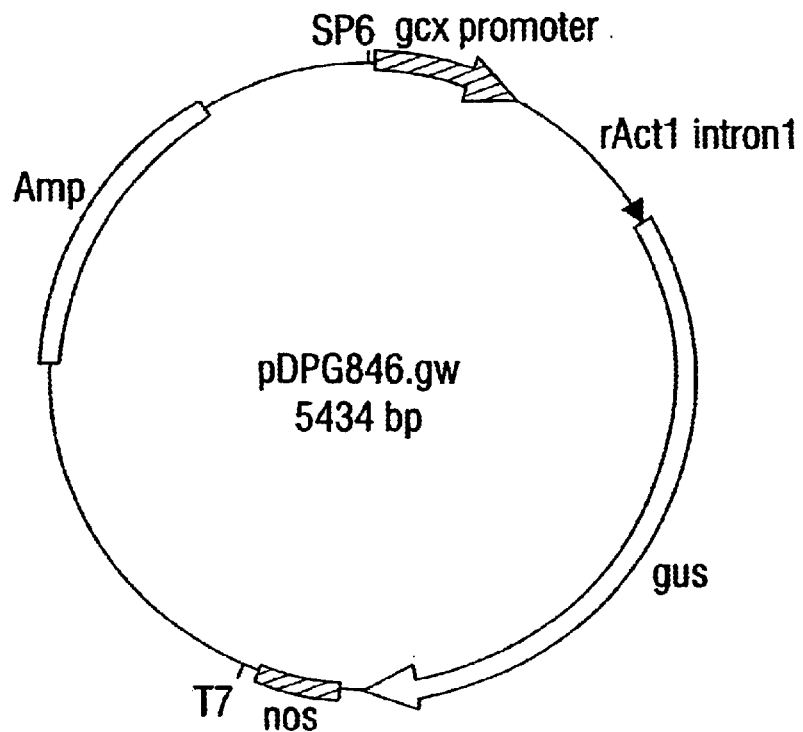
FIG. 3: Map of plasmid pDPG846. The plasmid contains an expression cassette comprised of a 412 bp promoter from the gamma coixin gene (SEQ ID NO:19), the rice actin1 intron1, the coding sequence of the GUS reporter gene, and the nos terminator.
Figure 4:
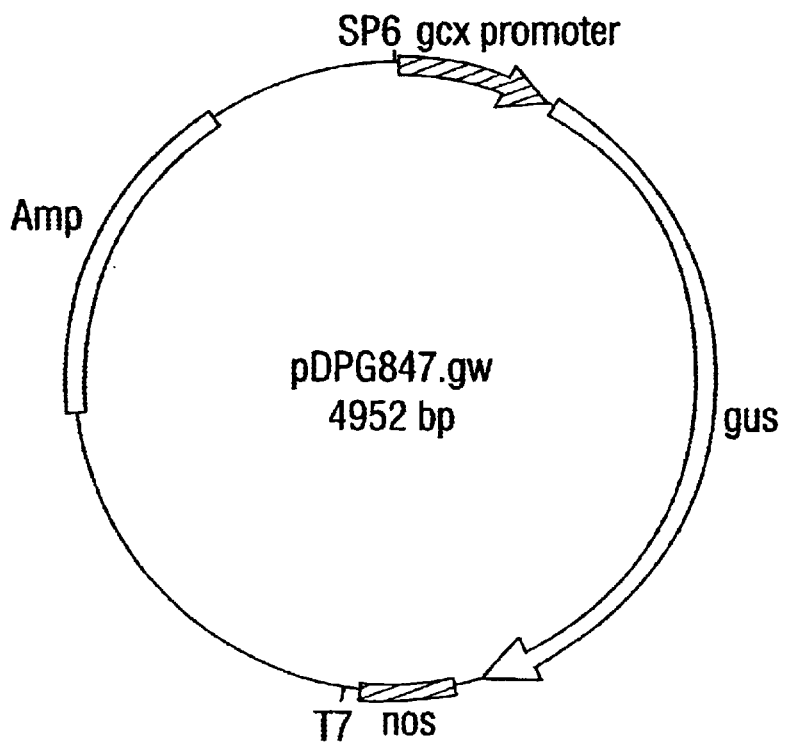
FIG. 4: Map of plasmid pDPG847. The plasmid contains an expression cassette comprised of a 412 bp promoter from the gamma coixin gene (SEQ ID NO:19), the coding sequence of the GUS reporter gene (GUS), and the nos terminator.

For construction of plasmids pDPG846 (FIG. 3) and pDPG847 (FIG. 4), amplification of the gamma coixin promoter was performed using the High Fidelity PCR Kit (Boehringer Mannheim) and the gcx-1pcr3'xba (SEQ ID NO:6) and gcx-(400)pcr5'xho (SEQ ID NO:24) primers. The amplification product was digested with XbaI and XbaI and ligated into the GUS expression vectors pDPG827 (mcs/GUS/nos in pSP72 backbone) and pDPG828 (mcs/rice Actin1 intron1/GUS/nos in pSP72 backbone to create vectors pDPG847 and pDPG846, respectively. Insertion junctions and the entire promoter insert were sequenced to confirm proper construction of the vectors. The sequence of the promoter insert is given in SEQ ID NO:19.

Figure 5:
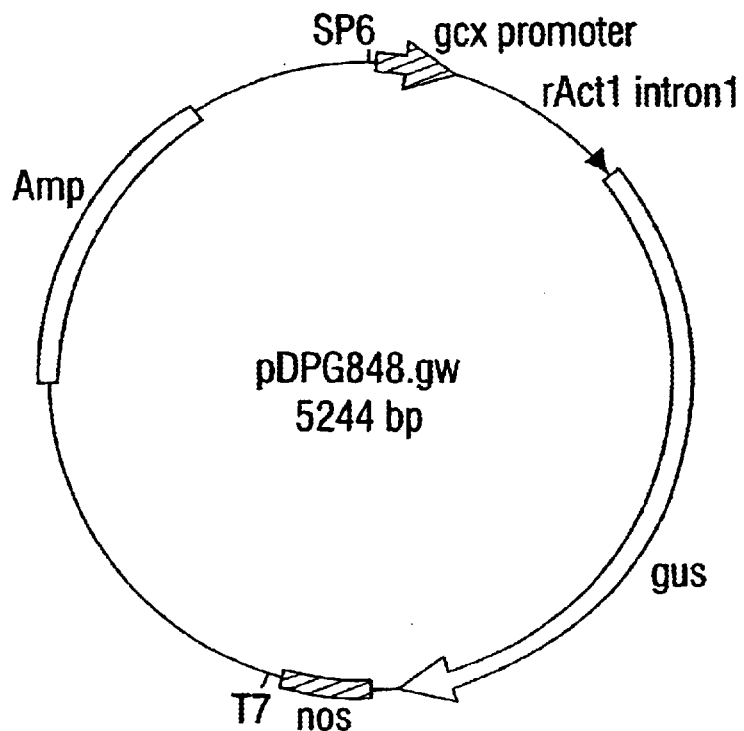
FIG. 5: Map of plasmid pDPG848. The plasmid contains an expression cassette comprised of a 222 bp promoter from the gamma coixin gene (SEQ ID NO:18), the rice actin1 intron, the GUS reporter gene; and the nos terminator.
Figure 6:
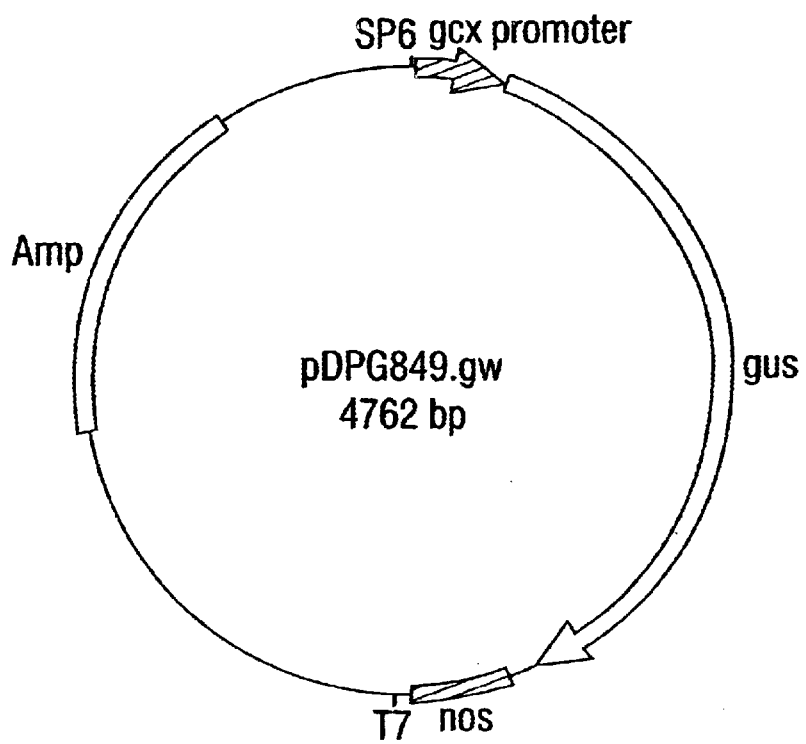
FIG. 6: Map of plasmid pDPG849. The plasmid contains an expression cassette comprised of a 222 bp promoter from the gamma coixin gene (SEQ ID NO:18); the coding sequence of a reporter gene (GUS), and the nos terminator.

Plasmids pDPG848 (FIG. 5) and pDPG849 (FIG. 6) were constructed in parallel to the construction of pDPG846 and pDPG847. The gamma coixin promoter fragment was PCR amplified using the High Fidelity PCR Kit (Boehringer Mannheim) and the primers gcx-1pcr3'xba (SEQ ID NO:6) and gcx-(220)pcr5'xho (SEQ ID NO:25). The amplification product was digested with XbaI and XhoI and ligated into the GUS expression vectors pDPG827 (mcs/GUS/nos in pSP72 backbone) and pDPG828 (mcs/rice Actin1 intron1/GUS/nos in pSP72 backbone to create vectors pDPG849 and pDPG848, respectively. Insertion junctions and the entire promoter insert were sequenced to confirm proper construction of the vectors. The sequence of the promoter insert is given in SEQ ID NO:18. The gcx-(400)pcr5'xho and gcx-(220)pcr5'xho sequences are as given below and in SEQ ID NO:24 and SEQ ID NO:25.

gcx-(400)pcr5'xho GGCTCGAGTAAGTATGCAGGA gcx-(220)pcr5'xho GGCTCGAGCACTCGGCTTGCT

Example 2

Isolation of the Gamma Coixin Terminator and Coding Sequence and Construction of pDPG869

The Genome Walker kit and genomic DNA libraries used to isolate the gamma coixin promoter were additionally used for the isolation of gamma coixin terminator sequences. All PCR concentrations and cycling conditions remained identical to those used for promoter isolation, (Example 1) for all rounds. The only changes were in the coixin-specific primers used. The first round of PCR was done using the primers gcx5'pcr2 (SEQ ID NO:9) and AP1, and the second round with the primers gCoix3'nest2 (SEQ ID NO:10) and AP2. The sequence of the primers were as follows:

```
gcx5'pcr2    = (CTCAGCCCCAGCAGCCACATCCA)
gCoix3'nest2 = (GTGCGGCAGCCAATGACAAGTC)
```

Figure 11:
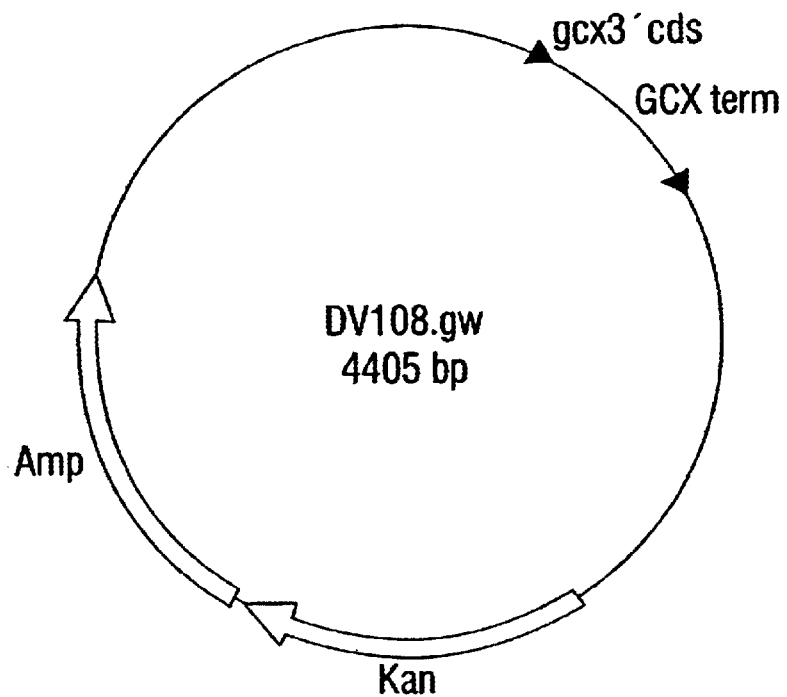
FIG. 11: Map of plasmid pDPG108. The construct contains the gamma coixin terminator (SEQ ID NO:11).

The amplification product was separated by gel electrophoresis, followed by excision of an appropriate sized band, elution of the band and cloning of the DNA into the vector pCR2.1 (Invitrogen, Carlsbad, Calif.), according to manufacturer's instructions and sequenced. This clone, containing the gamma coixin terminator, was designated DV108 (FIG. 11). The sequence of the terminator is given in SEQ ID NO:11.

To obtain the gamma coixin protein coding sequence, PCR amplification was used for the isolation of an amplification product which contained both the coding sequence and the promoter of the gamma coixin gene. Amplification was carried out using the primers gcx-1000seq5'xho (SEQ ID NO:12) and gCoix3'pcr (SEQ ID NO:13), given below.

gcx-1000seq5'xho = GGCTCGAGGGACCGGTTACAGCACACCACTG
gCoix3'pcr = TCAGTACTGGGCACCGCCGGC The "Master Amp" kit (Epicentre Technologies, Madison, Wis.) was used to optimize the amplification. The sequence of the promoter/coding amplification product was obtained using buffer D and the following program on a Robocycler (Stratagene):

| | |
|---|---|
| 94° - 2 min. | 1 cycle |
| 94° - 1 min. | |
| 73° - 1 min. | |
| 72° - 1 min. | 32 cycles |
| 72° - 4 min. | 1 cycle |
| 6° - hold | |

This amplicon was then cloned into pCR2.1. Using this plasmid construct as a template, the next PCR strategy was designed to obtain the coding sequence and the promoter as separate is reaction products. The following primers, gCoix 5'pcr+4 (SEQ ID NO:14) and gCoix 3'pcr+sac (SEQ ID NO:15), were designed for the amplification of the coding sequence alone:

gCoix 5'pcr + 4 = AAGGTGCTGCTCGTTGCCCTC
gCoix 3'pcr + sac = GGGAGCTCTCAGTACTGGGCACCGCCGGC These primers correspond to bases 31–51 and 607–627 respectively of the above indicated Genbank sequence. Use of the primer gCoix 5'pcr+4 results in an amplification product which lacks the start codon for the gamma coixin protein. The High Fidelity PCR kit from Boehringer Mannheim was used with a reaction mix of 100 pg plasmid template, 500 nM each primer 1×Buffer 1 and 200 µM dNTP in a 3 mM final concentration of $MgCl_2$. The cycling conditions, using an MJ Research PTC-100 thermocycler with a heated lid, were as follows:

| | |
|---|---|
| 95° - 2 min. | 1 cycle |
| 94° - 1 min. | |
| 62° - 1 min. | |
| 72° - 1 min. | 32 cycles |
| 72° - 4 min. | 1 cycle |
| 4° - hold | |

Figure 9:
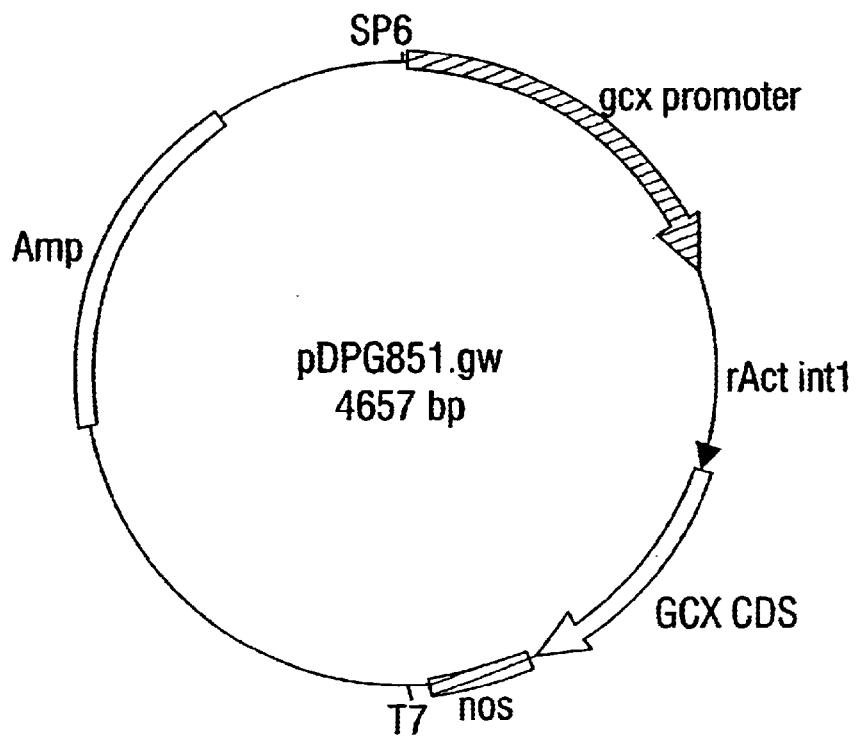
FIG. 9: Map of plasmid pDPG851. The construct contains an expression cassette comprised of: 894 bp promoter from the gamma coixin gene (SEQ ID NO:8), the rice actin1 intron1, the coding sequence of the gamma coixin gene (SEQ ID NO:16), and the nos terminator.

This reaction product was then purified by gel electrophoresis and band excision and digested with SacI for cloning into pDPG845. The plasmid pDPG845 was prepared by digesting with NcoI and a subsequent filling of the 5' overhang with Klenow by the addition of 2 units of Klenow enzyme and dNTPs to a final concentration of 0.2 mM each. This allowed for direct ligation of the ATG start codon to the 5' end of the gamma coixin protein coding sequence, thus restoring the complete open reading frame of gamma coixin. The vector was then digested with SacI and the GUS coding sequence removed to leave a compatible site for the 3' end of the gamma coixin coding sequence. The prepared pDPG845 vector and gamma coixin coding sequence were then ligated together to form the new vector designated pDPG851 (FIG. 9).

Figure 10:
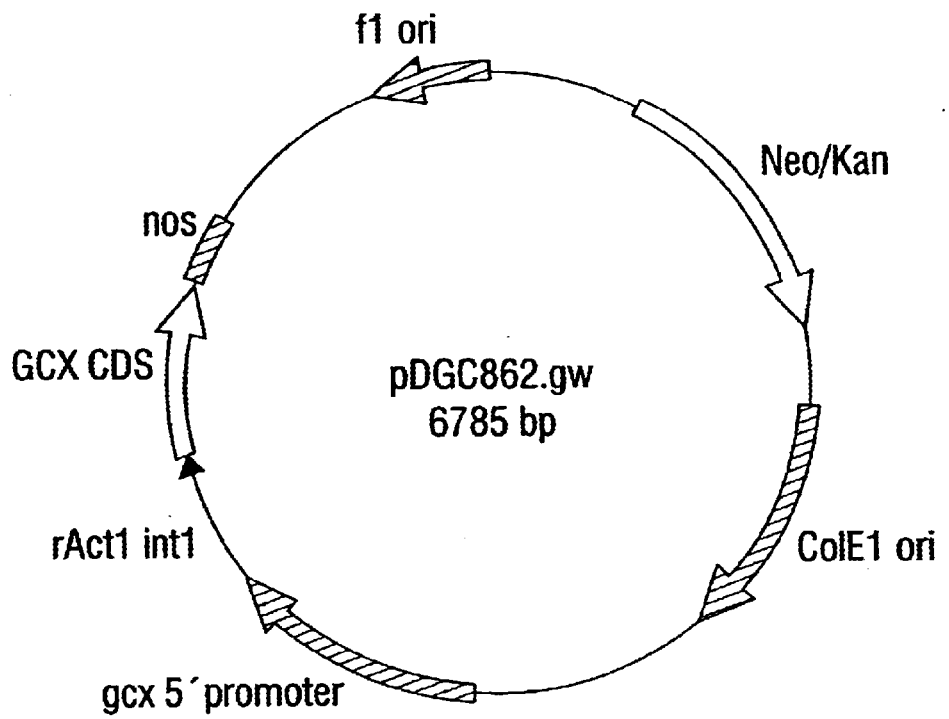
FIG. 10: Map of plasmid pDPG862. The construct contains an expression cassette comprised of a 894 bp sequence promoter from the gamma coixin gene (SEQ ID NO:8), the rice actin1 intron1, the coding sequence of the gamma coixin gene (SEQ ID NO:16), and the nos terminator.

To facilitate the replacement of the nos terminator in pDPG851 with the gamma coixin terminator, the expression cassette was moved to a more suitable vector, e.g., pBK-CMV (Stratagene, La Jolla, Calif.). This was done by digesting pBK-CMV with ScaI (blunt) and pDPG851 with XbaI and ClaI with a subsequent Klenow fill-in of the 5' overhangs (2 units Klenow and 0.2 mM of each dNTP). The pDPG851 cassette and the backbone of pBK-CMV were gel purified. The two plasmids were then ligated to generate pDPG862 (FIG. 10).

Figure 7:
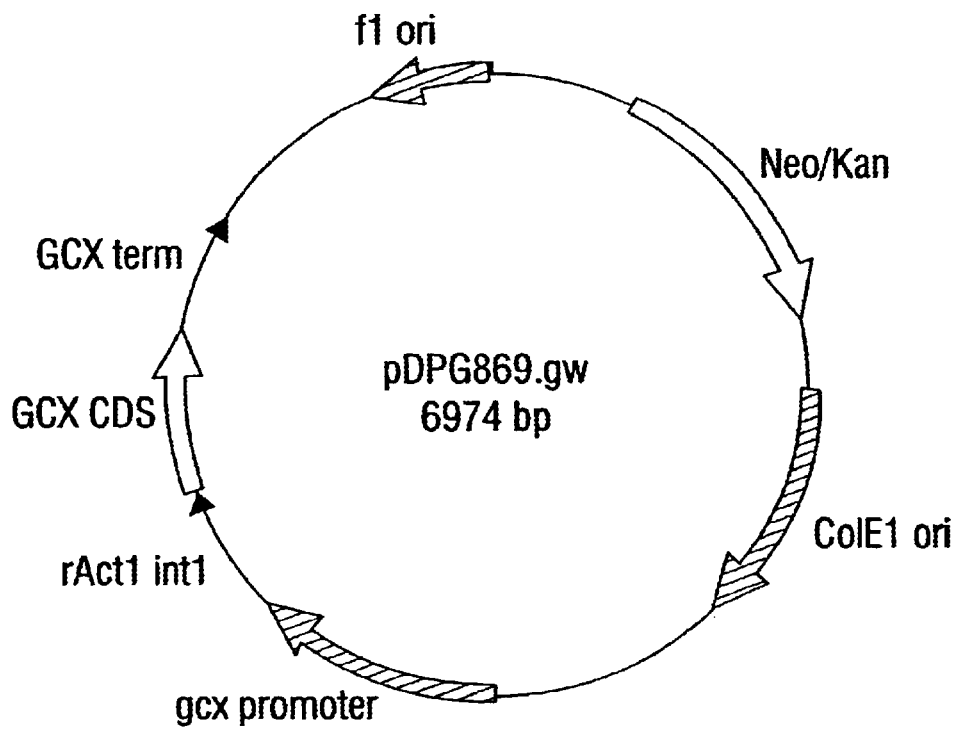
FIG. 7: Map of plasmid pDPG869. The construct contains an expression cassette comprised of a 894 bp promoter from the gamma coixin gene (SEQ ID NO:8), the rice actin1 intron1, the coding sequence of the gamma coixin gene (SEQ ID NO:16), and the gamma coixin terminator (SEQ ID NO:11).

The gamma coixin terminator was cloned into the 3' end of the gamma-coixin coding sequence in pDPG862. This was carried out by first removing the nos terminator and then cloning the purified coixin terminator in its place by performing the steps as indicated below the gamma coixin coding sequence possesses a ScaI site at position 620–625 of the reported Genbank sequence. This restriction site, which is present in pDPG862 and DV108 as a results of the portion of the coding sequence obtained by the Genome Walker procedure, was cut with ScaI, as well as NotI. The gamma coixin terminator sequence was then gel purified as was the backbone of pDPG862. These two fragments were ligated to generate pDPG869 (FIG. 7). The sequence of the gamma coixin coding sequence is given in SEQ ID NO:16. Each of these gene constructs were introduced by particle bombardment into regenerable cells of maize as described in Examples 5 and 6 below.

Example 3

Isolation of the Coix Oleosin 3 Terminator

The Genome Walker kit and genomic DNA libraries used to isolate the promoter and terminator sequences in Examples 1 and 2 were also used for the isolation of the Coix oleosin 3 terminator. All PCR concentrations and cycling conditions remained identical to those used in those examples, for all rounds of PCR. The only changes were in the Coix specific primers that were used. The first round of PCR was done using the primers cx-L3 3'nest1 (SEQ ID NO:26) and AP1 (SEQ ID NO:3), and the second round with the primers cx-L3 3'nest2 (SEQ ID NO:27), cx-L3 3'nest3 (SEQ ID NO:28) and AP2 (SEQ ID NO:4). The sequences of the primers were as follows:

cx-L3 3'nest1 CGGGCTGATCCTGGCCGGCACCGT
cx-L3 3'nest2 GTGTTCTCCTGGATGTACAAGTAC
cx-L3 3'nest3 TCCAAGGCCCGCGACGTCAAGGA The amplification products were separated by gel electrophoresis, followed by excision of an appropriate sized band (>500 bp), elution of the band and cloning of the DNA into the vector pCR2.1 (Invitrogen) was carried out according to manufacturer's instructions and the cloned DNA was sequenced as described above. This clone, containing the Coix oleosin terminator, was designated DV 112. The sequence of the oleosin termninator is given in SEQ ID NO:17.

Example 4

Sequence Comparison of the Gamma Coixin Promoter and Homeologous Promoters From Maize and Sorghum Gamma-prolamins are a class of seed storage proteins present in the endosperm of Coix, sorghum and maize. An analysis was carried out to determine the sequence similarity between the gamma prolamine promoter of Coix (gamma coixin, SEQ ID NO:8), cloned by the inventors as described in Example 1, and the gamma prolamine promoter regions of corresponding sequences from sorghum (gamma kafirin, SEQ ID NO:22, Genbank Accession No. X62480), and maize (gamma zein, SEQ ID NO:23, Genbank Accession No. X56117). Alignments were made 894 nucleotides upstream of the translation initiation codon using the Gene-Works DNA analysis software (Intelligenetics, Inc., Mountainview, Calif.). Gaps were introduced to facilitate alignment. The 3'-most end of each sequence corresponds to the ATG initiation codon. The results of the comparison are given in FIG. 8 and Table 9. The analysis indicates a 65% sequence identity between gamma coixin and gamma kafirin and a 63% sequence identity between gamma coixin and gamma zein. These results indicated significant differences between the promoter regions in each of the three species.

TABLE 9

Nucleotide sequence identity among gamma prolamin upstream regions in Coix, maize and sorghum.

|  | gamma kafirin −1 to −894 | gamma zein −1 to −894 |
|---|---|---|
| gamma coixin −1 to −894 | 65% | 63% |
| gamma zein −1 to −894 | 56% |  |

Example 5

Preparation of Microprojectiles

Microprojectiles were prepared as follows: gold particles were prepared by adding 60 mg of 0.6 μm gold particles (BioRad, cat. no. 165–2262) to 1000 μl absolute ethanol and incubating for at least 3 hours at room temperature followed by storage at −20° C. Twenty to thirty five μl of the sterile gold particles and more preferably 30 to 35 μl of gold particles (30 μl contains 1.8 mg of particles) were centrifuged in a microcentrifuge for up to 1 min. The supernatant was removed and one ml sterile water was added to the tube, followed by centrifugation at 1800–2000 rpm for 2–5 minutes. Microprojectile particles were resuspended in 25–30 μl of DNA solution containing about 250 ng of vector DNA.

Two hundred twenty microliters sterile water, 250 μl 2.5 M $CaCl_2$ and 50 μl stock spermidine (14 μl spermidine in 986 μl water) were then added to the particle containing solution. The solution was then thoroughly mixed and placed on ice, followed by vortexing at 4° C. for 10 minutes and centrifugation at 500 rpm for 5 minutes. The supernatant was removed and the pellet resuspended in 600 μl absolute ethanol. Following centrifugation at 500 rpm for 5 minutes, the pellet was resuspended in 36–38 μl of absolute ethanol, vortexed for approximately 20 seconds, and sonicated for 20–30 seconds. At this stage the particles were typically allowed to sit for 2–5 minutes, after which 5–10 μl of the supernatant was removed and dispensed on the surface of a flyer disk and the ethanol was allowed to dry completely. Alternatively, particles may be removed directly after resuspension and vortexing 20 to 30 seconds in 36 μl–38 μl of ethanol, placed on the flyer disk and allowed to dry as done for the settled treatment. The bombardment chamber was then evacuated to approximately 28 in. Hg prior to bombardment. The particles were then used for bombardment by a helium blast of approximately 1100 psi using the DuPont Biolistics PDS1000He particle bombardment device.

Example 6

Bombardment of Hi-II Immature Embryos

Immature embryos (1.2–3.0 mm in length) of the corn genotype Hi-II were excised from surface-sterilized, greenhouse-grown ears of Hi-II 10–12 days post-pollination. The Hi-II genotype was developed from an A188×B73 cross (Armstrong et al., 1991). Approximately 30 embryos per petri dish were plated axis side down on a modified N6 medium containing 1 mg/l 2,4-D, 100 mg/l casein hydrolysate, 6 mM L-proline, 0.5 g/l 2-(N-morpholino) ethanesulfonic acid (MES), 0.75 g/l $MgCl_2$, and 2% sucrose solidified with 2 g/l Gelgro, pH 5.8 (#735 medium). Embryos were cultured in the dark for two to four days at 24° C.

Approximately 3–4 hours prior to bombardment, embryos were transferred to the above culture medium with the sucrose concentration increased from 3% to 12%. When embryos were transferred to the high osmoticum medium they were arranged in concentric circles on the plate, starting 1 cm from the center of the dish, positioned such that their coleorhizal end was orientated toward the center of the dish. Usually two concentric circles were formed with 25–35 embryos per plate.

The plates containing embryos were placed on the third shelf from the bottom, 5 cm below the stopping screen. The 1100 psi rupture discs were used for bombardment. Each plate of embryos was bombarded once with the DuPont Biolistics PDS1000He particle gun. Following bombardment, embryos were allowed to recover on high osmoticum medium (735, 12% sucrose) overnight (16–24 hours) and were then transferred to selection medium containing 1 mg/l bialaphos (#739, 735 plus 1 mg/l bialaphos or #750, 735 plus 0.2M mannitol and 1 mg/l bialaphos). Embryos were maintained in the dark at 24° C. After three to four weeks on the initial selection plates about 90% of the embryos typically formed Type II callus and were transferred to selective medium containing 3 mg/l bialaphos (#758). Southern analysis can then be used for analysis of transformants and assays of gene expression may be carried out. The constructs used for transformation and number of transformants were as given below, in Table 10

TABLE 10

Transformants obtained from bombardment of maize embryos with constructs containing Coix DNA sequences.

| Plasmid Description | pDPG | Number of independent transformants | Number of plants derived from transformants |
|---|---|---|---|
| GcxPro(9OO)lrActinllgcoixinlNOS | 862 | 81 | 327 |
| GcxPro(900)/GUS/NOS | 844 | 17 | 65 |
| GcxPro(9OO)lrActinllGUSINOS | 845 | 14 | 60 |
| GcxPro(400)/GUS/NOS | 847 | 9 | 34 |

TABLE 10-continued

Transformants obtained from bombardment of maize embryos with constructs containing Coix DNA sequences.

| Plasmid Description | pDPG | Number of independent transformants | Number of plants derived from transformants |
|---|---|---|---|
| GcxPro(4OO)lrActinllGUSlNOS | 846 | 15 | 60 |
| GcxPro(220)/GUS/NOS | 849 | 11 | 37 |
| GcxPro(220)lrActinllGUSlNOS | 848 | 11 | 38 |

Example 7

Determination of Putative Promoter Regulatory Elements

Identification of putative regulatory elements within each promoter sequence is initiated by comparison with promoter sequences known to be expressed in similar tissue-specific or developmentally unique manner. Sequences which are shared among promoters with similar expression patterns are likely candidates for the binding of transcription factors and are thus likely elements which confer expression patterns. Confirmation of these putative regulatory elements is achieved by deletion analysis of each promoter followed by functional analysis of each deletion construct by assay of a reporter gene which is functionally attached to each construct.

Such an analysis was carried out on the cloned gamma coixin promoter. DNA sequence alignment of the Coix gamma coixin promoter with the promoters of the maize gamma zein and sorghum gamma kafirin genes, carried out as described in Example 4, revealed several short regions of homology which represent potential transcription factor binding sites. Several of these sites have also been previously identified as putative regulatory regions of sorghum storage protein promoters (Ottoboni et al., 1993; de Freitas et al., 1994). Four putative regulatory regions were identified. Two regions are predicted to confer general promoter activity, potentially in response to nitrogen status, and these regions are referred to as GCN4-like regions. Two additional regions are predicted to confer tissue-specific expression and are referred to as prolamin-box binding regions. The elements are arranged between 180 and 700 base pairs from the translation start site, with a GCN4 box being most proximal to the initiating methionine codon (−190 bp), followed by a prolamin box (−395 bp), a second GCN4 box (−525 bp) and finally, a second prolamin box (−650 bp).

Truncated promoter sequences were designed to specifically remove the putative tissue-specific regulatory elements by generating promoter fragments of 412 (SEQ ID NO:19) and 222 bp (SEQ ID NO:18) (distances from the translation start site). The 412 bp promoter fragment includes only the proximal GCN4 and prolamin-box motifs, while the 222 bp fragment includes only the proximal GCN4 motif, with both of the prolamin-box regions removed. These promoter fragments, in addition to the full-length gamma coixin promoter, were cloned into vectors containing the GUS reporter gene, with and without the rice actin 1 intron 1 to enhance expression. These vectors have been designated pDPG844, 845, 846, 847, 848 and 849, and their construction has been described above. Each construct was bombarded into immature maize embryos (as described in Example 6) and plants were generated which contain each of the promoter: GUS constructs as transgenes.

Plants containing these transgenes will be analyzed for expression of the GUS reporter gene in all plant tissues at many different developmental stages. It is predicted that the shortest of the promoter constructs (221 bp, pDPG848 and pDPG849) will not exhibit tissue-specific expression patterns, since this promoter is lacking the prolamin-box regulatory regions. It is further predicted that the 412 bp promoter constructs pDPG846 and pDPG847) will retain tissue-specificity, but will drive lower levels of expression when compared to the full-length promoter constructs (pDPG844 and pDPG845).

Examples 8

Sense Suppression of an α-Zein Gene in Transgenic Maize and Elimination of Suppression by Use of Coix Promoters The expression of a sense zein expression cassette in maize has been shown to induce suppression of endogenous zein expression if the zein gene is controlled by a maize promoter. In order to demonstrate that no suppression would result if a Coix promoter is used, transformation studies may be carried out and comparisons made between constructs expressed by maize or Coix promoters. Such studies are carried out as follows.

Maize cells were transformed with the plasmid vector pDPG531, which comprises a maize Z27 promoter operably linked to a maize Z4 sense coding sequence and the nopaline synthase 3' region, as is described in U.S. Pat. Ser. No. 08/763,704, filed Dec. 9, 1996, the disclosure of which is specifically incorporated herein by reference in its entirety. pDPG531 was made by cutting a fragment of approximately 960 base pairs from the vector SPZ4Ent and filling in the ends (U.S. Pat. Ser. No. 08/763,704, filed Dec. 9, 1996). Essentially the entire Z4 transcription unit is contained in SPZ4Ent, with a total insert size of 960 nucleotides. The Z4 gene was reconstructed from two Z4 subclones, pSPZ4R3' and pSPZ45'. The parent vector was pSPZ4R3', containing 713 nucleotides of a mid-repeat 3' nucleotide sequence, from nucleotide 630 to nucleotide 1341 of the Z4 sequence. The 5' end of the Z4 sequence was released by digestion with SacI (which cleaves the polylinker sequence outside the inserted gene) and BamHI, and the insert containing the 5' sequence from pSPZ45', obtained by SacI (which also cleaves the polylinker sequence) and BamHI digestion, was ligated to the linearized pSPZ4R3' vector, resulting in reconstitution of the intact Z4 transcription unit. The resulting vector comprised a Z27promoter::Nos 3' region construct in pBSK(−) which contained a unique NcoI site between the promoter and terminator. Both the vector and insert were blunt-ended and ligated. Clones were identified with the sense orientation of the Z4 DNA sequence (pDPG531). pDPG531 is capable of being transcribed and translated into the 22 kD zein protein (α-zein). Plasmid pDPG531 and pDPG165 were introduced into maize cells by co-bombardment as follows.

Transformants were regenerated as described in PCT publication WO 95/06128 and U.S. Pat. Ser. No. 08/763, 704, Dec. 9, 1996; both of the disclosures of which are specifically incorporated herein by reference in their entirety. The procedure was as follows: maize plants of the genotype A188×B73 were crossed to Hi-II maize plants (Armstrong et al., 1991). Immature embryos (1.2–2.0 mm in length) were excised from surface-sterilized, greenhouse-grown ears of Hi-II 11–12 days post-pollination. The Hi-II genotype was developed from an A188×B73 cross for high frequency development of type II callus from immature embryos (Armstrong et al., 1991). Approximately 30 embryos per petri dish were plated axis side down on a modified N6 medium containing 1 mg/l 2,4-D, 100 mg/l casein hydrolysate, 6 mM L-proline, 0.5 g/l 2-(N-morpholino)ethanesulfonic acid (MES), 0.75 g/l MgCl$_2$, and 2% sucrose solidified with 2 g/l Gelgro, pH 5.8 (#735 medium) Embryos were cultured in the dark for two to four days at 24° C.

Approximately four hours prior to bombardment, embryos were transferred to the above culture medium with the sucrose concentration increased from 3% to 12%. When embryos were transferred to the high osmoticum medium they were arranged in concentric circles on the plate, starting 2 cm from the center of the dish, positioned such that their coleorhizal end was orientated toward the center of the dish. Usually two concentric circles were formed with 25–35 embryos per plate. The plates containing embryos were placed on the third shelf from the bottom, 5 cm below the stopping screen in the bombardment chamber. 1100 psi rupture discs were used. Each plate of embryos was bombarded once. Embryos were allowed to recover overnight on high osmotic strength medium prior to initiation of selection.

Following recovery on high osmoticum medium (735, 12% sucrose) overnight (16–24 hours), embryos were transferred to selection medium containing 1 mg/l bialaphos (#739, 735 plus 1 mg/l bialaphos or #750, 735 plus 0.2M mannitol and 1 mg/l bialaphos). Embryos were maintained in the dark at 24° C. After three to four week on the initial selection plates about 90% of the embryos had formed Type II callus and were transferred to selective medium containing 3 mg/l bialaphos (#758). Bialaphos resistant tissue was subcultured about every two weeks onto fresh selection medium (#758). Transformed embryogenic callus was transferred to regeneration culture medium (MS culture medium (Murashige and Skoog, 1962), containing 0.91 mg/L L-asparagine, 1.4 g/L L-proline, 20 g/L D-sorbitol, 0.04 mg/L naphthalene acetic acid (NAA) and 3 mg/L 6-benzylaminopurine). Cells were grown for about four weeks on this culture medium with a transfer to fresh medium at about 2 weeks. Transformants were subsequently transferred to MS0 culture medium (MS medium with no phytohormones added). Regenerated plants were transferred to soil. Plants were crossed to maize inbred lines designated AW, CV, and DJ. Seed containing the Z27-sense expression cassette were opaque in phenotype similar to kernels of opaque-2 mutant kernels. Plants were regenerated from three Z27-Z4 sense expression cassettes and crossed to inbreds designated AW, CV, and CN.

The amount of α-zein proteins present in untransformed maize plants and Z27-Z4 sense transformants was compared on Coomassie blue stained polyacrylamide gels as described below. Fifty milligrams of ground kernel was suspended in 0.5 ml 70% ethanol, 1% β-mercaptoethanol and extracted at room temperature for 30 minutes to overnight. The sample was vortexed, and centrifuged at 12,000 rpm for 5 minutes. Fifty microliters of the supernatant containing zein proteins was removed and dried. Zein proteins were resuspended in 50:1 SDS polyacrylamide gel loading buffer containing 1% β-mercaptoethanol. Protein was separated on SDS polyacrylamide gels and stained with Coomassie blue.

The results demonstrated a surprising reduction in the levels of α-zein proteins present in Z27-Z4 sense transformants. The reduction was comparable to that observed in antisense transformants. In addition to the unexpected reduction in zein protein concentration in sense transformants, seeds with reduced zein content also generally exhibited the opaque phenotype, and a reduction in Z27 zein levels.

Lysine and leucine concentrations were also analyzed in seed derived from individual kernels. Amino acids were extracted from mature kernels derived from three independent transformed lines as follows. Fifty milligrams of ground corn meal was hydrolyzed in 1 ml 6N HCl under argon gas for 24 hours at 110° C. Samples were diluted to 50 ml and filtered through a 0.45 micron filter. Norvaline was added to each sample as an internal standard prior to HPLC analysis. Amino acids were separated on a Supelcosil LC-8 HPLC column (Jarrett et al., 1986; Jones et al., 1983; AACC, 1995). Results from analysis of single kernels revealed differences between transformed and untransformed kernels that were significant at the $p<0.05$ level of significance. In one transformant, designated KQ018, lysine and leucine levels were statistically the same in isogenic transformed and untransformed seed. However, in a transformant designated KQ012, lysine levels were statistically increased in the transformant and leucine levels were statistically significantly decreased in the transformant. It is therefore indicated that the Z27 promoter- Z4 sense transformants produce a seed morphology, protein, and amino acid composition phenotype similar to that observed in antisense transformants. This is believed to occur as a results of homology-dependent gene silencing.

In order to demonstrate that homology based gene silencing does not occur when the maize Z27 promoter is replaced with a Coix promoter from the homologous Coix gene, a plasmid vector is constructed comprising a promoter isolated from the Coix gene homologous to the Z27 gene, and this promoter is operably linked to the *Zea mays* Z4 coding sequence. The promoter sequence is isolated using the strategy described in Example 1. The Coix-promoter-Z4 coding sequence vector is then transformed into maize as described above. Transgenic plants containing the vector are regenerated as described above and crossed to untransformed inbreds. The amount of α-zeins are then measured to demonstrate a lack of reduction in transgene expression in transformants comprising the Coix derived promoter-Z4 structural gene expression cassette. Furthermore, increased expression of the Coix derived promoter-Z4 structural gene expression cassette relative to the native promoter containing transformants is demonstrated by the lack of an opaque phenotype in the plants having a Coix derived promoter-Z4 structural gene expression cassette . Analysis of lysine and leucine concentrations in the Coix promoter-Z4 structural gene expression cassette transformants is also carried out to demonstrate that lysine levels are not increased and leucine levels are not decreased, thereby indicating that sense co-suppression is not observed in maize transformants comprising a promoter derived from Coix, as was observed using the maize Z27 promoter.

Example 9

Transformation of H99 Immature Embryos or Callus and Selection With Paromomycin

Maize immature embryos (1.2–3.0 mm, 10–14 days post pollination) are isolated from greenhouse grown H99 plants that have been self or sib pollinated. Immature embryos are cultured on 735 medium in the dark at approximately 27° C. Immature embryos are either bombarded 1–6 days after isolation or cultured to produce embryogenic callus that is used for bombardment. Embryogenic callus is expanded and maintained by subculturing at 2–3 week intervals to fresh 735 medium. Prior to bombardment, cultured embryos or embryogenic callus (subdivided in approximately 2–4 mm clumps) are transferred to 735 medium containing 12% sucrose for 3–6 hours. Following bombardment, carried out as described in Example 6, tissue cultures are incubated overnight and transferred to 735 medium containing 500 mg/L paromomycin. After 2–3 weeks, callus is subdivided into small pieces (approximately 2–4 mm in diameter) and transferred to fresh selection medium. This subculture step is repeated at 2–3 week intervals for up to about 15 week post-bombardment, with subdivision and visual selection for healthy, growing callus.

Paromomycin tolerant callus is transferred to 735 medium without 2,4-D but containing 3.52 mg/L BAP for 3–9 days in the dark at approximately 27° C. and is subsequently transferred to 110 medium (½×MS salts, 0.5 mg/L thiamine, 0.5 mg/L nicotinic acid, 3% sucrose, 3.6 g/L Gelgro, pH 5.8) containing 100 mg/L paromomycin in Phytatrays (Sigma) and cultured at about 27° C. in the light. Planlets that develop in Phytatrays after 3–6 weeks are then transferred to soil. Planlets are acclimated in a growth chamber and grown to maturity in the greenhouse.

Example 10

General Methods for Microprojectile Bombardment

Many variations in techniques for microprojectile bombardment are well known in the art and therefore deemed useful with the current invention. Exemplary procedures for bombardment are discussed in, for example, PCT Application WO 95/06128, specifically incorporated herein by reference in its entirety. Examples of target tissues which may be used with the current invention include immature embryos, Type I callus, Type II callus, Type III callus, suspension cultures and meristematic tissue (PCT Application WO 96/04392). Some genotypes which are especially useful for maize transformation are specifically disclosed herein above, as well as in, for example, PCT Application WO 95/06128. Preferred genotypes will be those which are readily transformable and which may also be regenerated to yield a fertile transgenic plant.

Any method for acceleration of microprojectiles may potentially be used to transform a plant cell with the current invention. A preferred method will be a gas-driven particle gun such as the DuPont Biolistics PDS1000He particle bombardment device. Exemplary particles for bombardment include those comprised of tungsten, gold, platinum, and the like. Gold particles are deemed particularly useful in the current invention, with 0.6 $\mu$m or 0.7 $\mu$m gold particles being preferred and 0.6 $\mu$m particles most preferred. The most preferred particles will be DNA coated and have a mean size between 0.6 $\mu$m and 1.0 $\mu$m.

As disclosed herein, any DNA sequence may potentially be used for transformation. The DNA segments used for transformation will preferably include one or more selectable, secretable or screenable markers. Many examples of such are well known in the art and are specifically disclosed herein. In the case of selectable markers, selection may be in solid or liquid media. The DNA segments used will preferably also include one or more genes which confer, either individually or in combination with other sequences, a desired phenotype on the transformed plant. Exemplary genes for transformation and the corresponding phenotypes these sequences may confer on the transformed plant are disclosed herein.

Example 11

Introgression of Transgenes Into Elite Inbreds and Hybrids

Backcrossing can be used to improve a starting plant. Backcrossing transfers a specific desirable trait from one source to an inbred or other plant that lacks that trait. This can be accomplished, for example, by first crossing a superior inbred (A) (recurrent parent) to a donor inbred (non-recurrent parent), which carries the appropriate gene(s) for the trait in question, for example, a construct prepared in accordance with the current invention. The progeny of this cross first are selected in the resultant progeny for the desired trait to be transferred from the non-recurrent parent, then the selected progeny are mated back to the superior recurrent parent (A). After five or more backcross generations with selection for the desired trait, the progeny are hemizygous for loci controlling the characteristic being transferred, but are like the superior parent for most or almost all other genes. The last backcross generation would be selfed at least once to give progeny which are pure breeding for the gene(s) being transferred, i.e. one or more transformation events.

Therefore, through a series a breeding manipulations, a selected transgene may be moved from one line into an entirely different line without the need for further recombinant manipulation. Transgenes are valuable in that they typically behave genetically as any other gene and can be manipulated by breeding techniques in a manner identical to any other corn gene. Therefore, one may produce inbred plants which are true breeding for one or more transgenes. By crossing different inbred plants, one may produce a large number of different hybrids with different combinations of transgenes. In this way, plants may be produced which have the desirable agronomic properties frequently associated with hybrids ("hybrid vigor"), as well as the desirable characteristics imparted by one or more transgene(s).

Example 12

Marker Assisted Selection

Genetic markers may be used to assist in the introgression of one or more transgenes of the invention from one genetic background into another. Marker assisted selection offers advantages relative to conventional breeding in that it can be used to avoid errors caused by phenotypic variations. Further, genetic markers may provide data regarding the relative degree of elite germplasm in the individual progeny of a particular cross. For example, when a plant with a desired trait which otherwise has a non-agronomically desirable genetic background is crossed to an elite parent, genetic markers may be used to select progeny which not only possess the trait of interest, but also have a relatively large proportion of the desired germplasm. In this way, the number of generations required to introgress one or more traits into a particular genetic background is minimized.

In the process of marker assisted breeding, DNA sequences are used to follow desirable agronomic traits (Tanksley et al., 1989) in the process of plant breeding. Marker assisted breeding may be undertaken as follows. Seed of plants with the desired trait are planted in soil in the greenhouse or in the field. Leaf tissue is harvested from the plant for preparation of DNA at any point in growth at which approximately one gram of leaf tissue can be removed from the plant without compromising the viability of the plant. Genomic DNA is isolated using a procedure modified from Shure et al. (1983). Approximately one gram of leaf tissue from a seedling is lypholyzed overnight in 15 ml polypropylene tubes. Freeze-dried tissue is ground to a powder in the tube using a glass rod. Powdered tissue is mixed thoroughly with 3 ml extraction buffer (7.0 urea, 0.35 M NaCl, 0.05 M Tris-HCl pH 8.0, 0.01 M EDTA, 1% sarcosine). Tissuelbuffer homogenate is extracted with 3 ml phenol/ chloroform. The aqueous phase is separated by centrifugation, and precipitated twice using 1/10 volume of 4.4 M ammonium acetate pH 5.2, and an equal volume of isopropanol. The precipitate is washed with 75% ethanol and resuspended in 100–500 µl TE (0.01 M Tris-HCl, 0.001 M EDTA, pH 8.0).

Genomic DNA is then digested with a 3-fold excess of restriction enzymes, electrophoresed through 0.8% agarose (FMC), and transferred (Southern, 1975) to Nytran (Schleicher and Schuell) using 10×SCP (20 SCP:2M NaCl, 0.6 M disodium phosphate, 0.02 M disodium EDTA). The filters are prehybridized in 6×SCP, 10% dextran sulfate, 2% sarcosine, and 500 µg/ml denatured salmon sperm DNA and $^{32}$P-labeled probe generated by random priming (Feinberg & Vogelstein, 1983). Hybridized filters are washed in 2×SCP, 1% SDS at 65° for 30 minutes and visualized by autoradiography using Kodak XAR5 film. Genetic polymorphisms which are genetically linked to traits of interest are thereby used to predict the presence or absence of the traits of interest.

Those of skill in the art will recognize that there are many different ways to isolate DNA from plant tissues and that there are many different protocols for Southern hybridization that will produce identical results. Those of skill in the art will recognize that a Southern blot can be stripped of radioactive probe following autoradiography and re-probed with a different probe. In this manner one may identify each of the various transgenes that are present in the plant. Further, one of skill in the art will recognize that any type of genetic marker which is polymorphic at the region(s) of interest may be used for the purpose of identifying the relative presence or absence of a trait, and that such information may be used for marker assisted breeding.

Each lane of a Southern blot represents DNA isolated from one plant. Through the use of multiplicity of gene integration events as probes on the same genomic DNA blot, the integration event composition of each plant may be determined. Correlations may be established between the contributions of particular integration events to the phenotype of the plant. Only those plants that contain a desired combination of integration events may be advanced to maturity and used for pollination. DNA probes corresponding to particular transgene integration events are useful markers during the course of plant breeding to identify and combine particular integration events without having to grow the plants and assay the plants for agronomic performance.

It is expected that one or more restriction enzymes will be used to digest genomic DNA, either singly or in combinations. One of skill in the art will recognize that many different restriction enzymes will be useful and the choice of restriction enzyme will depend on the DNA sequence of the transgene integration event that is used as a probe and the DNA sequences in the genome surrounding the transgene. For a probe, one will want to use DNA or RNA sequences which will hybridize to the DNA used for transformation. One will select a restriction enzyme that produces a DNA fragment following hybridization that is identifiable as the transgene integration event. Thus, particularly useful restriction enzymes will be those which reveal polymorphisms that are genetically linked to specific transgenes or traits of interest.

Example 13

General Methods for Assays

DNA analysis of transformed plants is performed as follows. Genomic DNA is isolated using a procedure modified from Shure, et al., 1983. Approximately 1 gm callus or leaf tissue is round to a fine powder in liquid nitrogen using a mortar and pestle. Powdered tissue is mixed thoroughly with 4 ml extraction buffer (7.0 M urea, 0.35 M NaCl, 0.05 M Tris-HCl pH 8.0, 0.01 M EDTA, 1% sarcosine). Tissue/buffer homogenate is extracted with 4 ml phenol/chloroform. The aqueous phase is separated by centrifugation, passed through Miracloth; and precipitated twice using 1/10 volume of 4.4 M ammonium acetate, pH 5.2 and an equal volume of isopropanol. The precipitate is washed with 70% ethanol and resuspended in 200–500 ml TE (0.01 M Tris-HCl, 0.001 M EDTA, pH 8.0).

The presence of a DNA sequence in a transformed cell may be detected through the use of polymerase chain reaction (PCR). Using this technique specific fragments of DNA can be amplified and detected following agarose gel electrophoresis. For example, two hundred to 1000 ng genomic DNA is added to a reaction mix containing 10 mM Tris-HCl pH 8.3, 1.5 mM $MgCl_2$, 50 mM KCl, 0.1 mg/ml gelatin, 200 µM each dATP, dCTP, dGTP, dTTP, 0.5 µM each forward and reverse DNA primers, 20% glycerol, and 2.5 units Taq DNA polymerase. The reaction is run in a thermal cycling machine as follows: 3 minutes at 94 C, 39 repeats of the cycle 1 minute at 94 C, 1 minute at 50 C, 30 seconds at 72 C, followed by 5 minutes at 72 C. Twenty µl of each reaction mix is run on a 3.5% NuSieve gel in TBE buffer (90 mM Tris-borate, 2 mM EDTA) at 50V for two to four hours. Using this procedure, for example, one may detect the presence of the bar gene, using the forward primer CATCGAGACAAGCACGGTCAACTTC (SEQ ID NO:20) and the reverse primer AAGTCCCTGGAGGCACAGGGCTTCAAGA (SEQ ID NO:21).

A method to detect the presence of phosphinothricin acetyl transferase (PAT) involves the use of an in vitro enzyme reaction followed by thin layer chromatography, as described in PCT Application WO 95/06128 (specifically incorporated herein by reference in its entirety). The procedure is conducted by preparing various protein extracts from homogenates of potentially transformed cells, and from control cells that have neither been transformed nor exposed to bialaphos selection, and then assaying by incubation with PPT and $^{14}$C-Acetyl Coenzyme A followed by thin layer chromatography. The results of this assay provide confirmation of the expression of the bar gene which codes for PAT.

For Southern blot analysis genomic DNA is digested with a 3-fold excess of restriction enzymes, electrophoresed through 0.8% agarose (FMC), and transferred (Southern, 1975) to Nytran (Schleicher and Schuell) using 10×SCP (20×SCP:2 M NaCl, 0.6 M disodium phosphate, 0.02 M disodium EDTA). Probes are labeled with $^{32}$P using the random priming method (Boehringer Mannheim) and purified using Quik-Sep® spin columns (Isolab Inc., Akron, Ohio). Filters are prehybridized at 65° C. in 6×SCP, 10% dextran sulfate, 2% sarcosine, and 500 µg/ml heparin (Chomet et al., 1987) for 15 min. Filters then are hybridized overnight at 65 C in 6×SCP containing 100 µg/mi denatured salmon sperm DNA and $^{32}$P-labeled probe. Filters are washed in 2×SCP, 1% SDS at 65 C for 30 min. and visualized by autoradiography using Kodak XAR5 film. For rehybridization, the filters are boiled for 10 min. in distilled $H_2O$ to remove the first probe and then prehybridized as described above.

Example 14

Utilization of Transgenic Crops

The ultimate goal in plant transformation is to produce plants which are useful to man. In this respect, transgenic plants created in accordance with the current invention may be used for virtually any purpose deemed of value to the grower or to the consumer. For example, one may wish to harvest seed from transgenic plants. This seed may in turn be used for a wide variety of purposes. The seed may be sold to farmers for planting in the field or may be directly used as food, either for animals or humans. Alternatively, products may be made from the seed itself. Examples of products which may be made from the seed include, oil, starch, animal or human food, pharmaceuticals, and various industrial products. The food uses of maize, in addition to human consumption of maize kernels, include both products of dry- and wet-milling industries. The principal products of maize dry milling are grits, meal and flour. The maize wet-milling industry can provide maize starch, maize syrups, and dextrose for food use. Maize oil is recovered from maize germ, which is a by-product of both dry- and wet-milling industries.

Maize, including both grain and non-grain portions of the plant, is also used extensively as livestock feed, primarily for beef cattle, dairy cattle, hogs, and poultry. Industrial uses of maize include production of ethanol, maize starch in the wet-milling industry and maize flour in the dry-milling industry. The industrial applications of maize starch and flour are based on functional properties, such as viscosity, film formation, adhesive properties, and ability to suspend particles. The maize starch and flour have application in the paper and textile industries. Other industrial uses include applications in adhesives, building materials, foundry binders, laundry starches, explosives, oil-well muds, and other mining applications. Plant parts other than the grain of maize are also used in industry, for example, stalks and husks are made into paper and wallboard and cobs are used for fuel and to make charcoal. Other means for utilizing plants, such as those that may be made with the current invention, have been well known since the dawn of agriculture and will be known to those of skill in the art in light of the instant disclosure. Specific methods for crop utilization may be found in, for example, Sprague and Dudley (1988), and Watson and Ramstad (1987).

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the compositions and methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved.

REFERENCES

The references listed below are incorporated herein by reference to the extent that they supplement, explain, provide a background for, or teach methodology, techniques, and/or compositions employed herein.

Abel et al., *Science*, 232:738–743, 1986.
Araki et al., "Site-specific recombinase, R, encoded by yeast plasmid pSR1," *J. Mol. Biol.* 225(1):25–37, 1992.
Armstrong et al., *Maize Genetics Coop Newsletter*, 65:92–93, 1991.
Assad, Tucker, Signer, "Epigenetic repeat-induced gene silencing (RIGS) in *Arabidopsis*," *Plant Mol. Biol.*, 22:1067–85, 1993.
Bansal, Viret, Haley, Khan, Schantz, Bogorad, "Transient expression from cab-m1 and rbcS-m3 promoter sequence is different in mesophyll and bundle sheath cells in maize leaves," *Proc. Natl. Acad. Sci. USA*, 89:3654–3658, 1992.
Barkai-Golan et al., *Arch. Microbiol.*, 116:119–124, 1978.
Barton et al., *Plant Physiol.*, 85:1103–1109, 1987.
Bates, "Genetic transformation of plants by protoplast electroporation," *Mol. Biotechnol.*, 2(2):135–145, 1994.
Battraw and Hall, "Stable transformation of sorghum-bicolor protoplasts with chimeric neomycin phosphotransferase II and beta glucuronidase genes," *Theor. App. Genet.*, 82(2):161–168, 1991.
Battraw and Hall, "Stable transformation of sorghum-bicolor protoplasts with chimeric neomycin phosphotransferase II and beta glucuronidase genes," *Theor. Appl. Genet.* 82(2):161–168, 1991.
Belanger and Kriz, "Molecular basis for allelic polymorphism of the maize globulin-1 gene," *Genet.*, 129:863–872, 1991.
Bellus, J. *Macromol. Sci. Pure Appl. Chem.*, A31(1):1355–1376, 1994.
Bernal-Lugo and Leopold, *Plant Physiol.*, 98:1207–1210, 1992.
Bevan et al., "Structure and transcription of the nopaline synthase gene region of T-DNA," *Nucleic Acids Research*, 11(2):369–385, 1983.
Bhattacharjee; An; Gupta, "Fertile transgenic indica rice produced by expression of maize ubiquitin promoter-bar chimeric gene in the protoplasts," *J. Plant Bioch. and Biotech.* 6, (2):69–73. 1997.
Blackman et al., *Plant Physiol*, 100:225–230, 1992.
Bol et al., *Annu. Rev. Phytopath.*, 28:113–138, 1990.
Bouchez et al., *EMBO Journal*, 8(13):4197–4204, 1989.
Bower et al., "Transgenic Sugarcane Plants vis Microprojectile Bombardment," *The Plant Journal*, 2:409–416. 1992.
Bowler et al., *Ann Rev. Plant Physiol*, 43:83–116, 1992.
Branson and Guss, *Proceedings North Central Branch Entomological Society of America*, 27:91–95, 1972.
Broakaert et al., *Science*, 245:1100–1102, 1989.
Buising and Benbow, "Molecular analysis of transgenic plants generated by microprojectile bombardment: effect of petunia transformation booster sequence," *Mol. Gen Genet*, 243(1):71–81. 1994.
Callis et al., "Introns increase gene expression in cultured maize cells," *Genes and Development*, 1:1183–1200, 1987.
Campbell (ed.), In: *Avermectin and Abamectin*, 1989.
Capaldi et al., *Biochem. Biophys. Res. Comm.*, 76:425, 1977.
Casas, Kononowicz, Zehr, Tomes, Axtell, Butler, Bressan, Hasegawa, "Transgenic sorghum plants via microprojectile bombardment," *Proc. Natl. Acad. Sci. USA*, 90(23):11212–11216, 1993.
Chandler et al., "Two Regulatory Genes of the Maize Anthocyanin Pathway Are Homologous: Isolation of B Utilizing R Genomic Sequences," *The Plant Cell*, 1:1175–1183, 1989.
Chau et al., *Science*, 244:174–181, 1989.
Chomet et al., *EMBO J.*, 6:295–302, 1987.
Christou; Murphy; Swain, "Stable transformation of soybean by electroporation and root formation from transformed callus," *Proc. Natl. Acad. Sci. USA*, 84(12):3962–3966, 1987.
Chu et al., *Scientia Sinica*, 18:659–668, 1975.
Coe et al., In. *Corn and Corn Improvement*, 81–258, 1988.
Conkling et al., *Plant Physiol.*, 93:1203–1211, 1990.
Consonni, Geuna, Gavazzi, Tonelli, "Molecular homology among members of the R gene family in maize," *Plant J.*, 3(2):335–346, 1993.

Cordero, Raventos, San Segundo, "Expression of a maize proteinase inhibitor gene is induced in response to wounding and fungal infection: systemic wound-response of a monocot gene," *Plant J.*, 6(2)141–150, 1994.

Coxson et al., *Biotropica*, 24:121–133, 1992.

Cristou et al., *Plant Physiol.*, 87:671–674, 1988.

Cuozzo et al., *Bio/Technology*, 6:549–553, 1988.

Cutler et al., *J. Plant Physiol.*, 135:351–354, 1989.

Czapla and Lang, *J. Econ. Entomol.*, 83:2480–2485, 1990.

Davies et al., *Plant Physiol.*, 93:588–595, 1990.

De Block, Botterman, Vandewiele, Dockx, Thoen, Gossele, Movva, Thompson, Van Mantagu, Leemans, "Engineering herbicide resistance in plants by expression of a detoxifying enzyme," *The EMBO Journal*, 6(9):2513–2518, 1987.

De Block, De Brouwer, Tenning, "Transformation of *Brassica napus* and *Brassica oleracea* Using *Agrobacterium tumefaciens* and the Expression of the bar and neo Genes in the Transgenic Plants," *Plant Physiol.*, 91:694–701, 1989.

Dehio and Schell, "Identification of plant genetic loci involved in a posttranscriptional mechanism for meiotically reversible transgene silencing," *Proc. Natl. Acad. Sci. USA*, 91:5538–5542, 1994.

Dellaporta et al., "A plant DNA minipreparation: version II," *Plant Mol. Biol. Rep.*, 1:19–21, 1983.

Dellaporta et al., In. *Chromosome Structure and Function. Impact of New Concepts*, 18th Stadler Genetics Symposium, 11:263–282, 1988.

Dennis, Gerlach, Pryor, Bennetzen, Inglis, Llewellyn, Sachs, Ferl, Peacock, "Molecular analysis of the alcohol dehydrogenase (Adh 1) gene of maize," *Nucl. Acids Res.*, 12(9):3983–4000, 1984.

Depicker et al., *Plant Cell Reports*, 7:63–66, 1988.

D'Halluin, K., Bonne, E., Bossut, M. De Beuckeleer, M., and Leemans, J. *The Plant Cell* 4: 1495–1505. 1992

Dhir; Dhir; Savka; Belanger; Kriz; Farrand; Widholm, "Regeneration of transgenic soybean glycine-max plants from electroporated protoplasts," *Plant Physiol*, 99(1) 81–88, 1992.

Dunn et al., *Can. J. Plant Sci.*, 61:583, 1981.

Dure et al., *Plant Molecular Biology*, 12:475–486, 1989.

Ellis et al., *EMBO Journal*, 6(11):3203–3208, 1987.

Enomoto M, et al., "Mapping of the pin locus coding for a site-specific recombinase that causes flagellar-phase variation in *Escherichia coli* K-12". *J. Bacteriol.*, 6(2):663–668. 1983.

Erdmann et al., *J. Gen. Microbiology*, 138:363–368, 1992.

Feinberg and Vogelstein, *Anal. Biochem.*, 132:6–13, 1983.

Finkle et al., *Plant Sci.*, 42:133–140, 1985.

Fitzpatrick, "Pleiotropic Gene Found in Barley Plant," *Genetic Engineering News*, 13(5):1,22, 1993.

Fitzpatrick, *Gen. Engineering News*, 22:7, 1993.

Fodor et al., "Light-directed, spatially addressable parallel chemical synthesis," *Science*, 251:767–773, 1991.

Franken, Niesbach-Klosgen, Weydemann, Marechal-Drouard, Saedler, Wienand, "The duplicated chalcone synthase genes C2 and Whp (white pollen) of *Zea mays* are independently regulated; evidence for translational control of Whp expression by the anthocyanin gene," *EMBO J.*, 10(9):2605–2612, 1991.

Fransz, de Ruijter, Schel, "Isoenzymes as Biochemical and Cytochemical Markers in Embryogenic Callus of Maize (*Zea mays* L.)," *Plant Cell Reports*, 8:67–70, 1989.

Freifelder, In. *Physical Biochemistry Applications to Biochemistry and Molecular Biology*, 2nd ed., 1982.

Frohman, In: *PCR™ Protocols: A Guide to Methods and Applications*, 1990.

Fromm et al., *The Plant Cell*, 1:977–984, 1989.

Gallie et al., *The Plant Cell*, 1:301–311, 1989.

Gatehouse et al., *J. Sci. Food Agric.*, 35:373–380, 1984.

Gelvin et al., In: *Plant Molecular Biology Manual*, 1990.

Ghosh-Biswas, Iglesias, Datta, Potrykus, "Transgenic Indica rice (*Oryza sativa* L.) plants obtained by direct gene transfer to protoplasts," *J. Biotechnol.*, 32(1):1–10, 1994.

Golic and Lindquist, *Cell*, 59:3, 499–509. 1989.

Goring et al., *Proc. Natl. Acad. Sci. USA*, 88:1770–1774, 1991.

Grosset, Alary, Gautier, Menossi, Martinez-Izquierdo, Joudrier, "Characterization of a barley gene coding for an alpha-amylase inhibitor subunit (CMd protein) and analysis of its promoter in transgenic tobacco plants and in maize kernels by microprojectile bombardment," *Plant Mol. Biol.*, 34(2):331–338, 1997.

Guerrero et al., *Plant Molecular Biology*, 15:11–26, 1990.

Gupta et al., *Proc. Natl. Acad. Sci. USA*, 90:1629–1633, 1993.

Hacia et al., "Detection of heterozygous mutations in BRCA1 using high density oligonucleotide arrays and two-colour fluorescence analysis," *Nature Genetics*, 14:441–447, 1996.

Hagio, Blowers, Earle, "Stable transformation of sorghum cell cultures after bombardment with DNA coated microprojectiles," *Plant Cell Rep.*, 10(5):260–264, 1991.

Hamilton et al., *Proc. Nat. Acad. Sci. USA*, 93(18):9975–9979, 1996.

Hammock et al., *Nature*, 344:458–461, 1990.

Haseloff, Siemering, Prasher, Hodge, "Removal of a cryptic intron and subcellular localization of green fluorescent protein are required to mark transgenic Arabidopsis plants brightly," *Proc. Natl. Acad. Sci., USA*, 94:2122–2127, 1997.

He; Mouradov; Yang; Mouradova; Scott, "Transformation of wheat (*Triticum aestivum* L.) through electroporation of protoplasts," *Plant Cell Reports*, 14(2–3):192–196, 1994.

Hemenway et al., *The EMBO J.*, 7:1273–1280, 1988.

Hensgens, de Bakker, van Os-Ruygrok, Rueb, van de Mark, van der Maas, van der Veen, Kooman-Gersmann, Schilperoort, "Transient and stable expression of gusA fusions with rice genes in rice, barley and perennial ryegrass," *Plant Mol. Biol.*, 22(6):1101–1127, 1993.

Hilder et al., *Nature*, 330:160–163, 1987.

Hinchee et al., *Bio/technol.*, 6:915–922, 1988.

Hou and Lin, "Rapid optimization of electroporation conditions for soybean and Hudspeth and Grula, *Plant Mol. Biol*, 12:579–589, 1989.

Hou and Lin, *Plant Physiology*, 111:166. 1996

Ikeda et al., *J. Bacteriol.*, 169:5615–5621, 1987.

Ikuta et al., *Bio/technol.*, 8:241–242, 1990.

Ingelbrecht, Van Houdt, Van Montagu, Depicker, "Posttranscriptional silencing of reporter transgenes in tobacco correlates with DNA methylation," *Proc. Natl. Acad. Sci. USA*, 91:10502–10506, 1994.

Johnson et al., *Proc. Natl. Acad. Sci. USA*, 86:9871–9875, 1989.

Jorgensen, "Altered gene expression in plants due to trans interactions between homologous genes," *Trends Biotechnol.*, 8:340–44, 1990.

Jorgensen, "Cosuppression, flower color patterns, and metastable gene expression states," *Science*, 268:686–691, 1995.

Joshi, *Nucleic Acids Res.*, 15:6643–6653, 1987.

Kaasen et al., *J. Bacteriology*, 174:889–898, 1992.

Kaeppler et al., *Plant Cell Reports* 9: 415–418. 1990.

Kaeppler, Somers, Rines, Cockburn, "Silicon carbide fiber-mediated stable transformation of plant cells," *Theor. Appl. Genet.*, 84(5–6):560–566, 1992.

Karsten et al., *Botanica Marina*, 35:11–19, 1992.

Katz et al., *J. Gen. Microbiol.*, 129:2703–2714, 1983.

Keller et al., *EMBO J.*, 8(5):1309–1314, 1989.

Klein, Kornstein, Sanford, Fromm, "Genetic Transformation of Maize Cells by Particle Bombardment," *Plant Physiology*, 91:440–444, 1989.

Knittel, Gruber; Hahne; Lenee, "Transformation of sunflower (*Helianthus annuus* L.): A reliable protocol," *Plant Cell Reports*, 14(2–3):81–86, 1984.

Kohler, Liaud, Mendel, Cerff, Hehl, "The maize GapC4 promoter confers anaerobic reporter gene expression and shows homology to the maize anthocyanin regulatory locus C1," *Plant Mol. Biol.*, 29(6):1293–1298, 1995.

Koster and Leopold, *Plant Physiol.*, 88:829–832, 1988.

Kriz, Boston, Larkins, "Structural and transcriptional analysis of DNA sequences flanking genes that encode 19 kilodalton zeins," *Mol. Gen. Genet.*, 207(1):90–98, 1987.

Kunkel, T. A. et al., "Rapid and efficient site-specific mutagenesis without phenotypic selection," *Methods Enzymol*, 154:367–382, 1987.

Kwoh et al., *Proc. Natl. Acad. Sci. USA*, 86:1173, 1989.

Langridge and Feix, "A zein gene of maize is transcribed from two widely separated promoter regions," *Cell*, 34:1015–1022, 1983.

Laufs et al., *Proc. Natl. Acad. Sci.*, 7752–7756, 1990.

Lazzeri, "Stable transformation of barley via direct DNA uptake. Electroporation- and PEG-mediated protoplast transformation," *Methods Mol. Biol.*, 49:95–106, 1995.

Lee and Saier, *J. of Bacteriol.*, 153–685, 1983.

Lee; Suh; Lee, "Gene transfer into intact cells of tobacco by electroporation," *Korean J. Genet*, 11(2):65–72, 1989.

Levings, *Science*, 250:942–947, 1990.

Lindbo, Silva-Rosales, Proebsting, Dougherty, "Induction of a highly specific antiviral state in transgenic plants: implications for gene regulation and virus resistance," *Plant Cell*, 5:1749–1759, 1993.

Lindstrom et al., *Developmental Genetics*, 11:160, 1990.

Loomis et al., *J. Expt. Zoology*, 252:9–15, 1989.

Ma et al., *Nature*, 334:631–633, 1988.

Maas, Reichel, Schell, Steinbiss, "Preparation and transformation of monocot protoplasts," *Methods Cell Biol.*, 50:383–399, 1995.

Maeser et al., "The Gin recombinase of phage Mu can catalyse site-specific recombination in plant protoplasts," *Mol. Gen Genet.*, 230(1–2):170–176, 1991.

Mariani et al., *Nature*, 347:737–741, 1990.

Martinez, Martin, Cerff, "Structure, evolution and anaerobic regulation of a nuclear gene encoding cytosolic glyceraldehyde-3-phosphate dehydrogenase from maize," *J. Mol. Biol.*, 208(4):551–565, 1989.

Matzke and Matzke, "How and why do plants inactivate homologous (trans)genes?," *Plant Physiol.*, 107:679–685, 1995.

Matzke, Neuhuber, Matzke, "A variety of epistatic interactions can occur between partially homologous transgene loci brought together by sexual crossing," *Mol. Gen. Genet.*, 236:379–86, 1993.

Matzke, Neuhuber, Park, Ambros, Matzke, "Homology-dependent gene silencing in transgenic plants: epistatic silencing loci contain multiple copies of methylated transgenes," *Mol. Gen. Genet.*, 244:219–229, 1994.

Matzke, Priming, Trnovsky, Matzke, "Reversible methylation and inactivation of marker genes in sequentially transformed tobacco plants," *EMBO J.*, 8:643–49, 1989.

Meyer, "Understanding and controlling transgene expression," *Trends Biotechnol.*, 13:332–337, 1995.

Meyer, Heidmann, Niedenhof, "Differences in DNA-methylation are associated with a paramutation phenomenon in transgenic petunia," *Plant J.*, 4:86–100, 1993.

Mittlesten, Scheid, Paszkowski, Potrykus, "Reversible inactivation of a transgene in *Arabidopsis thaliana*," *Mol. Gen. Genet*, 228:104–12, 1991.

Mueller, Gilbert, Davenport, Birgnetic, Baulcombe, "Homology-dependent resistance transgenic virus resistance in plants related to homology-dependent gene silencing," *Plant J.*, 7:1001–1013, 1995.

Mundy and Chua, The *EMBO J.*, 7:2279–2286, 1988.

Murakami, Anzai, Imai, Satoh, Nagaoka, Thompson, "The bialaphos biosynthetic genes of *Streptomices hygroscopicus*: Molecular cloning and characterization of the gene cluster," *Mol. Gen. Genet.*, 205:42–50, 1986.

Murashige and Skoog, *Physiol. Plant.*, 15:473–497, 1962.

Murdock et al., *Phytochemistry*, 29:85–89, 1990.

Murray et al., *Nucleic Acids Research* 17:477–498, 1989.

Nagatani, Honda, Shimada, Kobayashi, "DNA delivery into rice cells and transformation using silicon carbide whiskers," *Biotech. Tech.*, 11(7):471–473, 1997.

Napoli, Lemieux, Jorgensen, "Introduction of a chimeric chalcone synthase gene into petunia results in reversible co-suppression of homologous genes in trans," *Plant Cell*, 2:279–289, 1990.

Neuhuber, Park, Matzke, Matzke, "Susceptibility of transgene loci to homology-dependent gene silencing," *Mol. Gen. Genet.*, 244:230–241, 1994.

Newton, Winberg, Yamato, Lupold, Stern, "Evidence for a novel mitochondrial preceding the cox2 gene of perennial teosintes," *EMBO J.*, 14(3):585–593, 1995.

Niebel, Frendo, Van Montagu, Cornelissen, "Post-transcriptional cosuppression of β-1,3-glucanase genes does not affect accumulation of transgene nuclear mRNA," *Plant Cell*, 7:347–358, 1995.

Odell et al., "Identification of DNA sequences required for activity of the cauliflower mosaic virus 35S promoter," *Nature*, 313:810–812, 1985.

Ogawa et al., *Sci. Rep.*, 13:42–48, 1973.

Ohara et al., *Proc. Natl. Acad. Sci. USA*, 86:5673–5677, 1989.

Omirulleh et al., "Activity of a Chimeric Promoter with the Doubled CaMV 35S Enhancer Element in Protoplast-Derived Cells and Transgenic Plants in Maize," *Plant Molecular Biology*, 21:415–428, 1993.

Omirulleh, Abraham, Golovkin, Stefanov, Karabaev, Mustardy, Morocz, Dudits, "Activity of a chimeric promoter with the doubled CaMV 35S enhancer element in protoplast-derived cells and transgenic plants in maize," *Plant Mol. Biol.*, 21(3):415–428, 1993.

Ow et al., *Science*, 234:856–859, 1986.

Park, Papp, Moscone, Iglesias, Vaucheret, Matzke, Matzke, "Gene silencing mediated by promoter homology occurs at the level of transcription and results in meiotically heritable alterations in methylation and gene activity," *Plant*, 9:183–194, 1996.

Paul and Ferl, "In vivo footprinting reveals unique cis-elements and different modes of hypoxic induction in maize Adh1 and Adh2," *Plant Cell*, 3(2):159–168, 1991.

Pease et al., "Light-generated oligonucleotide arrays for rapid DNA sequence analysis," *Proc. Natl. Acad. Sci. USA*, 91:5022–5026, 1994.

Perlak et al., *Proc. Natl. Acad. Sci. USA*, 88:3324–3328, 1991.

Phi-Van et al., *Mol. Cell. Biol.*, 10:2302–2307. 1990.

Piatkowski et al., *Plant Physiol.*, 94:1682–1688, 1990.
Pignon et al., *Hum. Mutat.*, 3:126–132, 1994.
Poszkowski et al., *EMBO J.*, 3:2719, 1989.
Potrykus etal., *Mol. Gen. Genet.*, 199:183–188, 1985.
Prasher et al., *Biochem. Biophys. Res. Commun.*, 126(3):1259–1268, 1985.
Prols and Meyer, "The methylation patterns of chromosomal integration regions influence gene activity of transferred DNA in *Petunia hybrida*," *Plant J.*, 2:465–75, 1992.
Quigley, Brinkman, Martin, Cerff, "Strong functional GC pressure in a light-regulated maize gene encoding subunit GAPA of chloroplast glyceraldehyde-3-phosphate dehydrogenase: implications for the evolution of GAPA pseudogenes," *J. Mol. Evol.*, 29(5):412–421, 1989.
Radicella, Turks, Chandler, "Cloning and nucleotide sequence of a cDNA encoding B-Peru, a regulatory protein of the anthocyanin pathway in maize," *Plant Mol. Biol.*, 17(1):127–130, 1991.
Ralston, English, Dooner, "Sequence of three bronze alleles of maize and correlation with the genetic fine structure," *Genet.*, 119(1):185–197, 1988.
Reed et al., *J. Gen. Microbiology*, 130:1–4, 1984.
Reichel, Mathur, Eckes, Langenkemper, Koncz, Schell, Reiss, Maas, "Enhanced green fluorescence by the expression of an Aequorea victoria green fluorescent protein mutant in mono- and dicotyledonous plant cells," *Proc. Natl. Acad. Sci.*, USA, 93:5888–5893, 1996.
Reina, Ponte, Guillen, Boronat, Palau, "Sequence analysis of a genomic clone encoding a Zc2 protein from *Zea mays* W64 A," *Nucl. Acids Res.*, 18(21):6426, 1990.
Rensburg et al., *J. Plant Physiol.*, 141:188–194, 1993.
Rhodes; Marrs; Murry, "Transformation of maize by electroporation of embryos." *Methods Mol. Biol.*, 55:121–131. 1995
Ritala, Aspergren, Kurten, Salmenkallio-Marttila, Mannonen, Hannus, Kauppinen, Teeri, Enari, "Fertile transgenic barley to particle bombardment of immature embryos," *Plant Mol. Biol,*. 24(2):317–325, 1994.
Rochester, Winer, Shah, "The structure and expression of maize genes encoding the major heat shock protein, hsp70," *EMBO J.*, 5:451–458, 1986.
Sabl and Laird, "Epigene conversion: a proposal with implications for gene mapping in humans," *Am. J. Hum. Genet.*, 50:1171–1177, 1992.
Sambrook, Fritsch, and Maniatis, *In Molecular Cloning: A Laboratory Manual*, Second edition, Cold Spring Harbor Laboratory, Cold Spring Harbor, N.Y., 1989.
Sauer, *Mol. and Cell. Biol.*, 7: 2087–2096. 1987.
Schwarz-Sommer, Shepherd, Tacke, Gierl, Rohde, Leclercq, Mattes, Berndtgen, Peterson, Saedler, "Influence of transposable elements on the structure and function of the A1 gene of *Zea mays*," *EMBO J.*, 6:287–294, 1987
Schwob, Choi, Simmons, Migliaccio, Ilag, Hesse, Palme, Soll, "Molecular analysis of three maize 22 kDa auxin-binding protein genes-transient promoter expression and regulatory regions," *Plant J.*, 4:423–432, 1993.
Shagan and Bar-Zvi, *Plant Physiol.*, 101:1397–1398, 1993.
Shapiro, In: *Mobile Genetic Elements*, 1983.
Sheehy, Kramer, Hiatt, "Reduction of polygalacturonase activity in tomato fruit by antisense RNA," *Proc. Natl. Acad. Sci.* USA, 85:8805–8809, 1988.
Sheen et al., *Plant Journal*, 8(5):777–784, 1995.
Shoemaker et al., "Quantitative phenotypic analysis of yeast deletion mutants using a highly parallel molecular barcoding strategy," *Nature Genetics*, 14:450–456, 1996.
Shure et al., *Cell*, 35:225–233, 1983.
Siebert et al., "An improved PCR method of walking in uncloned genomic DNA," *Nucl. Acids Res.*, 23:1087–1088, 1995.
Simpson, *Science*, 233:34, 1986.
Singsit, Adang, Lynch, Anderson, Wang, Cardineau, Ozias-Akins, "Expression of a Bacillus thuringiensis cryIA(c) gene in transgenic peanut plants and its efficacy against lesser cornstalk borer," *Transgenic Res.*, 6(2):169–176, 1997.
Skriver and Mundy, *Plant Cell*, 2:503–512, 1990.
Smith, Swaney, Parks, Wernsman, Dougherty, "Transgenic plant virus resistance mediated by untranslatable sense RNAs: expression, regulation, and fate of nonessential RNAs," *Plant Cell*, 6:1441–1453, 1994.
Smith, Watson, Bird, Ray, Schuch, Grierson, "Expression of a truncated tomato polygalacturonase gene inhibits expression of the endogenous gene in transgenic plants," *Mol. Gen. Genet.*, 224:447–481, 1990.
Southern, "Detection of specific sequences among DNA fragments separated by gel electrophoresis," *J. Mol. Biol.*, 98:503–517, 1975.
Spencer et al., "Segregation of transgenes in maize," *Plant Molecular Biology*, 18:201–210, 1992.
Sprague and Dudley, eds., *Corn and Improvement*, 3rd ed., 1988.
Stalker et al., *J. Biol. Chem.*, 263:6310–6314, 1988.
Stalker et al., *Science*, 242:419–422, 1988.
Stiefel et al., *Nature*, 341:343, 1989.
Stiefel et al., *The Plant Cell*, 2:785–793, 1990.
Stougaard, *The Plant Journal*, 3:755–761, 1993.
Sullivan et al., *Mol. Gen. Genet.*, 215:431–440, 1989.
Sullivan, Christensen, Quail, "Isolation and characterization of a maize chlorophyll a/b binding protein gene that produces high levels of mRNA in the dark," *Mol. Gen. Genet.*, 215(3):431–440, 1989.
Sutcliffe, "Nucleotide sequence of the ampicillin resistance gene of *Escherichia coli* plasmid pBR322," *Proc. Natl. Acad. Sci.* USA, 75:3737–3741, 1978.
Tanksley et al., *Bio/Technology*, 7:257–264, 1989.
Tarczynski et al., "Expression of a bacterial mtlD gene in transgenic tobacco leads to production and accumulation of mannitol," *Proc. Natl. Acad. Sci.* USA, 89:1–5, 1992.
Tarczynski et al., "Stress Protection of Transgenic Tobacco by Production of the Osmolyte Mannitol," *Science*, 259:508–510, 1993.
Tarczynski et al., *Proc. Natl. Acad. Sci.* USA, 89:2600, 1992.
Thillet et al., *J. Biol. Chem.*, 263:12500–12508, 1988.
Thompson et al., "Characterization of the herbicide-resistance gene bar from *Streptomyces hygroscopicus*," *The EMBO Journal*, 6(9):2519–2523, 1987.
Thompson, Drayton, Frame, Wang, Dunwell, "Maize transformation utilizing silicon carbide whiskers: A review," *Euphytica*, 85(1–3):75–80, 1995.
Tian, Sequin, Charest, "Expression of the green fluorescent protein gene in conifer tissues," *Plant Cell Rep.*, 16:267–271, 1997
Tomes et al., "Transgenic tobacco plants and their progeny derived by microprojectile bombardment of tobacco leaves." *Plant. Mol. Biol.* 14(2):261–268, 1990.
Tomic et al., *Nucl. Acids Res.*, 12:1656, 1990.
Torbet, Rines, Somers, "Transformation of oat using mature embryo-derived tissue cultures," *Crop Science*, 38(1):226–231, 1998.
Torbet, Rines, Somers, "Use of paromomycin as a selective agent for oat transformation," *Plant Cell Reports*, 14(10):635–640, 1995.
Tsukada; Kusano; Kitagawa, "Introduction of foreign genes into tomato protoplasts by electroporation," *Plant Cell Physiol.*, 30(4)599–604, 1989.

Twell et al., "Transient Expression of Chimeric Genes Delivered into Pollen by Microprojectile Bombardment," *Plant Physiology*, 91:1270–1274, 1989.

Ugaki et al., *Nucl. Acid Res.*, 19:3 71–377, 1991.

Upender et al., *Biotechniques*, 18:29–31, 1995.

Vaeck. et al., *Nature*, Vol. 328, p. 33. 1987.

Van Blokland, Van der Geest, Mol, Kooter, "Transgene-mediated suppression of chalcone synthase expression in *Petunia hybrida* results from an increase in RNA turnover," *Plant J.*, 6:861–877, 1994.

Van der Krol, Mur, Beld, Mol, Stuitje, "Flavonoid genes in petunia: addition of a limiting number of copies may lead to a suppression of gene expression," *Plant Cell*, 2:291–99, 1990.

Van Eck; Blowers; Earle, "Stable transformation of tomato cell cultures after bombardment with plasmid and YAC DNA," *Plant Cell Reports*, 14(5):299–304, 1995.

Vasil et al., *Plant Physiol.*, 91:1575–1579, 1989.

Vaucheret, "Identification of a general silencer for 19S and 35S promoters in a transgenic tobacco plant:90 bp of homology in the promoter sequence are sufficient for trans-inactivation," *C.R. Acad. Sci. III*, 316:1471–83, 1993.

Vernon and Bohnert, The *EMBO J.*, 11:2077–2085, 1992.

Vodkin et al., *Cell*, 34:1023, 1983.

Vogel et al., *J. Cell Biochem.*, 13D(Supp):312, 1989.

Walker et al., *Proc. Natl. Acad. Sci.* USA, 84:6624–6628, 1987.

Walker et al., *Proc. Natl. Acad. Sci.* USA, 89:392–396, 1992.

Wandelt and Feix, "Sequence of a 21 kd zein gene from maize containing an in-frame stop codon," *Nucl. Acids Res.*, 17(6):2354, 1989.

Wang et al., "Characterization of cis-Acting Elements Regulating Transcription from the Promoter of a Constitutively Active Rice Actin Gene," *Molecular and Cellular Biology*, 12(8):3399–3406, 1992.

Watrud et al., *In: Engineered Organisms and the Environment*, 1985.

Watson and Ramstad, eds., Corn: *Chemistry and Technology*, 1987.

Withers and King, *Plant Physiol.*, 64:675–678, 1979.

Wolter et al., *The EMBO J.*, 4685–4692, 1992.

Wu et al., *Genomics*, 4:560, 1989.

Wyn-Jones and Storey, 1982.

Xiang and Guerra, *Plant Physiol.*, 102:287–293, 1993.

Xu et al., *Plant Physiol.*, 110:249–257, 1996.

Yamaguchi-Shinozaki et al., *Plant Cell Physiol.*, 33:217–224, 1992.

Yanagisawa and Izui, "Maize phosphoenolpyruvate carboxylase involved in C4 photosynthesis: nucleotide sequence analysis of the 5' flanking region of the gene," *J. Biochem.*, 106(6):982–987, 1989.

Yang and Russell, *Proc. Natl. Acad. Sci.* USA, 87:4144–4148, 1990.

Zheng and Edwards, "Expression of resistance to barley stripe mosaic virus in barley and oat protoplasts, *J. Gen. Virol.*, 71:1865–1868, 1990.

Zhou; Stiff; Konzak, "Stably transformed callus of wheat by electroporation-induced direct gene transfer" *Plant Cell Reports*, 12(11).612–616, 1993.

Zukowsky et al., *Proc. Natl. Acad. Sci.* USA, 80:1101–1105, 1983.

---

What is claimed is:

1. An isolated gammia coixin promoter comprising the nucleic acid sequence of SEQ ID NO:8.

2. A fertile transgenic plant comprising a selected DNA, said selected DNA comprising a gamma coixin promoter according to claim 1.

3. The fertile transgenic plant of claim 2, wherein said promoter is operably linked to an exogenous gene selected from the group consisting of an insect resistance gene, a disease resistance gene, a herbicide resistance gene, a gene affecting grain composition or quality, a nutrient utilization gene, a mycotoxin reduction gene, a male sterility gene, a selectable marker gene, a screenable marker gene, a negative selectable marker, a gene affecting plant agronomic characteristics, and an environment or stress resistance gene.

4. A progeny plant of any generation of the plant of claim 2 or 3, wherein said progeny plant comprises said selected DNA.

5. The fertile transgenic plant of claim 2 or 3, wherein said plant is a monocot plant selected from the group consisting of rice, wheat, barley, rye, sorghum and maize.

6. The fertile transgenic plant of claim 5, wherein the monocot is maize.

7. The fertile transgenic plant of claim 2 or 3 wherein said plant is a dicot plant selected from the group consisting of tobacco, tomato, potato, soybean and cotton.

8. An isolated gamma coixin promoter comprising the nucleic acid sequence of SEQ ID NO:18 operably linked to an enhancer.

9. An isolated gamma coixin promoter comprising the nucleic acid sequence of SEQ ID NO:19 operably linked to an enhancer.

10. A fertile transgenic plant comprising a selected DNA, sad selected DNA comprising the isolated gamma coixin promoter of claim 8 or 9.

11. A progeny plant of any generation of the plant of claim 10, wherein said progeny plant comprises said selected DNA.

12. The fertile transgenic plant of claim 10, wherein said plant is a monocot selected from the group consisting of rice, wheat, barley, rye, sorghum and maize.

13. The fertile transgenic plant of claim 12, wherein the monocot is maize.

14. The fertile transgenic plant of claim 10, wherein said plant is a dicot plant selected from the group of tobacco, tomato, potato, soybean and cotton.

15. The fertile transgenic plant of claim 10, wherein said promoter is operably linked to an exogenous gene selected from the group consisting of an insect resistance gene, a disease resistance gene, a herbicide resistance gene, a gene affecting grain composition or quality, a nutrient utilization gene, a mycotoxin reduction gene, a male sterility gene, a selectable marker gene, a screenable marker gene, a negative selectable marker, a gene affecting plant agronomic characteristics, and an environment or stress resistance gene.

* * * * *

UNITED STATES PATENT AND TRADEMARK OFFICE
CERTIFICATE OF CORRECTION

PATENT NO. : 6,635,806 B1  Page 1 of 1
DATED : October 21, 2003
INVENTOR(S) : Kriz et al.

It is certified that error appears in the above-identified patent and that said Letters Patent is hereby corrected as shown below:

<u>Column 118,</u>
Line 5, delete "sad" and insert -- said --.

Signed and Sealed this

Thirteenth Day of January, 2004

JON W. DUDAS
*Acting Director of the United States Patent and Trademark Office*